(12) United States Patent
Cohen-Haguenauer et al.

(10) Patent No.: US 8,828,718 B2
(45) Date of Patent: Sep. 9, 2014

(54) GENE TRANSFER VECTORS COMPRISING GENETIC INSULATOR ELEMENTS AND METHODS TO IDENTIFY GENETIC INSULATOR ELEMENTS

(75) Inventors: Odile Cohen-Haguenauer, Paris (FR); Christian Auclair, Paris (FR)

(73) Assignee: Centre National de la Recherche Scientifique, Paris (FR)

( * ) Notice: Subject to any disclaimer, the term of this patent is extended or adjusted under 35 U.S.C. 154(b) by 24 days.

(21) Appl. No.: 13/262,696

(22) PCT Filed: Apr. 2, 2010

(86) PCT No.: PCT/IB2010/000950
§ 371 (c)(1),
(2), (4) Date: Jan. 3, 2012

(87) PCT Pub. No.: WO2010/113037
PCT Pub. Date: Oct. 7, 2010

(65) Prior Publication Data
US 2012/0115227 A1 May 10, 2012

Related U.S. Application Data

(60) Provisional application No. 61/166,420, filed on Apr. 3, 2009, provisional application No. 61/254,351, filed on Oct. 23, 2009.

(51) Int. Cl.
*C12N 15/00* (2006.01)
*C12N 5/071* (2010.01)

(52) U.S. Cl.
USPC ........................ 435/320.1; 435/366

(58) Field of Classification Search
USPC ............................. 435/320.1, 366
See application file for complete search history.

(56) References Cited

U.S. PATENT DOCUMENTS

| | | | |
|---|---|---|---|
| 6,312,948 B1 * | 11/2001 | Cohen-Haguenauer ... | 435/320.1 |
| 2003/0159159 A1 * | 8/2003 | Linnik et al. ........... | 800/8 |
| 2003/0185857 A1 * | 10/2003 | Shaul et al. ............ | 424/225.1 |
| 2004/0002158 A1 | 1/2004 | Chang | |
| 2006/0003322 A1 * | 1/2006 | Bentwich ................ | 435/6 |
| 2006/0179500 A1 | 8/2006 | Meade et al. | |
| 2011/0294873 A1 * | 12/2011 | Mermod et al. ......... | 514/44 R |
| 2013/0018089 A1 * | 1/2013 | Klinman et al. ......... | 514/44 R |
| 2013/0023446 A1 * | 1/2013 | Khvorova et al. ....... | 506/16 |

FOREIGN PATENT DOCUMENTS

| | | |
|---|---|---|
| WO | 01 02553 | 1/2001 |
| WO | 2006 055931 | 5/2006 |
| WO | 2010 046493 | 4/2010 |

OTHER PUBLICATIONS

Ye et al (Biochemical and Biophysical Research Communications 307:759-764, 2003).*
Tarapore, P. et al., "DNA bindging and transcriptional activation by the Ski oncoprotein mediated by interaction with NFI", Nucleic Acids Research, vol. 25, No. 19, pp. 3895-3903, (Oct. 1, 1997), XP-002592948.
West, A. G. et al., "Insulators: many functions, many mechanisms", Genes & Development, vol. 16, No. 3, pp. 271-288, (Feb. 1, 2002), XP-002249349.
Kim, T. H. et al, "Analysis of the Vertebrate Insulator Protein CTCF-Binding Sited in the Human Genome", Cell, vol. 128, No. 6, pp. 1231-1245, (Mar. 23, 2007), XP-002592949.
Rivella, S. et al., "The cHS4 Insulator Increase the Probability of Retroviral Expression at Random Chromosomal Integration Sites", Journal of Virology, vol. 74, No. 10, pp. 4679-4687, (May 1, 2000), XP-002249347.
Bell, A. C. et al., "The Protein CTCF is Required for the Enhancer Blocking Activity of Vertebrate Insulators", Cell, vol. 98, No. 9, pp. 387-396, (Aug. 6, 1999), XP-000926124.
International Search Report Issued Aug. 6, 2010 in PCT/IB10/000950 filed Apr. 2, 2010.

* cited by examiner

*Primary Examiner* — Marcia S Noble
(74) *Attorney, Agent, or Firm* — Oblon, Spivak, McClelland, Maier & Neustadt, L.L.P.

(57) ABSTRACT

The present invention relates to a gene transfer vector (GTV) and in particular to an integrating gene transfer vector (IGTV), which comprises at least one genetic insulator element (GIE), wherein the each comprises at least two copies of an element selected from the group consisting of: a CTF binding site; a first CTCF binding site and a second CTCF binding site, wherein the first and the second CTCF binding sites are derived from the regulatory sequences of different genes.

13 Claims, 37 Drawing Sheets

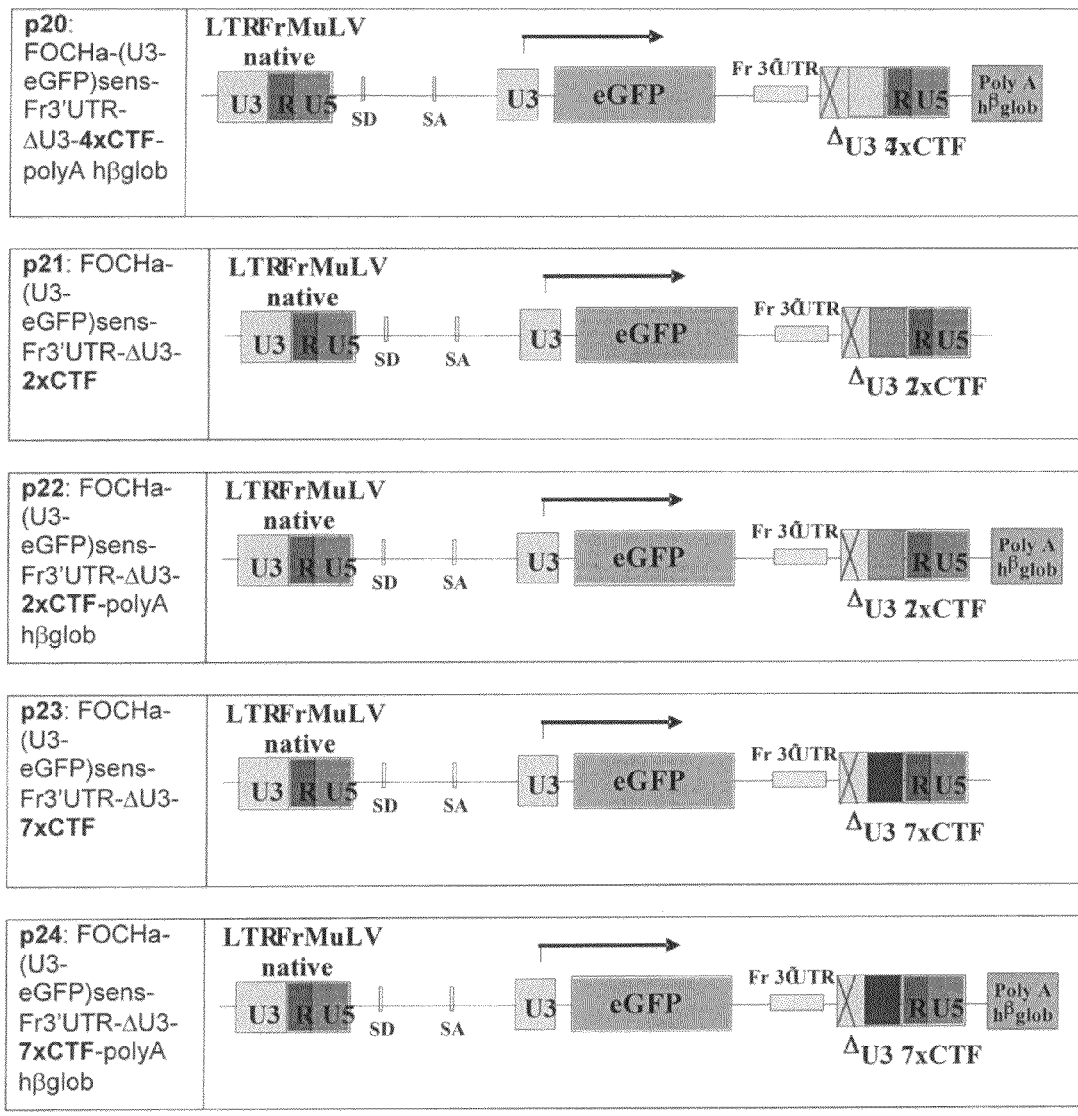
Fig.1A(1)

| Vector | Number Cells visualised | Number GFP+ cells | Percentage GFP+ cells | Mean Fluorescence |
|---|---|---|---|---|
| Test 1 | 2669 | 1214 | 0.45% | 972.55% |
| Ref 1 | 6571 | 3050 | 0.46% | 103.23% |
| DCaro4.23 | 3337 | 1394 | 0.42% | 672.55% |
| DCarohP4.41 | 5850 | 2546 | 0.44% | 62.95% |

SEQUENCE LISTING

```
<160> NUMBER OF SEQ ID NOS: 42

<210> SEQ ID NO 1
<211> LENGTH: 558
<212> TYPE: DNA
<213> ORGANISM: Artificial Sequence
<220> FEATURE:
<223> OTHER INFORMATION: Description of Artificial Sequence: Synthetic
      FrMuLV LTR polynucleotide

<400> SEQUENCE: 1
aatgaaagac cccaccaaat tgcttagcct gatagccgca gtaacgccat tttgcaaggc      60
atggaaaaat accaaaccaa gaatagagaa gttcagatca agggcgggta cacgaaaaca     120
gctaacgttg ggccaaacag gatatctgcg gtgagcagtt tcggcccggg ccccggggcca    180 agaacagatg gtcaccgcgg ttcggccccg gcccggggcc aagaacagat ggtccccaga     240
tatggcccaa ccctcagcag tttcttaaga cccatcagat gtttccaggc tcccccaagg    300
acctgaaatg accctgtgcc ttatttgaat taaccaatca gcctgcttct cgcttctgtt    360
cgcgcgcttc tgcttcccga gctctataaa agagctcaca accctcact cggcgcgcca     420 gtcctccgat agactgagtc gcccgggtac ccgtgtatcc aataaatcct cttgctgttg    480
catccgactc gtggtctcgc tgttccttgg gagggtctcc tcagagtgat tgactacccg     540
tctcgggggt ctttcatt                                                   558

<210> SEQ ID NO 2
<211> LENGTH: 171
<212> TYPE: DNA
<213> ORGANISM: Artificial Sequence
<220> FEATURE:
```

<223> OTHER INFORMATION: Description of Artificial Sequence: Synthetic
      LTR FrMuLV Delta U3 polynucleotide

<400> SEQUENCE: 2
aatgaaagac cccaccaaat tgcttacgcg ccagtcctcc gatagactga gtcgcccggg    60
tacccgtgta tccaataaat cctcttgctg ttgcatccga ctcgtggtct cgctgttcct   120
tgggagggtc tcctcagagt gattgactac ccgtctcggg ggtctttcat t            171

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      BamHI-ClaI linker oligonucleotide

<400> SEQUENCE: 3
ggatccatcg at                                                         12

<210> SEQ ID NO 4
<211> LENGTH: 183
<212> TYPE: DNA
<213> ORGANISM: Artificial Sequence
<220> FEATURE:
<223> OTHER INFORMATION: Description of Artificial Sequence: Synthetic
      LTR FrMuLV delta U3 + linker polynucleotide

<400> SEQUENCE: 4
aatgaaagac cccaccaaat tgctggatcc atcgattacg cgccagtcct ccgatagact    60
gagtcgcccg ggtacccgtg tatccaataa atcctcttgc tgttgcatcc gactcgtggt   120
ctcgctgttc cttgggaggg tctcctcaga gtgattgact acccgtctcg gggtctttc    180 att                                                                  183

<210> SEQ ID NO 5
<211> LENGTH: 243
<212> TYPE: DNA
<213> ORGANISM: Artificial Sequence
<220> FEATURE:
<223> OTHER INFORMATION: Description of Artificial Sequence: Synthetic
      pSIN-18 3'UTR polynucleotide

<400> SEQUENCE: 5
tggaagggct aattcactcc caacgaagac aagatctgct ttttgcctgt actgggtctc    60
tctggttaga ccagatctga gcctgggagc tctctggcta actagagaac ccactgctta   120
agcctcaata agcttgcct tgagtgcttc aagtagtgtg tgcccgtctg ttgtgtgact   180
ctggtaacta gagatccctc agaccctttt agtcagtgtg gaaaatctct agcagtgggt   240
gat                                                                  243

<210> SEQ ID NO 6
<211> LENGTH: 269
<212> TYPE: DNA
<213> ORGANISM: Artificial Sequence
<220> FEATURE:
<223> OTHER INFORMATION: Description of Artificial Sequence: Synthetic
      6xCTCF polynucleotide

<400> SEQUENCE: 6
ggatccccca gggatgtaat tacgtccctc ccccgctagg gggcagcacc caggcctgca    60
ctgccgcctg ccggcagggg tccagtcccc agggatgtaa ttatgtccct cccccgctag   120

```
ggggcagcac ccaggcctgc actgccgcct gccggcaggg gtccagtccc caggatgta    180 attacgtccc tcccccgcta gggggcagca cccaggcctg cactgccgcc tgccggcagg    240
ggtccagtcc ccggggagct ccaatcgat                                      269
```

```
<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence: Synthetic
      CTCF1 oligonucleotide

<400> SEQUENCE: 7
ccagggatgt aattacgtcc ctcccccgct aggggcagc a                         41
```

```
<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      CTCF2 oligonucleotide

<400> SEQUENCE: 8
cccaggcctg cactgccgcc tgccggcagg ggtccagtc                           39
```

```
<210> SEQ ID NO 9
<211> LENGTH: 64
<212> TYPE: DNA
<213> ORGANISM: Artificial Sequence
<220> FEATURE:
<223> OTHER INFORMATION: Description of Artificial Sequence: Synthetic
      2xCTF oligonucleotide

<400> SEQUENCE: 9
atcgataagc ttgcattggc aacgtgccat aagcattggc aacgtgccat aagcgggggg    60
atcc                                                                 64
```

```
<210> SEQ ID NO 10
<211> LENGTH: 108
<212> TYPE: DNA
<213> ORGANISM: Artificial Sequence
<220> FEATURE:
<223> OTHER INFORMATION: Description of Artificial Sequence: Synthetic
      4xCTF polynucleotide

<400> SEQUENCE: 10
atcgataagc ttgcattggc aacgtgccat aagcattggc aacgtgccat aagcattggc    60
aacgtgccat aagcattggc aacgtgccat aagcgaattg ggggatcc                 108
```

```
<210> SEQ ID NO 11
<211> LENGTH: 168
<212> TYPE: DNA
<213> ORGANISM: Artificial Sequence
<220> FEATURE:
<223> OTHER INFORMATION: Description of Artificial Sequence: Synthetic
      7xCTF polynucleotide

<400> SEQUENCE: 11
atcgataagc ttgcattggc aacgtgccat aagcattggc aacgtgccat aagcattggc    60
aacgtgccat aagcattggc aacgtgccat aagcattggc aacgtgccat aagcattggc    120
aacgtgccat aagcattggc aacgtgccat aagcgaattg ggggatcc                 168
```

<210> SEQ ID NO 12
<211> LENGTH: 452
<212> TYPE: DNA
<213> ORGANISM: Artificial Sequence
<220> FEATURE:
<223> OTHER INFORMATION: Description of Artificial Sequence: Synthetic
      LTR FrMuLV Delta U 3 6xCTCF polynucleotide

<400> SEQUENCE: 12

```
aatgaaagac cccaccaaat tgcttacgga tccggatccc ccagggatgt aattacgtcc      60
ctcccccgct aggggggcagc acccaggcct gcactgccgc ctgccggcag gggtccagtc   120
cccagggatg taattatgtc cctcccccgc taggggggcag cacccaggcc tgcactgccg   180
cctgccggca ggggtccagt ccccagggat gtaattacgt ccctcccccg ctaggggggca   240 gcacccaggc ctgcactgcc gcctgccggc aggggtccag tccccgggga gctccaatcg   300
atatcgatgc gccagtcctc cgatagactg agtcgcccgg gtacccgtgt atccaataaa   360
tcctcttgct gttgcatccg actcgtggtc tcgctgttcc ttgggagggt ctcctcagag   420
tgattgacta cccgtctcgg ggtctttca tt                                   452
```

<210> SEQ ID NO 13
<211> LENGTH: 241
<212> TYPE: DNA
<213> ORGANISM: Artificial Sequence
<220> FEATURE:
<223> OTHER INFORMATION: Description of Artificial Sequence: Synthetic
      LTR FrMuLV Delta U 3 2xCTF polynucleotide

<400> SEQUENCE: 13

```
aatgaaagac cccaccaaat tgcttacgga tccggatccc cccgcttatg gcacgttgcc      60
aatgcttatg gcacgttgcc aatgcaagct tatcgatgcg ccagtcctcc gatagactga   120
gtcgcccggg tacccgtgta tccaataaat cctcttgctg ttgcatccga ctcgtggtct   180
cgctgttcct tgggagggtc tcctcagagt gattgactac ccgtctcggg ggtctttcat   240
t                                                                     241
```

<210> SEQ ID NO 14
<211> LENGTH: 291
<212> TYPE: DNA
<213> ORGANISM: Artificial Sequence
<220> FEATURE:
<223> OTHER INFORMATION: Description of Artificial Sequence: Synthetic
      LTR FrMuLV Delta U 3 4xCTF polynucleotide

<400> SEQUENCE: 14

```
aatgaaagac cccaccaaat tgcttacgga tccggatccc ccaattcgct tatggcacgt      60
tgccaatgct tatggcacgt tgccaatgct tatggcacgt tgccaatgct tatggcacgt   120
tgccaatgca agcttatcga tatcgatgcg ccagtcctcc gatagactga gtcgcccggg   180
tacccgtgta tccaataaat cctcttgctg ttgcatccga ctcgtggtct cgctgttcct   240
tgggagggtc tcctcagagt gattgactac ccgtctcggg ggtctttcat t             291
```

<210> SEQ ID NO 15
<211> LENGTH: 440
<212> TYPE: DNA
<213> ORGANISM: Artificial Sequence
<220> FEATURE:
<223> OTHER INFORMATION: Description of Artificial Sequence: Synthetic
      LTR FrMuLV Delta U 3 7xCTF polynucleotide

<400> SEQUENCE: 15

```
aatgaaagac cccaccaaat tgcttacgga tcccccaggg atgtaattac gtccctcccc      60
cgctaggggg cagcacccag gcctgcactg ccgcctgccg gcaggggtcc agtccccagg     120
gatgtaatta tgtccctccc ccgctagggg cagcaccca ggcctgcact gccgcctgcc     180 ggcagggtc cagtccccag ggatgtaatt acgtccctcc cccgctaggg ggcagcaccc      240
aggcctgcac tgccgcctgc cggcaggggt ccagtccccg gggagctcca atcgatgcgc     300
cagtcctccg atagactgag tcgcccgggt accgtgtat ccaataaatc tcttgctgt       360 tgcatccgac tcgtggtctc gctgttcctt gggagggtct cctcagagtg attgactacc     420
cgtctcgggg gtctttcatt                                                 440

<210> SEQ ID NO 16
<211> LENGTH: 300
<212> TYPE: DNA
<213> ORGANISM: Artificial Sequence
<220> FEATURE:
<223> OTHER INFORMATION: Description of Artificial Sequence: Synthetic
      pSIN-18 3'LTR 6xCTCF polynucleotide

<400> SEQUENCE: 16
tggaagggct aattcactcc caacgaagac aagatctggc gattggagct ccccggggac      60 tggaccctg ccggcaggcg gcagtgcagg cctgggtgct gccccctagc ggggaggga      120 cgtaattaca tccctgggga ctggacccct gccggcaggc ggcagtgcag gcctgggtgc     180 tgcccctag cggggaggg acataattac atccctgggg actggacccc tgccggcagg      240
cggcagtgca ggcctgcgat gatctgcttt ttgcctgtac tgggtctctc tggttagacc     300

<210> SEQ ID NO 17
<211> LENGTH: 138
<212> TYPE: DNA
<213> ORGANISM: Artificial Sequence
<220> FEATURE:
<223> OTHER INFORMATION: Description of Artificial Sequence: Synthetic
      pSIN-18 3'LTR 2xCTF polynucleotide

<400> SEQUENCE: 17
tggaagggct aattcactcc caacgaagac aagatctggc ccccgcttat ggcacgttgc      60
caatgcttat ggcacgttgc caatgcaagc ttatcgatga tctgcttttt gcctgtactg     120
ggtctctctg gttagacc                                                   138

<210> SEQ ID NO 18
<211> LENGTH: 182
<212> TYPE: DNA
<213> ORGANISM: Artificial Sequence
<220> FEATURE:
<223> OTHER INFORMATION: Description of Artificial Sequence: Synthetic
      pSIN-18 3'LTR 4xCTF polynucleotide

<400> SEQUENCE: 18
tggaagggct aattcactcc caacgaagac aagatctggc cccaattcgc ttatggcacg      60
ttgccaatgc ttatggcacg ttgccaatgc ttatggcacg ttgccaatgc ttatggcacg     120
ttgccaatgc aagcttatcg atgatctgct ttttgcctgt actgggtctc tctggttaga     180
cc                                                                    182

<210> SEQ ID NO 19
<211> LENGTH: 240
<212> TYPE: DNA
<213> ORGANISM: Artificial Sequence
```

```
<220> FEATURE:
<223> OTHER INFORMATION: Description of Artificial Sequence: Synthetic
      pSIN-18 3'LTR 7xCTF polynucleotide

<400> SEQUENCE: 19
tggaagggct aattcactcc caacgaagac aagatctggc gataagcttg cattggcaac      60
gtgccataag cattggcaac gtgccataag cattggcaac gtgccataag cattggcaac     120
gtgccataag cattggcaac gtgccataag cattggcaac gtgccataag cattggcaac     180
gtgccataag cggggggcgat gatctgctttt ttgcctgtac tgggtctctc tggttagacc   240

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      sense oligonucleotide

<400> SEQUENCE: 20
aagaagacaa gatcatcgat aagcttgcat tggc                                  34

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      reverse oligonucleotide

<400> SEQUENCE: 21
tttgatcaag tcttcggatc ccccaattcg c                                     31

<210> SEQ ID NO 22
<211> LENGTH: 134
<212> TYPE: DNA
<213> ORGANISM: Artificial Sequence
<220> FEATURE:
<223> OTHER INFORMATION: Description of Artificial Sequence: Synthetic
      FrMuLV enhancer polynucleotide

<400> SEQUENCE: 22
tagttcaatt tgttaaagac aggatctcag tagtccaggc tttagtcctg actcaacaat      60
accaccagct aaaaccacta gaatacgagc cacaataaat aaaagatttt atttagtttc     120
cagaaaaagg gggg                                                       134

<210> SEQ ID NO 23
<211> LENGTH: 445
<212> TYPE: DNA
<213> ORGANISM: Artificial Sequence
<220> FEATURE:
<223> OTHER INFORMATION: Description of Artificial Sequence: Synthetic
      3' sequence of p23 polynucleotide

<400> SEQUENCE: 23
gcggccgcaa gtcgacctgc aggcatgcac agatcccgcc tagttcaatt tgttaaagac      60
aggatctcag tagtccaggc tttagtcctg actcaacaat accaccagct aaaaccacta    120
gaatacgagc cacaataaat aaaagatttt atttagtttc cagaaaaagg gggtcggcc     180 gcaatgaaag accccaccaa attgcttacg gatcccccaa ttcgcttatg gcacgttgcc    240
aatgcttatg gcacgttgcc aatgcttatg gcacgttgcc aatgcttatg gcacgttgcc    300
aatgcttatg gcacgttgcc aatgcttatg gcacgttgcc aatgcttatg gcacgttgcc    360
```
aatgcaagct tatcgatgcg ccagtcctcc gatagactga gtcgcccggg tacccgtgta    420
tccaataaat cctcttgctg ttgca                                          445

<210> SEQ ID NO 24
<211> LENGTH: 134
<212> TYPE: DNA
<213> ORGANISM: Artificial Sequence
<220> FEATURE:
<223> OTHER INFORMATION: Description of Artificial Sequence: Synthetic
      artificial polyA polynucleotide

<400> SEQUENCE: 24
gctcgctttc ttgctgtcca atttctatta aaggttcctt tgttccctaa gtccaactac    60
taaactgggg gatattatga agggccttga gcatctggat tctgcctaat aaaaaacatt    120 tattttcat tgca                                                       134

<210> SEQ ID NO 25
<211> LENGTH: 434
<212> TYPE: DNA
<213> ORGANISM: Artificial Sequence
<220> FEATURE:
<223> OTHER INFORMATION: Description of Artificial Sequence: Synthetic
      U3 polynucleotide

<400> SEQUENCE: 25
ctcgagaagc ttgatatcgc ttagcctgat agccgcagta acgccatttt gcaaggcatg    60 gaaaatacc aaaccaagaa tagagaagtt cagatcaagg gcgggtacac gaaaacagct    120
aacgttgggc caaacaggat atctgcggtg agcagtttcg gccccggccc ggggccaaga   180
acagatggtc accgcggttc ggccccggcc cggggccaag aacagatggt ccccagatat   240
ggcccaaccc tcagcagttt cttaagaccc atcagatgtt tccaggctcc cccaaggacc   300
tgaaatgacc ctgtgcctta tttgaattaa ccaatcagcc tgcttctcgc ttctgttcgc   360
gcgcttctgc ttcccgagct ctataaaaga gctcacaacc cctcactcgg cgcgtcgcgg   420
aattccgcgg atcc                                                     434

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      CTF repeat oligonucleotide

<400> SEQUENCE: 26
gcattggcaa cgtgccataa                                                20

<210> SEQ ID NO 27
<211> LENGTH: 14
<212> TYPE: DNA
<213> ORGANISM: Artificial Sequence
<220> FEATURE:
<223> OTHER INFORMATION: Description of Artificial Sequence: Synthetic
      CTCF consensus 1 oligonucleotide
<220> FEATURE:
<221> NAME/KEY: modified_base
<222> LOCATION: (6)..(6)
<223> OTHER INFORMATION: a, c, t or g
<220> FEATURE:
<221> NAME/KEY: modified_base
<222> LOCATION: (9)..(9)
<223> OTHER INFORMATION: a, c, t or g

```
<400> SEQUENCE: 27
ccgcgnggng gcag                                                    14

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence: Synthetic
      CTF consensus 1 oligonucleotide

<400> SEQUENCE: 28
actggccagc agccaac                                                 17

<210> SEQ ID NO 29
<211> LENGTH: 7
<212> TYPE: DNA
<213> ORGANISM: Artificial Sequence
<220> FEATURE:
<223> OTHER INFORMATION: Description of Artificial Sequence: Synthetic
      CTF consensus 2 oligonucleotide

<400> SEQUENCE: 29 agccaat                                                             7

<210> SEQ ID NO 30
<211> LENGTH: 5
<212> TYPE: DNA
<213> ORGANISM: Artificial Sequence
<220> FEATURE:
<223> OTHER INFORMATION: Description of Artificial Sequence: Synthetic
      CTF consensus 3 oligonucleotide

<400> SEQUENCE: 30 ccaat                                                               5

<210> SEQ ID NO 31
<211> LENGTH: 5
<212> TYPE: DNA
<213> ORGANISM: Artificial Sequence
<220> FEATURE:
<223> OTHER INFORMATION: Description of Artificial Sequence: Synthetic
      CTCF consensus 2 oligonucleotide

<400> SEQUENCE: 31 ccctc                                                               5

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Synthetic
      Ins_BbsI_6sens oligonucleotide

<400> SEQUENCE: 32
aagaagacaa gatcggatcc cccagggatg taat                              34

<210> SEQ ID NO 33
<211> LENGTH: 34
<212> TYPE: DNA
<213> ORGANISM: Artificial Sequence
<220> FEATURE:
<223> OTHER INFORMATION: Description of Artificial Sequence: Synthetic
      Ins_BbsI_6rev oligonucleotide

<400> SEQUENCE: 33
```

-continued

```
tttgatcaag tcttcatcga ttggagctcc ccgg                           34
```

<210> SEQ ID NO 34
<211> LENGTH: 6551
<212> TYPE: DNA
<213> ORGANISM: Artificial Sequence
<220> FEATURE:
<223> OTHER INFORMATION: Description of Artificial Sequence: Synthetic
      Test1-cPPT polynucleotide

<400> SEQUENCE: 34

```
caggtggcac ttttcgggga aatgtgcgcg gaacccctat ttgtttattt ttctaaatac    60
attcaaatat gtatccgctc atgagacaat aaccctgata aatgcttcaa taatattgaa   120
aaaggaagag tatgagtatt caacatttcc gtgtcgccct tattcccttt tttgcggcat   180
tttgccttcc tgttttttgct cacccagaaa cgctggtgaa agtaaaagat gctgaagatc   240
agttgggtgc acgagtgggt tacatcgaac tggatctcaa cagcggtaag atccttgaga   300
gttttcgccc cgaagaacgt tttccaatga tgagcacttt taaagttctg ctatgtggcg   360
cggtattatc ccgtattgac gccgggcaag agcaactcgg tcgccgcata cactattctc   420
agaatgactt ggttgagtac tcaccagtca cagaaaagca tcttacggat ggcatgacag   480
taagagaatt atgcagtgct gccataacca tgagtgataa cactgcggcc aacttacttc   540
tgacaacgat cggaggaccg aaggagctaa ccgcttttttt gcacaacatg ggggatcatg   600
taactcgcct tgatcgttgg gaaccggagc tgaatgaagc cataccaaac gacgagcgtg   660
acaccacgat gcctgtagca atggcaacaa cgttgcgcaa actattaact ggcgaactac   720
ttactctagc ttcccggcaa caattaatag actggatgga ggcggataaa gttgcaggac   780
cacttctgcg ctcggccctt ccggctggct ggtttattgc tgataaatct ggagccggtg   840
agcgtgggtc tcgcggtatc attgcagcac tggggccaga tggtaagccc tcccgtatcg   900
tagttatcta cacgacgggg agtcaggcaa ctatggatga acgaaataga cagatcgctg   960
agataggtgc ctcactgatt aagcattggt aactgtcaga ccaagtttac tcatatatac  1020
tttagattga tttaaaactt cattttttaat ttaaaaggat ctaggtgaag atcctttttg  1080
ataatctcat gaccaaaatc ccttaacgtg agttttcgtt ccactgagcg tcagaccccg  1140
tagaaaagat caaaggatct tcttgagatc cttttttttct gcgcgtaatc tgctgcttgc  1200
aaacaaaaaa accaccgcta ccagcggtgg tttgtttgcc ggatcaagag ctaccaactc  1260
tttttccgaa ggtaactggc ttcagcagag cgcagatacc aaatactgtc cttctagtgt  1320
agccgtagtt aggccaccac ttcaagaact ctgtagcacc gcctacatac ctcgctctgc  1380
taatcctgtt accagtggct gctgccagtg gcgataagtc gtgtcttacc gggttggact  1440
caagacgata gttaccggat aaggcgcagc ggtcgggctg aacggggggt tcgtgcacac  1500
agcccagctt ggagcgaacg acctacaccg aactgagata cctacagcgt gagctatgag  1560
aaagcgccac gcttcccgaa gggagaaagg cggacaggta tccggtaagc ggcagggtcg  1620
gaacaggaga gcgcacgagg gagcttccag ggggaaacgc ctggtatctt tatagtcctg  1680
tcgggtttcg ccacctctga cttgagcgtc gatttttgtg atgctcgtca ggggggcgga  1740
gcctatggaa aaacgccagc aacgcggcct ttttacggtt cctggccttt tgctggcctt  1800
ttgctcacat gttctttcct gcgttatccc ctgattctgt ggataaccgt attaccgcct  1860
ttgagtgagc tgataccgct cgccgcagcc gaacgaccga gcgcagcgag tcagtgagcg  1920
aggaagcgga agagcgccca atacgcaaac cgcctctccc cgcgcgttgg ccgattcatt  1980
```

```
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttaat   2220
gtagtcttat gcaatactct tgtagtcttg caacatggta acgatgagtt agcaacatgc   2280
cttacaagga gagaaaaagc accgtgcatg ccgattggtg gaagtaaggt ggtacgatcg   2340
tgccttatta ggaaggcaac agacgggtct gacatggatt ggacgaacca ctgaattgcc   2400
gcattgcaga gatattgtat ttaagtgcct agctcgatac aataaacggg tctctctggt   2460
tagaccagat ctgagcctgg gagctctctg gctaactagg gaacccactg cttaagcctc   2520
aataaagctt gccttgagtg cttcaagtag tgtgtgcccg tctgttgtgt gactctggta   2580
actagagatc cctcagaccc ttttagtcag tgtggaaaat ctctagcagt ggcgcccgaa   2640
cagggacctg aaagcgaaag ggaaaccaga gctctctcga cgcaggactc ggcttgctga   2700
agcgcgcacg gcaagaggcg aggggcggcg actggtgagt acgccaaaaa ttttgactag   2760
cggaggctag aaggagagag atgggtgcga gagcgtcagt attaagcggg ggagaattag   2820
atcgcgatgg gaaaaaattc ggttaaggcc aggggggaaag aaaaaatata aattaaaaca   2880
tatagtatgg gcaagcaggg agctagaacg attcgcagtt aatcctggcc tgttagaaac   2940
atcagaaggc tgtagacaaa tactgggaca gctacaacca tcccttcaga caggatcaga   3000
agaacttaga tcattatata atacagtagc aaccctctat tgtgtgcatc aaaggataga   3060
gataaaagac accaaggaag ctttagacaa gatagaggaa gagcaaaaca aaagtaagac   3120
caccgcacag caagcggccg ctgatcttca gacctggagg aggagatatg agggacaatt   3180
ggagaagtga attatataaa tataaagtag taaaaattga accattagga gtagcaccca   3240
ccaaggcaaa gagaagagtg gtgcagagag aaaaaagagc agtgggaata ggagctttgt   3300
tccttgggtt cttgggagca gcaggaagca ctatgggcgc agcctcaatg acgctgacgg   3360
tacaggccag acaattattg tctggtatag tgcagcagca gaacaatttg ctgagggcta   3420
ttgaggcgca acagcatctg ttgcaactca cagtctgggg catcaagcag ctccaggcaa   3480
gaatcctggc tgtggaaaga tacctaaagg atcaacagct cctggggatt tggggttgct   3540
ctggaaaact catttgcacc actgctgtgc cttggaatgc tagttggagt aataaatctc   3600
tggaacagat tggaatcaca cgacctggat ggagtgggac agagaaatta acaattacac   3660
aagcttaata cactccttaa ttgaagaatc gcaaaaccag caagaaaaga atgaacaaga   3720
attattggaa ttagataaat gggcaagttt gtggaattgg tttaacataa caattggct   3780 gtggtatata aaattattca taatgatagt aggaggcttg gtaggtttaa gaatagtttt   3840
tgctgtactt tctatagtga atagagttag gcagggatat tcaccattat cgtttcagac   3900
ccacctccca accccgaggg gacccgacag gcccgaagga atagaagaag aaggtggaga   3960
gagagacaga gacagatcca ttcgattagt gaacggatct cgacggtatc gatcacgaga   4020
ctagcctcga gaagcttgat atcgcttagc ctgatagccg cagtaacgcc attttgcaag   4080
gcatggaaaa ataccaaacc aagaatagag aagttcagat caagggcggg tacacgaaaa   4140
cagctaacgt tgggccaaac aggatatctg cggtgagcag tttcggcccc ggcccggggc   4200
caagaacaga tggtcaccgc ggttcggccc cggcccgggg ccaagaacag atggtcccca   4260
gatatggccc aaccctcagc agtttcttaa gacccatcag atgtttccag gctcccccaa   4320
```

```
ggacctgaaa tgaccctgtg ccttatttga attaaccaat cagcctgctt ctcgcttctg    4380
ttcgcgcgct tctgcttccc gagctctata aaagagctca caaccccctca ctcggcgcgt    4440 cgcggaattc cgcgggatcc accggtcgcc accatggtga gcaagggcga ggagctgttc    4500
accggggtgg tgcccatcct ggtcgagctg gacggcgacg taaacggcca caagttcagc    4560
gtgtccggcg agggcgaggg cgatgccacc tacggcaagc tgaccctgaa gttcatctgc    4620
accaccggca agctgcccgt gccctggccc accctcgtga ccaccctgac ctacggcgtg    4680
cagtgcttca gccgctaccc cgaccacatg aagcagcacg acttcttcaa gtccgccatg    4740
cccgaaggct acgtccagga gcgcaccatc ttcttcaagg acgacggcaa ctacaagacc    4800
cgcgccgagg tgaagttcga gggcgacacc ctggtgaacc gcatcgagct gaagggcatc    4860
gacttcaagg aggacggcaa catcctgggg cacaagctgg agtacaacta caacagccac    4920
aacgtctata tcatggccga caagcagaag aacggcatca aggtgaactt caagatccgc    4980
cacaacatcg aggacggcag cgtgcagctc gccgaccact accagcagaa cacccccatc    5040
ggcgacggcc ccgtgctgct gcccgacaac cactacctga gcacccagtc cgccctgagc    5100
aaagacccca acgagaagcg cgatcacatg gtcctgctgg agttcgtgac cgccgccggg    5160
atcactctcg gcatggacga gctgtacaag taaagcggcc gcgtcgacgt cggccatagg    5220 ggtacctttta agaccaatga cttcaaggc agctgtagat cttagccact tttaaaaga    5280 aaaggggga ctgaagggc taattcactc ccaacgaaga caagatctgc tttttgcttg    5340
tactgggtct ctctggttag accagatctg agcctgggag ctctctggct aactagggaa    5400
cccactgctt aagcctcaat aaagcttgcc ttgagtgctt caagtagtgt gtgcccgtct    5460
gttgtgtgac tctggtaact agagatccct cagacccttt tagtcagtgt ggaaaatctc    5520
tagcagtagt agttcatgtc atcttattat tcagtattta aacttgcaa agaaatgaat    5580 atcagagagt gagaggaact tgtttattgc agcttataat ggttacaaat aaagcaatag    5640
catcacaaat ttcacaaata aagcattttt ttcactgcat tctagttgtg gtttgtccaa    5700
actcatcaat gtatcttatc atgtctggct ctagctatcc cgcccctaac tccgcccagt    5760
tccgcccatt ctccgcccca tggctgacta atttttttta tttatgcaga ggccgaggcc    5820
gcctcggcct ctgagctatt ccagaagtag tgaggaggct tttttggagg cctaggcttt    5880
tgcgtcgaga cgtacccaat cgccctata gtgagtcgta ttacgcgcgc tcactggccg    5940
tcgttttaca acgtcgtgac tgggaaaacc ctggcgttac ccaacttaat cgccttgcag    6000
cacatccccc tttcgccagc tggcgtaata gcgaagaggc ccgcaccgat cgcccttccc    6060
aacagttgcg cagcctgaat ggcgaatggc gcgacgcgcc ctgtagcggc gcattaagcg    6120
cggcgggtgt ggtggttacg cgcagcgtga ccgctacact tgccagcgcc ctagcgcccg    6180
ctcctttcgc tttcttccct cctttctcg ccacgttcgc cggctttccc cgtcaagctc    6240
taaatcgggg gctccctta gggttccgat ttagtgcttt acggcacctc gaccccaaaa    6300
aacttgatta gggtgatggt tcacgtagtg gccatcgcc ctgatagacg ttttttcgcc    6360
ctttgacgtt ggagtccacg ttctttaata gtggactctt gttccaaact ggaacaacac    6420
tcaaccctat ctcggtctat tcttttgatt tataagggat tttgccgatt tcggcctatt    6480
ggttaaaaaa tgagctgatt taacaaaaat ttaacgcgaa ttttaacaaa atattaacgt    6540
ttacaatttc c                                                         6551
```

<210> SEQ ID NO 35
<211> LENGTH: 6768

<212> TYPE: DNA
<213> ORGANISM: Artificial Sequence
<220> FEATURE:
<223> OTHER INFORMATION: Description of Artificial Sequence: Synthetic
      P1 polynucleotide

<400> SEQUENCE: 35

```
gaattcgatt agttcaattt gttaaagaca ggatctcagt agtccaggct ttagtcctga     60
ctcaacaata ccaccagcta aaaccactag aatacgagcc acaataaata aaagatttta    120
tttagtttcc agaaaaaggg gggaatgaaa gaccccacca aattgcttag cctgatagcc    180
gcagtaacgc cattttgcaa ggcatggaaa ataccaaac caagaataga gaagttcaga    240
tcaagggcgg gtacacgaaa acagctaacg ttgggccaaa caggatatct gcggtgagca    300
gtttcggccc cggccggggg ccaagaacag atggtcaccg cggttcggcc ccggcccggg    360
gccaagaaca gatggtcccc agatatggcc caaccctcag cagtttctta agacccatca    420
gatgtttcca ggctccccca aggacctgaa atgaccctgt gccttatttg aattaaccaa    480
tcagcctgct tctcgcttct gttcgcgcgc ttctgcttcc cgagctctat aaaagagctc    540
acaacccctc actcggcgcg ccagtcctcc gatagactga gtcgcccggg tacccgtgta    600
tccaataaat cctcttgctg ttgcatccga ctcgtggtct cgctgttcct tgggagggtc    660
tcctcagagt gattgactac ccgtctcggg ggtctttcat ttggggggctc gtccgggatc    720
tggagacccc tgcccaggga ccaccgaccc accaccggga ggtaagctgg ccagcaattg    780
ttctgtgtct gtccattgtc ctgtgtcttt gattgatttt atgcgcctgt gtctgtacta    840
gttggccgac tagattggta tctggcggat ccgtggtgga actgacgagt tcgagacacc    900
cggccgcaac cctgggagac gtcccaggga cttcggggggc cattttttgtg gcccggccag    960
agtccaacca tcccgatcgt tttgactct ttggtgcacc ccccttagag gaggggtatg   1020
tggttctggt aggagacaga gggctaaaac ggtttccgcc cccgtctgag tttttgcttt   1080
cggtttggaa ccgaagccgc gccgcgcgtc ttgtctgctg cagcatcgtt ctgtgttgtc   1140
tctgtttgac tgttttttctg tatttgtctg aaaacatggg ccaggctgtt accaccccct   1200
taaggtagat gcatctacct taagtttgac tttagaccac tggaaggatg tcgaacggac   1260
agcccacaac ctgtcggtag aggttagaaa aaggcgctgg gttacattct gctctgcaga   1320
atggccaacc ttcaacgtcg gatggccacg agacggcact tttaacccag acattattac   1380
acaggttaag atcaaggtct tctcacctgg cccacatgga catccggatc aggtccccta   1440
catcgtgacc tgggaagcta tagcagtaga ccccccctccc tgggtcagac ccttcgtgca   1500
ccctaaacct cccctctctc ttccccttc agcccctct ctcccacctg aaccccact   1560
ctcgaccccg ccccagtcct ccctctatcc ggctctcact tctcctttaa acaccaaacc   1620
taggcctcaa gtccttcctg atagcggagg accactcatt gatctactca cggaggaccc   1680
tccgccttac cgggacccag ggccacccctc tcctgacggg aacggcgata gcggagaagt   1740
ggcccctaca gaaggagccc ctgaccccttc cccaatggta tcccgcctgc ggggaagaaa   1800
agaacccccc gtggcggatt ctactacctc tcaggcgttc cccttcgcc tgggagggaa   1860
tggacagtat caatactggc cattttcctc ctctgacctc tataactgga aaaataacaa   1920
cccctctttc tccgaggacc cagctaaatt gacagctttg atcgagtccg ttctccttac   1980
tcatcagccc acttgggatg actgccaaca gctattaggg accctgctga cgggagaaga   2040
aaaacagcga gtgctcctag aggcccgaaa ggcggttcga ggggaggacg gacgcccaac   2100
tcagggggat cctctagagt cgagcatatg aaatcttata tggggcaccc ccgccccttg   2160
```

```
taaacttccc tgatcctgac atggcaaagg ttactcataa cccctctctc caagcccatt    2220
tacaggcact ctacctggtc cagcacgaag tctggagacc gttggcggca gcttaccaag    2280
aacaactgga ccggccggta gtgcctcacc ctttccgagt cggtgacaca gtgtgggtcc    2340
gcagacacca aactaaaaat ctagaacccc gctggaaagg accttatacc gtcctactga    2400
ctaccccccac cgctctcaaa gtggacggca ttgcagcgtg gatccacgct gcccacgtat   2460
aggctgccga caccaggatt gagccaccat cggagccacc atggcagtca gtcagtctcg    2520
aggcttagcc tgatagccgc agtaacgcca ttttgcaagg catggaaaaa taccaaacca    2580
agaatagaga agttcagatc aagggcgggt acacgaaaac agctaacgtt gggccaaaca    2640
ggatatctgc ggtgagcagt ttcggccccg gcccgggggcc aagaacagat ggtcaccgcg   2700
gttcggcccc ggcccggggc caagaacaga tggtccccag atatggccca accctcagca    2760
gtttcttaag acccatcaga tgtttccagg ctcccccaag gacctgaaat gaccctgtgc    2820
cttatttgaa ttaaccaatc agcctgcttc tcgcttctgt tcgcgcgctt ctgcttcccg    2880
agctctataa aagagctcac aacccctcac tcggcgcgtc gcgcgcggga tccaccggtc    2940
gccaccatgg tgagcaaggg cgaggagctg ttcaccgggg tggtgcccat cctggtcgag    3000
ctggacggcg acgtaaacgg ccacaagttc agcgtgtccg gcgagggcga gggcgatgcc    3060
acctacggca agctgaccct gaagttcatc tgcaccaccg gcaagctgcc cgtgccctgg    3120
cccacccctcg tgaccaccct gacctacggc gtgcagtgct tcagccgcta ccccgaccac   3180
atgaagcagc acgacttctt caagtccgcc atgcccgaag ctacgtcca ggagcgcacc     3240
atcttcttca aggacgacgg caactacaag acccgcgccg aggtgaagtt cgagggcgac    3300
accctggtga accgcatcga gctgaagggc atcgacttca aggaggacgg caacatcctg    3360
gggcacaagc tggagtacaa ctacaacagc cacaacgtct atatcatggc cgacaagcag    3420
aagaacggca tcaaggtgaa cttcaagatc cgccacaaca tcgaggacgg cagcgtgcag    3480
ctcgccgacc actaccagca gaacaccccc atcggcgacg gccccgtgct gctgcccgac    3540
aaccactacc tgagcaccca gtccgccctg agcaaagacc ccaacgagaa gcgcgatcac    3600
atggtcctgc tggagttcgt gaccgccgcc gggatcactc tcggcatgga cgagctgtac    3660
aagtaaagct cgagaaggaa aaaagcggcc gcaatgaaag accccaccaa attgcttacg    3720
gatccccccag ggatgtaatt acgtccctcc cccgctaggg ggcagcaccc aggcctgcac   3780
tgccgcctgc cggcagggggt ccagtcccca gggatgtaat tatgtccctc cccgctagg   3840
gggcagcacc caggcctgca ctgccgcctg ccggcagggg tccagtcccc agggatgtaa    3900
ttacgtccct cccccgctag ggggcagcac ccaggcctgc actgccgcct gccggcaggg    3960
gtccagtccc cggggagctc caatcgatgc gccagtcctc cgatagactg agtcgcccgg    4020
gtacccgtgt atccaataaa tcctcttgct gttgcatccg actcgtggtc tcgctgttcc    4080
ttgggagggt ctcctcagag tgattgacta cccgtctcgg gggtctttca ttagatcttg    4140
gcgtaatcat ggtcatagct gtttcctgtg tgaaattgtt atccgctcac aattccacac    4200
aacatacgag ccggaagcat aaagtgtaaa gcctggggtg cctaatgagt gagctaactc    4260
acattaattg cgttgcgctc actgcccgct ttccagtcgg gaaacctgtc gtgccagctg    4320
cattaatgaa tcggccaacg cgcggggaga ggcggtttgc gtattgggcg ctcttccgct    4380
tcctcgctca ctgactcgct gcgctcggtc gttcggctgc ggcgagcggt atcagctcac    4440
tcaaaggcgg taatacggtt atccacagaa tcaggggata acgcaggaaa gaacatgtga    4500
```

```
gcaaaaggcc agcaaaaggc caggaaccgt aaaaaggccg cgttgctggc gttttttccat    4560
aggctccgcc cccctgacga gcatcacaaa aatcgacgct caagtcagag gtggcgaaac    4620
ccgacaggac tataaagata ccaggcgttt ccccctggaa gctccctcgt gcgctctcct    4680
gttccgaccc tgccgcttac cggatacctg tccgcctttc tcccttcggg aagcgtggcg    4740
ctttctcata gctcacgctg taggtatctc agttcggtgt aggtcgttcg ctccaagctg    4800
ggctgtgtgc acgaaccccc cgttcagccc gaccgctgcg ccttatccgg taactatcgt    4860
cttgagtcca acccggtaag acacgactta tcgccactgg cagcagccac tggtaacagg    4920
attagcagag cgaggtatgt aggcggtgct acagagttct tgaagtggtg cctaactac     4980
ggctacacta gaaggacagt atttggtatc tgcgctctgc tgaagccagt taccttcgga    5040
aaaagagttg gtagctcttg atccggcaaa caaaccaccg ctggtagcgg tggtttttt     5100
gtttgcaagc agcagattac gcgcagaaaa aaaggatctc aagaagatcc tttgatcttt    5160
tctacggggt ctgacgctca gtggaacgaa aactcacgtt aagggatttt ggtcatgaga    5220
ttatcaaaaa ggatcttcac ctagatcctt ttaaattaaa aatgaagttt taaatcaatc    5280
taaagtatat atgagtaaac ttggtctgac agttaccaat gcttaatcag tgaggcacct    5340
atctcagcga tctgtctatt tcgttcatcc atagttgcct gactccccgt cgtgtagata    5400
actacgatac gggagggctt accatctggc cccagtgctg caatgatacc gcgagaccca    5460
cgctcaccgg ctccagattt atcagcaata accagccag ccggaagggc cgagcgcaga    5520
agtggtcctg caactttatc cgcctccatc cagtctatta attgttgccg ggaagctaga    5580
gtaagtagtt cgccagttaa tagtttgcgc aacgttgttg ccattgctac aggcatcgtg    5640
gtgtcacgct cgtcgtttgg tatggcttca ttcagctccg gttcccaacg atcaaggcga    5700
gttacatgat cccccatgtt gtgcaaaaaa gcggttagct ccttcggtcc tccgatcgtt    5760
gtcagaagta agttggccgc agtgttatca ctcatggtta tggcagcact gcataattct    5820
cttactgtca tgccatccgt aagatgcttt tctgtgactg gtgagtactc aaccaagtca    5880
ttctgagaat agtgtatgcg cgaccgagt tgctcttgcc cggcgtcaat acgggataat    5940
accgcgccac atagcagaac tttaaaagtg ctcatcattg gaaaacgttc ttcggggcga    6000
aaactctcaa ggatcttacc gctgttgaga tccagttcga tgtaacccac tcgtgcaccc    6060
aactgatctt cagcatcttt tactttcacc agcgtttctg ggtgagcaaa aacaggaagg    6120
caaaatgccg caaaaaaggg aataagggcg acacggaaat gttgaatact catactcttc    6180
cttttttcaat attattgaag catttatcag ggttattgtc tcatgagcgg atacatattt    6240
gaatgtattt agaaaaataa acaaataggg gttccgcgca catttccccg aaaagtgcca    6300
cctgacgtct aagaaaccat tattatcatg acattaacct ataaaaatag gcgtatcacg    6360
aggccctttc gtctcgcgcg tttcggtgat gacggtgaaa acctctgaca catgcagctc    6420
ccggagacgg tcagcttg tctgtaagcg gatgccggga gcagacaagc ccgtcagggc    6480
gcgtcagcgg gtgttggcgg gtgtcgggc tggcttaact atgcggcatc agagcagatt    6540
gtactgagag tgcaccatat gcggtgtgaa ataccgcaca gatgcgtaag gagaaaatac    6600
cgcatcaggc gccattcgcc attcaggctg cgcaactgtt gggaagggcg atcggtgcgg    6660
gcctcttcgc tattacgcca gctggcgaaa gggggatgtg ctgcaaggcg attaagttgg    6720
gtaacgccag ggttttccca gtcacgacgt tgtaaaacga cggccagt             6768
```

<210> SEQ ID NO 36
<211> LENGTH: 7396

<212> TYPE: DNA
<213> ORGANISM: Artificial Sequence
<220> FEATURE:
<223> OTHER INFORMATION: Description of Artificial Sequence: Synthetic P7 polynucleotide

<400> SEQUENCE: 36

```
ggccgcaagt cgacctgcag gcatgcacag atcccgccta gttcaatttg ttaaagacag      60
gatctcagta gtccaggctt tagtcctgac tcaacaatac caccagctaa aaccactaga     120
atacgagcca caataaataa aagattttat ttagtttcca gaaaaagggg ggaatgaaga     180
ccccaccaaa ttgcttagcc tgatagccgc agtaacgcca ttttgcaagg catggaaaaa     240
taccaaacca agaatagaga agttcagatc aagggcgggt acacgaaaac agctaacgtt     300
gggccaaaca ggatatctgc ggtgagcagt ttcggccccg gcccgggcc aagaacagat      360
ggtcaccgcg gttcggcccc ggcccggggc caagaacaga tggtccccag atatggccca     420
accctcagca gtttcttaag acccatcaga tgtttccagg ctcccccaag gacctgaaat     480
gaccctgtgc cttatttgaa ttaaccaatc agcctgcttc tcgcttctgt tcgcgcgctt     540
ctgcttcccg agctctataa aagagctcac aacccctcac tcggcgcgcc agtcctccga     600
tagactgagt cgcccgggta cccgtgtatc caataaatcc tcttgctgtt gcatccgact     660
cgtggtctcg ctgttccttg ggagggtctc ctcagagtga ttgactaccc gtctcggggg     720
tctttcattt gggggctcgt ccgggatctg agaccccctg cccagggacc accgacccac     780
caccgggagg taagctggcc agcaattgtt ctgtgtctgt ccattgtcct gtgtctttga     840
ttgattttat gcgcctgtgt ctgtactagt tggccgacta gattggtatc tggcggatca     900
gatcttggcg taatcatggt catagctgtt tcctgtgtga aattgttatc cgctcacaat     960
tccacacaac atacgagccg gaagcataaa gtgtaaagcc tggggtgcct aatgagtgag    1020
ctaactcaca ttaattgcgt tgcgctcact gcccgctttc cagtcgggaa acctgtcgtg    1080
ccagctgcat taatgaatcg gccaacgcgc ggggagaggc ggtttgcgta ttgggcgctc    1140
ttccgcttcc tcgctcactg actcgctgcg ctcggtcgtt cggctgcggc gagcggtatc    1200
agctcactca aaggcggtaa tacggttatc cacagaatca ggggataacg caggaaagaa    1260
catgtgagca aaaggccagc aaaaggccag gaaccgtaaa aaggccgcgt tgctggcgtt    1320
tttccatagg ctccgccccc ctgacgagca tcacaaaaat cgacgctcaa gtcagaggtg    1380
gcgaaacccg acaggactat aaagatacca ggcgtttccc cctggaagct ccctcgtgcg    1440
ctctcctgtt ccgaccctgc cgcttaccgg atacctgtcc gcctttctcc cttcgggaag    1500
cgtggcgctt tctcatagct cacgctgtag gtatctcagt tcggtgtagg tcgttcgctc    1560
caagctgggc tgtgtgcacg aaccccccgt tcagcccgac cgctgcgcct tatccggtaa    1620
ctatcgtctt gagtccaacc cggtaagaca cgacttatcg ccactggcag cagccactgg    1680
taacaggatt agcagagcga ggtatgtagg cggtgctaca gagttcttga agtggtggcc    1740
taactacggc tacactagaa ggacagtatt tggtatctgc gctctgctga gccagttac     1800
cttcggaaaa agagttggta gctcttgatc cggcaaacaa accaccgctg gtagcggtgg    1860
tttttttgtt tgcaagcagc agattacgcg cagaaaaaaa ggatctcaag aagatccttt    1920
gatcttttct acggggtctg acgctcagtg gaacgaaaac tcacgttaag ggattttggt    1980
catgagatta tcaaaaagga tcttcaccta gatccttta aattaaaaat gaagttttaa     2040
atcaatctaa agtatatatg agtaaacttg gtctgacagt taccaatgct taatcagtga    2100
ggcacctatc tcagcgatct gtctatttcg ttcatccata gttgcctgac tccccgtcgt    2160
```

```
gtagataact acgatacggg agggcttacc atctggcccc agtgctgcaa tgataccgcg   2220
agacccacgc tcaccggctc cagatttatc agcaataaac cagccagccg aagggccga    2280 gcgcagaagt ggtcctgcaa ctttatccgc ctccatccag tctattaatt gttgccggga   2340
agctagagta agtagttcgc cagttaatag tttgcgcaac gttgttgcca ttgctacagg   2400
catcgtggtg tcacgctcgt cgtttggtat ggcttcattc agctccggtt cccaacgatc   2460
aaggcgagtt acatgatccc ccatgttgtg caaaaaagcg gttagctcct tcggtcctcc   2520
gatcgttgtc agaagtaagt tggccgcagt gttatcactc atggttatgg cagcactgca   2580
taattctctt actgtcatgc catccgtaag atgcttttct gtgactggtg agtactcaac   2640
caagtcattc tgagaatagt gtatgcggcg accgagttgc tcttgcccgg cgtcaatacg   2700
ggataatacc gcgccacata gcagaacttt aaaagtgctc atcattggaa aacgttcttc   2760
ggggcgaaaa ctctcaagga tcttaccgct gttgagatcc agttcgatgt aacccactcg   2820
tgcacccaac tgatcttcag catcttttac tttcaccagc gtttctgggt gagcaaaaac   2880
aggaaggcaa aatgccgcaa aaaagggaat aagggcgaca cggaaatgtt gaatactcat   2940
actcttcctt tttcaatatt attgaagcat ttatcagggt tattgtctca tgagcggata   3000
catatttgaa tgtatttaga aaataaaca aatagggg tt ccgcgcacat ttccccgaaa   3060
agtgccacct gacgtctaag aaaccattat tatcatgaca ttaacctata aaaataggcg   3120
tatcacgagg ccctttcgtc tcgcgcgttt cggtgatgac ggtgaaaacc tctgacacat   3180
gcagctcccg gagacggtca cagcttgtct gtaagcggat gccgggagca gacaagcccg   3240
tcagggcgcg tcagcgggtg ttggcgggtg tcggggctgg cttaactatg cggcatcaga   3300
gcagattgta ctgagagtgc accatatgcg gtgtgaaata ccgcacagat gcgtaaggag   3360
aaaataccgc atcaggcgcc attcgccatt caggctgcgc aactgttggg aagggcgatc   3420
ggtgcgggcc tcttcgctat tacgccagct ggcgaaaggg ggatgtgctg caaggcgatt   3480
aagttgggta acgccagggt tttcccagtc acgacgttgt aaaacgacgg ccagtgaatt   3540
cgattagttc aatttgttaa agacaggatc tcagtagtcc aggctttagt cctgactcaa   3600
caataccacc agctaaaacc actagaatac gagccacaat aaataaaaga ttttatttag   3660
tttccagaaa aagggggggaa tgaaagaccc caccaaattg cttagcctga tagccgcagt   3720
aacgccattt tgcaaggcat ggaaaaatac caaaccaaga atagagaagt tcagatcaag   3780
ggcgggtaca cgaaaacagc taacgttggg ccaaacagga tatctgcggt gagcagtttc   3840
ggccccggcc cggggccaag aacagatggt caccgcggtt cggccccggc ccggggccaa   3900
gaacagatgg tccccagata tggcccaacc ctcagcagtt tcttaagacc catcagatgt   3960
ttccaggctc cccaaggac ctgaaatgac cctgtgcctt atttgaatta accaatcagc   4020
ctgcttctcg cttctgttcg cgcgcttctg cttcccgagc tctataaaag agctcacaac   4080
ccctcactcg gcgcgccagt cctccgatag actgagtcgc ccgggtaccc gtgtatccaa   4140
taaatcctct tgctgttgca tccgactcgt ggtctcgctg ttccttggga gggtctcctc   4200
agagtgattg actacccgtc tcgggggtct ttcatttggg ggctcgtccg ggatctggag   4260
acccctgccc agggaccacc gacccaccac cgggaggtaa gctggccagc aattgttctg   4320
tgtctgtcca ttgtcctgtg tctttgattg attttatgcg cctgtgtctg tactagttgg   4380
ccgactagat tggtatctgg cggatccgtg gtggaactga cgagttcgag cacccggcc   4440 gcaaccctgg gagacgtccc agggacttcg ggggccattt ttgtggcccg gccagagtcc   4500
```

```
aaccatcccg atcgttttgg actctttggt gcaccccct tagaggaggg gtatgtggtt    4560
ctggtaggag acagagggct aaaacggttt ccgcccccgt ctgagttttt gctttcggtt    4620
tggaaccgaa gccgcgccgc gcgtcttgtc tgctgcagca tcgttctgtg ttgtctctgt    4680
ttgactgttt ttctgtattt gtctgaaaac atgggccagg ctgttaccac cccccttaagg   4740 tagatgcatc taccttaagt ttgactttag accactggaa ggatgtcgaa cggacagccc    4800
acaacctgtc ggtagaggtt agaaaaaggc gctgggttac attctgctct gcagaatggc    4860
caaccttcaa cgtcggatgg ccacgagacg gcacttttaa cccagacatt attacacagg    4920
ttaagatcaa ggtcttctca cctggcccac atggacatcc ggatcaggtc ccctacatcg    4980
tgacctggga agctatagca gtagaccccc ctccctgggt cagacccttc gtgcaccta     5040 aacctcccct ctctcttccc ccttcagccc ctctctccc acctgaaccc ccactctcga     5100
ccccgcccca gtcctccctc tatccggctc tcacttctcc tttaaacacc aaacctaggc    5160
ctcaagtcct tcctgatagc ggaggaccac tcattgatct actcacggag gaccctccgc    5220
cttaccggga cccagggcca ccctctcctg acgggaacgg cgatagcgga gaagtggccc    5280
ctacagaagg agccctgac ccttccccaa tggtatcccg cctgcgggga agaaaagaac      5340
cccccgtggc ggattctact acctctcagg cgttcccct tcgcctggga gggaatggac     5400
agtatcaata ctggccattt tcctcctctg acctctataa ctggaaaaat aacaacccct    5460 cttctccga ggacccagct aaattgacag ctttgatcga gtccgttctc cttactcatc      5520
agcccacttg ggatgactgc caacagctat tagggaccct gctgacggga gaagaaaaac    5580
agcgagtgct cctagaggcc cgaaaggcgg ttcgaggga ggacggacgc ccaactcagg     5640
gggatcctct agagtcgagc atatgaaatc ttatatgggg caccccgcc ccttgtaaac      5700 ttccctgatc ctgacatggc aaaggttact cataacccct ctctccaagc ccatttacag    5760
gcactctacc tggtccagca cgaagtctgg agaccgttgg cggcagctta ccaagaacaa    5820
ctggaccggc cggtagtgcc tcacccttc cgagtcggtg acacagtgtg ggtccgcaga     5880
caccaaacta aaaatctaga accccgctgg aaaggacctt ataccgtcct actgactacc    5940
cccaccgctc tcaaagtgga cggcattgca gcgtggatcc acgctgccca cgtataggct    6000
gccgacacca ggattgagcc accatcggag ccaccatggc agtcagtcag tctcgaggct    6060
tagcctgata gccgcagtaa cgccattttg caaggcatgg aaaaatacca aaccaagaat    6120
agagaagttc agatcaaggg cgggtacacg aaaacagcta acgttgggcc aaacaggata    6180
tctgcggtga gcagtttcgg ccccggcccg gggccaagaa cagatggtca ccgcggttcg    6240
gccccggccc ggggccaaga acagatggtc cccagatatg gcccaaccct cagcagtttc    6300
ttaagaccca tcagatgttt ccaggctccc ccaaggacct gaaatgaccc tgtgccttat    6360
ttgaattaac caatcagcct gcttctcgct tctgttcgcg cgcttctgct tcccgagctc    6420
tataaaagag ctcacaaccc ctcactcggc gcgtcgcgcg cgggatccac cggtcgccac    6480
catggtgagc aagggcgagg agctgttcac cggggtggtg cccatcctgg tcgagctgga    6540
cggcgacgta aacggccaca gttcagcgt gtccggcgag ggcgagggcg atgccaccta    6600
cggcaagctg accctgaagt tcatctgcac caccggcaag ctgcccgtgc cctggccac    6660 cctcgtgacc accctgacct acggcgtgca gtgcttcagc cgctacccg accacatgaa    6720 gcagcacgac ttcttcaagt ccgccatgcc cgaaggctac gtccaggagc gcaccatctt    6780
cttcaaggac gacggcaact acaagacccg cgccgaggtg aagttcgagg gcgacaccct    6840
ggtgaaccgc atcgagctga agggcatcga cttcaaggag gacggcaaca tcctggggca    6900
```

```
caagctggag tacaactaca acagccacaa cgtctatatc atggccgaca agcagaagaa      6960
cggcatcaag gtgaacttca agatccgcca caacatcgag gacggcagcg tgcagctcgc      7020
cgaccactac cagcagaaca cccccatcgg cgacggcccc gtgctgctgc ccgacaacca      7080
ctacctgagc acccagtccg ccctgagcaa agacccaaac gagaagcgcg atcacatggt      7140
cctgctggag ttcgtgaccg ccgccgggat cactctcggc atggacgagc tgtacaagta      7200
aagctcgaga aggaaaaaag cggccgcaag tcgacctgca ggcatgcaca gatcccgcct      7260
agttcaattt gttaaagaca ggatctcagt agtccaggct ttagtcctga ctcaacaata      7320
ccaccagcta aaaccactag aatacgagcc acaataaata aaagatttta tttagtttcc      7380
agaaaaaggg gggttc                                                     7396

<210> SEQ ID NO 37
<211> LENGTH: 6942
<212> TYPE: DNA
<213> ORGANISM: Artificial Sequence
<220> FEATURE:
<223> OTHER INFORMATION: Description of Artificial Sequence: Synthetic
      P11 polynucleotide

<400> SEQUENCE: 37
gaattcgatt agttcaattt gttaaagaca ggatctcagt agtccaggct ttagtcctga        60
ctcaacaata ccaccagcta aaaccactag aatacgagcc acaataaata aaagattta       120 tttagtttcc agaaaaaggg gggaatgaaa gaccccacca aattgcttag cctgatagcc      180
gcagtaacgc cattttgcaa ggcatggaaa ataccaaac caagaataga gaagttcaga       240
tcaagggcgg gtacacgaaa acagctaacg ttgggccaaa caggatatct gcggtgagca      300
gtttcggccc cggcccgggg ccaagaacag atggtcaccg cggttcggcc ccggcccggg      360
gccaagaaca gatggtcccc agatatggcc caaccctcag cagtttctta agacccatca      420
gatgtttcca ggctccccca aggacctgaa atgaccctgt gccttatttg aattaaccaa      480
tcagcctgct tctcgcttct gttcgcgcgc ttctgcttcc cgagctctat aaaagagctc      540
acaacccctc actcggcgcg ccagtcctcc gatagactga gtcgcccggg tacccgtgta      600
tccaataaat cctcttgctg ttgcatccga ctcgtggtct cgctgttcct gggagggtc      660 tcctcagagt gattgactac ccgtctcggg ggtctttcat ttgggggctc gtccgggatc      720
tggagacccc tgcccaggga ccaccgaccc accaccggga ggtaagctgg ccagcaattg      780
ttctgtgtct gtccattgtc ctgtgtcttt gattgatttt atgcgcctgt gtctgtacta      840
gttggccgac tagattggta tctggcggat ccgtggtgga actgacgagt tcgagacacc      900
cggccgcaac cctgggagac gtcccaggga cttcggggc cattttgtg gcccggccag       960 agtccaacca tcccgatcgt tttggactct tggtgcacc cccttagag gagggtatg       1020 tggttctggt aggagacaga gggctaaaac ggtttccgcc cccgtctgag ttttgctt      1080 cggtttggaa ccgaagccgc gccgcgcgtc ttgtctgctg cagcatcgtt ctgtgttgtc      1140
tctgtttgac tgttttctg tatttgtctg aaaacatggg ccaggctgtt accaccccct      1200
taaggtagat gcatctacct taagtttgac tttagaccac tggaaggatg tcgaacggac      1260
agcccacaac ctgtcggtag aggttagaaa aaggcgctgg gttacattct gctctgcaga      1320
atggccaacc ttcaacgtcg gatggccacg agacggcact tttaacccag acattattac      1380
acaggttaag atcaaggtct tctcacctgg cccacatgga catccggatc aggtcccta      1440 catcgtgacc tgggaagcta tagcagtaga ccccctccc tgggtcagac ccttcgtgca      1500
```

```
ccctaaacct cccctctctc ttccccttc agccccctct ctcccacctg aacccccact    1560 ctcgacccg ccccagtcct ccctctatcc ggctctcact tctcctttaa acaccaaacc    1620
taggcctcaa gtccttcctg atagcggagg accactcatt gatctactca cggaggaccc    1680
tccgccttac cgggacccag ggccaccctc tcctgacggg aacggcgata gcggagaagt    1740 ggccctaca gaaggagccc ctgacccttc cccaatggta tcccgcctgc ggggaagaaa     1800
agaacccccc gtggcggatt ctactacctc tcaggcgttc ccccttcgcc tgggagggaa    1860
tggacagtat caatactggc cattttcctc ctctgacctc tataactgga aaaataacaa    1920
cccctctttc tccgaggacc cagctaaatt gacagctttg atcgagtccg ttctccttac    1980
tcatcagccc acttgggatg actgccaaca gctattaggg accctgctga cgggagaaga    2040
aaaacagcga gtgctcctag aggcccgaaa ggcggttcga ggggaggacg gacgcccaac    2100
tcagggggat cctctagagt cgagcatatg aaatcttata tggggcaccc ccgccccttg    2160
taaacttccc tgatcctgac atggcaaagg ttactcataa cccctctctc caagcccatt    2220
tacaggcact ctacctggtc cagcacgaag tctggagacc gttggcggca gcttaccaag    2280
aacaactgga ccggccggta gtgcctcacc ctttccgagt cggtgacaca gtgtgggtcc    2340
gcagacacca aactaaaaat ctagaacccc gctggaaagg accttatacc gtcctactga    2400 ctaccccac cgctctcaaa gtggacggca ttgcagcgtg gatccacgct gcccacgtat     2460
aggctgccga caccaggatt gagccaccat cggagccacc atggcagtca gtcagtctcg    2520
aggcttagcc tgatagccgc agtaacgcca ttttgcaagg catggaaaaa taccaaacca    2580
agaatagaga agttcagatc aagggcgggt acacgaaaac agctaacgtt gggccaaaca    2640
ggatatctgc ggtgagcagt ttcggcccg gccgggggcc aagaacagat ggtcaccgcg      2700
gttcggcccc ggcccggggc caagaacaga tggtccccag atatggccca accctcagca    2760
gtttcttaag acccatcaga tgtttccagg ctcccccaag gacctgaaat gaccctgtgc    2820
cttatttgaa ttaaccaatc agcctgcttc tcgcttctgt tcgcgcgctt ctgcttcccg    2880
agctctataa aagagctcac aacccctcac tcggcgcgtc gcgcgcggga tccaccggtc    2940
gccaccatgg tgagcaaggg cgaggagctg ttcaccgggg tggtgcccat cctggtcgag    3000
ctggacggcg acgtaaacgg ccacaagttc agcgtgtccg gcgagggcga gggcgatgcc    3060
acctacggca agctgaccct gaagttcatc tgcaccaccg gcaagctgcc cgtgccctgg    3120 cccacccctcg tgaccaccct gacctacggc gtgcagtgct tcagccgcta ccccgaccac    3180
atgaagcagc acgacttctt caagtccgcc atgcccgaag ctacgtcca ggagcgcacc     3240 atcttcttca aggacgacgg caactacaag acccgcgccg aggtgaagtt cgagggcgac    3300
accctggtga accgcatcga gctgaagggc atcgacttca aggaggacgg caacatcctg    3360
gggcacaagc tggagtacaa ctacaacagc cacaacgtct atatcatggc cgacaagcag    3420
aagaacggca tcaaggtgaa cttcaagatc cgccacaaca tcgaggacgg cagcgtgcag    3480
ctcgccgacc actaccagca gaacaccccc atcggcgacg ccccgtgct gctgcccgac     3540 aaccactacc tgagcaccca gtccgccctg agcaaagacc ccaacgagaa gcgcgatcac    3600
atggtcctgc tggagttcgt gaccgccgcc gggatcactc tcggcatgga cgagctgtac    3660
aagtaaagct cgagaaggaa aaaagcggcc gcaagtcgac ctgcaggcat gcacagatcc    3720
cgcctagttc aatttgttaa agacaggatc tcagtagtcc aggctttagt cctgactcaa    3780
caataccacc agctaaaacc actagaatac gagccacaat aaataaaaga ttttatttag    3840
```

```
tttccagaaa aagggggttt cggccgaatg aaagacccca ccaaattgct tacggatccc   3900
ccagggatgt aattacgtcc ctcccccgct aggggggcagc acccaggcct gcactgccgc   3960
ctgccggcag gggtccagtc cccagggatg taattatgtc cctcccccgc tagggggcag   4020
cacccaggcc tgcactgccg cctgccggca ggggtccagt cccagggat gtaattacgt   4080
ccctcccccg ctaggggggca gcacccaggc ctgcactgcc gcctgccggc aggggtccag   4140
tccccgggga gctccaatcg atgcgccagt cctccgatag actgagtcgc ccgggtaccc   4200
gtgtatccaa taaatcctct tgctgttgca tccgactcgt ggtctcgctg ttccttggga   4260
gggtctcctc agagtgattg actacccgtc tcggggtct ttcattagat cttggcgtaa   4320
tcatggtcat agctgtttcc tgtgtgaaat tgttatccgc tcacaattcc acacaacata   4380
cgagccggaa gcataaagtg taaagcctgg ggtgcctaat gagtgagcta actcacatta   4440
attgcgttgc gctcactgcc cgctttccag tcgggaaacc tgtcgtgcca gctgcattaa   4500
tgaatcggcc aacgcgcggg gagaggcggt ttgcgtattg ggcgctcttc cgcttcctcg   4560
ctcactgact cgctgcgctc ggtcgttcgg ctgcggcgag cggtatcagc tcactcaaag   4620
gcggtaatac ggttatccac agaatcaggg gataacgcag gaaagaacat gtgagcaaaa   4680
ggccagcaaa aggccaggaa ccgtaaaaag gccgcgttgc tggcgttttt ccataggctc   4740
cgcccccctg acgagcatca caaaaatcga cgctcaagtc agaggtggcg aaacccgaca   4800
ggactataaa gataccaggc gtttccccct ggaagctccc tcgtgcgctc tcctgttccg   4860
accctgccgc ttaccggata cctgtccgcc tttctccctt cgggaagcgt ggcgctttct   4920
catagctcac gctgtaggta tctcagttcg gtgtaggtcg ttcgctccaa gctgggctgt   4980
gtgcacgaac cccccgttca gcccgaccgc tgcgccttat ccggtaacta tcgtcttgag   5040
tccaacccgg taagacacga cttatcgcca ctggcagcag ccactggtaa caggattagc   5100
agagcgaggt atgtaggcgg tgctacagag ttcttgaagt ggtggcctaa ctacggctac   5160
actagaagga cagtatttgg tatctgcgct ctgctgaagc cagttacctt cggaaaaaga   5220
gttggtagct cttgatccgg caaacaaacc accgctggta gcggtggttt ttttgtttgc   5280
aagcagcaga ttacgcgcag aaaaaaagga tctcaagaag atcctttgat cttttctacg   5340
gggtctgacg ctcagtggaa cgaaaactca cgttaaggga ttttggtcat gagattatca   5400
aaaaggatct tcacctagat cctttttaaat taaaaatgaa gttttaaatc aatctaaagt   5460
atatatgagt aaacttggtc tgacagttac caatgcttaa tcagtgaggc acctatctca   5520
gcgatctgtc tatttcgttc atccatagtt gcctgactcc ccgtcgtgta gataactacg   5580
atacgggagg gcttaccatc tggccccagt gctgcaatga taccgcgaga cccacgctca   5640
ccggctccag atttatcagc aataaaccag ccagccggaa gggccgagcg cagaagtggt   5700
cctgcaactt tatccgcctc catccagtct attaattgtt gccgggaagc tagagtaagt   5760
agttcgccag ttaatagttt gcgcaacgtt gttgccattg ctacaggcat cgtggtgtca   5820
cgctcgtcgt ttggtatggc ttcattcagc tccggttccc aacgatcaag gcgagttaca   5880
tgatccccca tgttgtgcaa aaaagcggtt agctccttcg gtcctccgat cgttgtcaga   5940
agtaagttgg ccgcagtgtt atcactcatg gttatggcag cactgcataa ttctcttact   6000
gtcatgccat ccgtaagatg cttttctgtg actggtgagt actcaaccaa gtcattctga   6060
gaatagtgta tgcggcgacc gagttgctct tgcccggcgt caatacggga taataccgcg   6120
ccacatagca gaactttaaa agtgctcatc attggaaaac gttcttcggg gcgaaaactc   6180
tcaaggatct taccgctgtt gagatccagt tcgatgtaac ccactcgtgc acccaactga   6240
```

```
tcttcagcat cttttacttt caccagcgtt tctgggtgag caaaaacagg aaggcaaaat    6300
gccgcaaaaa agggaataag ggcgacacgg aaatgttgaa tactctatact cttccttttt    6360 caatattatt gaagcattta tcagggttat tgtctcatga gcggatacat atttgaatgt    6420
atttagaaaa ataaacaaat aggggttccg cgcacatttc cccgaaaagt gccacctgac    6480
gtctaagaaa ccattattat catgacatta acctataaaa ataggcgtat cacgaggccc    6540
tttcgtctcg cgcgtttcgg tgatgacggt gaaaacctct gacacatgca gctcccggag    6600
acggtcacag cttgtctgta agcggatgcc gggagcagac aagcccgtca gggcgcgtca    6660
gcgggtgttg gcgggtgtcg ggctggctt aactatgcgg catcagagca gattgtactg    6720
agagtgcacc atatgcggtg tgaaataccg cacagatgcg taaggagaaa ataccgcatc    6780
aggcgccatt cgccattcag gctgcgcaac tgttgggaag ggcgatcggt gcgggcctct    6840
tcgctattac gccagctggc gaaaggggga tgtgctgcaa ggcgattaag ttgggtaacg    6900
ccagggtttt cccagtcacg acgttgtaaa acgacggcca gt    6942
```

<210> SEQ ID NO 38
<211> LENGTH: 6837
<212> TYPE: DNA
<213> ORGANISM: Artificial Sequence
<220> FEATURE:
<223> OTHER INFORMATION: Description of Artificial Sequence: Synthetic
      P19 polynucleotide

<400> SEQUENCE: 38

```
gaattcgatt agttcaattt gttaaagaca ggatctcagt agtccaggct ttagtcctga     60
ctcaacaata ccaccagcta aaaccactag aatacgagcc acaataaata aaagatttta    120 tttagttttcc agaaaaaggg gggaatgaaa gaccccacca aattgcttag cctgatagcc    180
gcagtaacgc cattttgcaa ggcatggaaa ataccaaac caagaataga gaagttcaga    240
tcaagggcgg gtacacgaaa acagctaacg ttgggccaaa caggatatct gcggtgagca    300
gtttcggccc cggcccgggg ccaagaacag atggtcaccg cggttcggcc ccggcccggg    360
gccaagaaca gatggtcccc agatatggcc caaccctcag cagtttctta agacccatca    420
gatgtttcca ggctccccca aggacctgaa atgaccctgt gccttatttg aattaaccaa    480
tcagcctgct tctcgcttct gttcgcgcgc ttctgcttcc cgagctctat aaaagagctc    540 acaaccctc actcggcgcg ccagtcctcc gatagactga gtcgcccggg tacccgtgta    600
tccaataaat cctcttgctg ttgcatccga ctcgtggtct cgctgttcct gggagggtc    660 tcctcagagt gattgactac ccgtctcggg ggtctttcat ttgggggctc gtccgggatc    720
tggagacccc tgcccaggga ccaccgaccc accaccggga ggtaagctgg ccagcaattg    780
ttctgtgtct gtccattgtc ctgtgtcttt gattgatttt atgcgcctgt gtctgtacta    840
gttggccgac tagattggta tctggcggat ccgtggtgga actgacgagt tcgagacacc    900
cggccgcaac cctgggagac gtcccaggga cttcggggggc catttttgtg gcccggccag    960
agtccaacca tcccgatcgt tttggactct ttggtgcacc ccccttagag gaggggtatg   1020
tggttctggt aggagacaga gggctaaaac ggtttccgcc ccgtctgag ttttttgcttt    1080 cggtttggaa ccgaagccgc gccgcgcgtc ttgtctgctg cagcatcgtt ctgtgttgtc   1140
tctgtttgac tgttttttctg tatttgtctg aaaacatggg ccaggctgtt accacccccct   1200 taaggtagat gcatctacct taagtttgac tttagaccac tggaaggatg tcgaacggac   1260
agcccacaac ctgtcggtag aggttagaaa aaggcgctgg gttacattct gctctgcaga   1320
```

```
atggccaacc ttcaacgtcg gatggccacg agacggcact tttaacccag acattattac    1380
acaggttaag atcaaggtct tctcacctgg cccacatgga catccggatc aggtccccta    1440
catcgtgacc tgggaagcta tagcagtaga ccccccctccc tgggtcagac ccttcgtgca   1500
ccctaaacct cccctctctc ttccccttc agccccctct ctcccacctg aaccccccact    1560
ctcgaccccg ccccagtcct ccctctatcc ggctctcact tctcctttaa acaccaaacc    1620
taggcctcaa gtccttcctg atagcggagg accactcatt gatctactca cggaggaccc    1680
tccgccttac cgggacccag ggccaccctc tcctgacggg aacggcgata gcggagaagt    1740
ggccctaca gaaggagccc ctgaccccttc cccaatggta cccgcctgc ggggaagaaa     1800
agaacccccc gtggcggatt ctactacctc tcaggcgttc cccttcgcc tgggagggaa     1860
tggacagtat caatactggc catttttcctc ctctgacctc tataactgga aaataacaa    1920
cccctctttc tccgaggacc cagctaaatt gacagctttg atcgagtccg ttctccttac    1980
tcatcagccc acttgggatg actgccaaca gctattaggg accctgctga cgggagaaga    2040
aaaacagcga gtgctcctag aggcccgaaa ggcggttcga ggggaggacg gacgcccaac    2100
tcaggggat cctctagagt cgagcatatg aaatcttata tggggcaccc ccgcccctttg    2160
taaacttccc tgatcctgac atggcaaagg ttactcataa cccctctctc caagcccatt    2220
tacaggcact ctacctggtc cagcacgaag tctggagacc gttggcggca gcttaccaag    2280
aacaactgga ccggccggta gtgcctcacc cttttccgagt cggtgacaca gtgtgggtcc   2340
gcagacacca aactaaaaat ctagaacccc gctggaaagg accttatacc gtcctactga    2400
ctaccccccac cgctctcaaa gtggacggca ttgcagcgtg gatccacgct gcccacgtat    2460
aggctgccga caccaggatt gagccaccat cggagccacc atggcagtca gtcagtctcg    2520
aggcttagcc tgatagccgc agtaacgcca ttttgcaagg catggaaaaa taccaaacca    2580
agaatagaga agttcagatc aagggcgggt acacgaaaac agctaacgtt gggccaaaca    2640
ggatatctgc ggtgagcagt ttcggcccc gcccggggcc aagaacagat ggtcaccgcg    2700
gttcggcccc ggcccggggc caagaacaga tggtccccag atatggccca accctcagca    2760
gtttcttaag acccatcaga tgtttccagg ctcccccaag gacctgaaat gaccctgtgc    2820
cttatttgaa ttaaccaatc agcctgcttc tcgcttctgt tcgcgcgctt ctgcttcccg    2880
agctctataa aagagctcac aacccctcac tcggcgcgtc gcgcgcggga tccaccggtc    2940
gccaccatgg tgagcaaggg cgaggagctg ttcaccgggg tggtgcccat cctggtcgag    3000
ctggacggcg acgtaaacgg ccacaagttc agcgtgtccg gcgagggcga gggcgatgcc    3060
acctacggca agctgaccct gaagttcatc tgcaccaccg gcaagctgcc cgtgccctgg    3120
cccaccctcg tgaccaccct gacctacggc gtgcagtgct tcagccgcta ccccgaccac    3180
atgaagcagc acgacttctt caagtccgcc atgcccgaag gctacgtcca ggagcgcacc    3240
atcttcttca aggacgacgg caactacaag acccgcgccg aggtgaagtt cgagggcgac    3300
accctggtga accgcatcga gctgaagggc atcgacttca aggaggacgg caacatcctg    3360
gggcacaagc tggagtacaa ctacaacagc cacaacgtct atatcatggc cgacaagcag    3420
aagaacggca tcaaggtgaa cttcaagatc cgccacaaca tcgaggacgg cagcgtgcag    3480
ctcgccgacc actaccagca gaacaccccc atcggcgacg gccccgtgct gctgcccgac    3540
aaccactacc tgagcaccca gtccgccctg agcaaagacc ccaacgagaa gcgcgatcac    3600
atggtcctgc tggagttcgt gaccgccgcc gggatcactc tcggcatgga cgagctgtac    3660
```

```
aagtaaagct cgagaaggaa aaaagcggcc gcaagtcgac ctgcaggcat gcacagatcc   3720
cgcctagttc aatttgttaa agacaggatc tcagtagtcc aggctttagt cctgactcaa   3780
caataccacc agctaaaacc actagaatac gagccacaat aaataaaaga ttttatttag   3840
tttccagaaa aagggggggtt cggccgaatg aaagacccca ccaaattgct tacggatccc   3900
cccgcttatg gcacgttgcc aatgcttatg gcacgttgcc aatgcttatg gcacgttgcc   3960
aatgcttatg gcacgttgcc aatgcttatg gcacgttgcc aatgcttatg gcacgttgcc   4020
aatgcttatg gcacgttgcc aatgcaagct tatcgatgcg ccagtcctcc gatagactga   4080
gtcgcccggg tacccgtgta tccaataaat cctcttgctg ttgcatccga ctcgtggtct   4140
cgctgttcct tgggagggtc tcctcagagt gattgactac ccgtctcggg ggtctttcat   4200
tagatcttgg cgtaatcatg gtcatagctg tttcctgtgt gaaattgtta tccgctcaca   4260
attccacaca acatacgagc cggaagcata aagtgtaaag cctggggtgc ctaatgagtg   4320
agctaactca cattaattgc gttgcgctca ctgcccgctt tccagtcggg aaacctgtcg   4380
tgccagctgc attaatgaat cggccaacgc gcggggagag gcggtttgcg tattgggcgc   4440
tcttccgctt cctcgctcac tgactcgctg cgctcggtcg ttcggctgcg gcgagcggta   4500
tcagctcact caaaggcggt aatacggtta tccacagaat caggggataa cgcaggaaag   4560
aacatgtgag caaaaggcca gcaaaaggcc aggaaccgta aaaaggccgc gttgctggcg   4620
tttttccata ggctccgccc ccctgacgag catcacaaaa atcgacgctc aagtcagagg   4680
tggcgaaacc cgacaggact ataaagatac caggcgtttc cccctggaag ctccctcgtg   4740
cgctctcctg ttccgaccct gccgcttacc ggatacctgt ccgcctttct cccttcggga   4800
agcgtggcgc tttctcatag ctcacgctgt aggtatctca gttcggtgta ggtcgttcgc   4860
tccaagctgg gctgtgtgca cgaaccccccc gttcagcccg accgctgcgc cttatccggt   4920
aactatcgtc ttgagtccaa cccggtaaga cacgacttat cgccactggc agcagccact   4980
ggtaacagga ttagcagagc gaggtatgta ggcggtgcta cagagttctt gaagtggtgg   5040
cctaactacg gctacactag aaggacagta tttggtatct gcgctctgct gaagccagtt   5100
accttcggaa aaagagttgg tagctcttga tccggcaaac aaaccaccgc tggtagcggt   5160
ggttttttg tttgcaagca gcagattacg cgcagaaaaa aaggatctca agaagatcct   5220
ttgatctttt ctacggggtc tgacgctcag tggaacgaaa actcacgtta agggattttg   5280
gtcatgagat tatcaaaaag gatcttcacc tagatccttt taaattaaaa atgaagtttt   5340
aaatcaatct aaagtatata tgagtaaact tggtctgaca gttaccaatg cttaatcagt   5400
gaggcaccta tctcagcgat ctgtctattt cgttcatcca tagttgcctg actccccgtc   5460
gtgtagataa ctacgatacg ggagggctta ccatctggcc ccagtgctgc aatgataccg   5520
cgagacccac gctcaccggc tccagattta tcagcaataa accagccagc cggaagggcc   5580
gagcgcagaa gtggtcctgc aactttatcc gcctccatcc agtctattaa ttgttgccgg   5640
gaagctagag taagtagttc gccagttaat agtttgcgca acgttgttgc cattgctaca   5700
ggcatcgtgg tgtcacgctc gtcgtttggt atggcttcat tcagctccgg ttcccaacga   5760
tcaaggcgag ttacatgatc ccccatgttg tgcaaaaaag cggttagctc cttcggtcct   5820
ccgatcgttg tcagaagtaa gttggccgca gtgttatcac tcatggttat ggcagcactg   5880
cataattctc ttactgtcat gccatccgta agatgctttt ctgtgactgg tgagtactca   5940
accaagtcat tctgagaata gtgtatgcgg cgaccgagtt gctcttgccc ggcgtcaata   6000
cgggataata ccgcgccaca tagcagaact ttaaaagtgc tcatcattgg aaaacgttct   6060
```

```
tcggggcgaa aactctcaag gatcttaccg ctgttgagat ccagttcgat gtaacccact    6120
cgtgcaccca actgatcttc agcatctttt actttcacca gcgtttctgg gtgagcaaaa    6180
acaggaaggc aaaatgccgc aaaaaaggga ataagggcga cacggaaatg ttgaatactc    6240
atactcttcc ttttcaata ttattgaagc atttatcagg gttattgtct catgagcgga    6300
tacatatttg aatgtattta gaaaaataaa caaataggg ttccgcgcac atttccccga    6360
aaagtgccac ctgacgtcta agaaaccatt attatcatga cattaaccta aaaaatagg    6420 cgtatcacga ggccctttcg tctcgcgcgt ttcggtgatg acggtgaaaa cctctgacac    6480
atgcagctcc cggagacggt cacagcttgt ctgtaagcgg atgccgggag cagacaagcc    6540
cgtcagggcg cgtcagcggg tgttggcggg tgtcggggct ggcttaacta tgcggcatca    6600
gagcagatta tactgagagt gcaccatatg cggtgtgaaa taccgcacag atgcgtaagg    6660
agaaaatacc gcatcaggcg ccattcgcca ttcaggctgc gcaactgttg ggaagggcga    6720
tcggtgcggg cctcttcgct attacgccag ctggcgaaag gggatgtgc tgcaaggcga    6780 ttaagttggg taacgccagg gttttcccag tcacgacgtt gtaaaacgac ggccagt       6837

<210> SEQ ID NO 39
<211> LENGTH: 6942
<212> TYPE: DNA
<213> ORGANISM: Artificial Sequence
<220> FEATURE:
<223> OTHER INFORMATION: Description of Artificial Sequence: Synthetic
      P20 polynucleotide

<400> SEQUENCE: 39
cgatgcgcca gtcctccgat agactgagtc gcccgggtac ccgtgtatcc aataaatcct      60
cttgctgttg catccgactc gtggtctcgc tgttccttgg gagggtctcc tcagagtgat     120
tgactacccg tctcgggggt cttttcattag atctgtacaa gtaagctcgc tttcttgctg     180 tccaattct attaaaggtt cctttgttcc ctaagtccaa ctactaaact gggggatatt      240
atgaagggcc ttgagcatct ggattctgcc taataaaaaa catttatttt tcattgcagc     300
tcgagaagga gatcttggcg taatcatggt catagctgtt tcctgtgtga aattgttatc     360
cgctcacaat tccacacaac atacgagccg gaagcataaa gtgtaaagcc tggggtgcct     420
aatgagtgag ctaactcaca ttaattgcgt tgcgctcact gcccgctttc cagtcgggaa     480
acctgtcgtg ccagctgcat taatgaatcg gccaacgcgc ggggagaggc ggtttgcgta     540
ttgggcgctc ttccgcttcc tcgctcactg actcgctgcg ctcggtcgtt cggctgcggc     600
gagcggtatc agctcactca aaggcggtaa tacggttatc cacagaatca ggggataacg     660
caggaaagaa catgtgagca aaaggccagc aaaaggccag gaaccgtaaa aaggccgcgt     720
tgctggcgtt tttccatagg ctccgccccc ctgacgagca tcacaaaaat cgacgctcaa     780
gtcagaggtg gcgaaacccg acaggactat aaagatacca ggcgtttccc cctggaagct     840
ccctcgtgcg ctctcctgtt ccgaccctgc cgcttaccgg atacctgtcc gcctttctcc     900
cttcgggaag cgtggcgctt tctcatagct cacgctgtag gtatctcagt tcggtgtagg     960
tcgttcgctc caagctgggc tgtgtgcacg aaccccccgt tcagcccgac cgctgcgcct    1020
tatccggtaa ctatcgtctt gagtccaacc cggtaagaca cgacttatcg ccactggcag    1080
cagccactgg taacaggatt agcagagcga ggtatgtagg cggtgctaca gagttcttga    1140
agtggtggcc taactacggc tacactagaa ggacagtatt tggtatctgc gctctgctga    1200
agccagttac cttcggaaaa agagttggta gctcttgatc cggcaaacaa accaccgctg    1260
```

```
gtagcggtgg ttttttttgtt tgcaagcagc agattacgcg cagaaaaaaa ggatctcaag    1320
aagatccttt gatcttttct acggggtctg acgctcagtg gaacgaaaac tcacgttaag    1380
ggattttggt catgagatta tcaaaaagga tcttcaccta gatccttta aattaaaaat     1440 gaagttttaa atcaatctaa agtatatatg agtaaacttg gtctgacagt taccaatgct    1500
taatcagtga ggcacctatc tcagcgatct gtctatttcg ttcatccata gttgcctgac    1560
tccccgtcgt gtagataact acgatacggg agggcttacc atctggcccc agtgctgcaa    1620
tgataccgcg agacccacgc tcaccggctc cagatttatc agcaataaac cagccagccg    1680
gaagggccga gcgcagaagt ggtcctgcaa ctttatccgc ctccatccag tctattaatt    1740
gttgccggga agctagagta agtagttcgc cagttaatag tttgcgcaac gttgttgcca    1800
ttgctacagg catcgtggtg tcacgctcgt cgtttggtat ggcttcattc agctccggtt    1860
cccaacgatc aaggcgagtt acatgatccc ccatgttgtg caaaaaagcg gttagctcct    1920
tcggtcctcc gatcgttgtc agaagtaagt tggccgcagt gttatcactc atggttatgg    1980
cagcactgca taattctctt actgtcatgc catccgtaag atgcttttct gtgactggtg    2040
agtactcaac caagtcattc tgagaatagt gtatgcggcg accgagttgc tcttgcccgg    2100
cgtcaatacg ggataatacc gcgccacata gcagaacttt aaaagtgctc atcattggaa    2160
aacgttcttc ggggcgaaaa ctctcaagga tcttaccgct gttgagatcc agttcgatgt    2220
aacccactcg tgcacccaac tgatcttcag catcttttac tttcaccagc gtttctgggt    2280
gagcaaaaac aggaaggcaa aatgccgcaa aaaagggaat aagggcgaca cggaaatgtt    2340
gaatactcat actcttcctt tttcaatatt attgaagcat ttatcagggt tattgtctca    2400
tgagcggata catatttgaa tgtatttaga aaaataaaca aataggggtt ccgcgcacat    2460
ttccccgaaa agtgccacct gacgtctaag aaaccattat tatcatgaca ttaacctata    2520
aaaataggcg tatcacgagg ccctttcgtc tcgcgcgttt cggtgatgac ggtgaaaacc    2580
tctgacacat gcagctcccg gagacggtca cagcttgtct gtaagcggat gccgggagca    2640
gacaagcccg tcagggcgcg tcagcgggtg ttggcgggtg tcggggctgg cttaactatg    2700
cggcatcaga gcagattgta ctgagagtgc accatatgcg gtgtgaaata ccgcacagat    2760
gcgtaaggag aaaataccgc atcaggcgcc attcgccatt caggctgcgc aactgttggg    2820
aagggcgatc ggtgcgggcc tcttcgctat tacgccagct ggcgaaaggg ggatgtgctg    2880
caaggcgatt aagttgggta acgccagggt tttcccagtc acgacgttgt aaaacgacgg    2940
ccagtgaatt cgattagttc aatttgttaa agacaggatc tcagtagtcc aggctttagt    3000
cctgactcaa caataccacc agctaaaacc actagaatac gagccacaat aaataaaaga    3060
ttttatttag tttccagaaa aagggggga tgaaagaccc caccaaattg cttagcctga    3120
tagccgcagt aacgccattt tgcaaggcat ggaaaaatac caaaccaaga atagagaagt    3180
tcagatcaag ggcgggtaca cgaaaacagc taacgttggg ccaaacagga tatctgcggt    3240
gagcagtttc ggccccggcc cggggccaag aacagatggt caccgcggtt cggccccggc    3300
ccggggccaa gaacagatgg tccccagata tggcccaacc ctcagcagtt tcttaagacc    3360
catcagatgt ttccaggctc ccccaaggac ctgaaatgac cctgtgcctt atttgaatta    3420
accaatcagc ctgcttctcg cttctgttcg cgcgcttctg cttcccgagc tctataaaag    3480
agctcacaac ccctcactcg gcgcgccagt cctccgatag actgagtcgc ccgggtaccc    3540
gtgtatccaa taaatcctct tgctgttgca tccgactcgt ggtctcgctg ttccttggga    3600
```

```
gggtctcctc agagtgattg actacccgtc tcggggtct ttcatttggg ggctcgtccg    3660
ggatctggag acccctgccc agggaccacc gacccaccac cgggaggtaa gctggccagc    3720
aattgttctg tgtctgtcca ttgtcctgtg tctttgattg attttatgcg cctgtgtctg    3780
tactagttgg ccgactagat tggtatctgg cggatccgtg gtggaactga cgagttcgag    3840
acacccggcc gcaaccctgg gagacgtccc agggacttcg ggggccattt tgtggcccg    3900
gccagagtcc aaccatcccg atcgttttgg actctttggt gcaccccct tagaggaggg    3960
gtatgtggtt ctggtaggag acagagggct aaaacggttt ccgcccccgt ctgagttttt    4020
gctttcggtt tggaaccgaa gccgcgccgc gcgtcttgtc tgctgcagca tcgttctgtg    4080
ttgtctctgt ttgactgttt ttctgtattt gtctgaaaac atgggccagg ctgttaccac    4140
cccccttaagg tagatgcatc taccttaagt ttgactttag accactggaa ggatgtcgaa    4200
cggacagccc acaacctgtc ggtagaggtt agaaaaaggc gctgggttac attctgctct    4260
gcagaatggc caaccttcaa cgtcggatgg ccacgagacg gcacttttaa cccagacatt    4320
attacacagg ttaagatcaa ggtcttctca cctggcccac atggacatcc ggatcaggtc    4380
ccctacatcg tgacctggga agctatagca gtagacccccc ctccctgggt cagacccttc    4440
gtgcacccta aacctcccct ctctcttccc ccttcagccc cctctctccc acctgaaccc    4500
ccactctcga ccccgcccca gtcctccctc tatccggctc tcacttctcc tttaaacacc    4560
aaacctaggc ctcaagtcct tcctgatagc ggaggaccac tcattgatct actcacggag    4620
gaccctccgc cttaccggga cccagggcca ccctctcctg acgggaacgg cgatagcgga    4680
gaagtggccc ctacagaagg agcccctgac ccttcccccaa tggtatcccg cctgcgggga    4740
agaaaagaac ccccccgtggc ggattctact acctctcagg cgttcccccct tcgcctggga    4800
gggaatggac agtatcaata ctggccattt tcctcctctg acctctataa ctggaaaaat    4860
aacaaccccct ctttctccga ggacccagct aaattgacag ctttgatcga gtccgttctc    4920
cttactcatc agcccacttg ggatgactgc caacagctat tagggaccct gctgacggga    4980
gaagaaaaac agcgagtgct cctagaggcc cgaaaggcgg ttcgagggga ggacggacgc    5040
ccaactcagg gggatcctct agagtcgagc atatgaaatc ttatatgggg cacccccgcc    5100
ccttgtaaac ttccctgatc ctgacatggc aaaggttact cataaccccct ctctccaagc    5160
ccatttacag gcactctacc tggtccagca cgaagtctgg agaccgttgg cggcagctta    5220
ccaagaacaa ctggaccggc cggtagtgcc tcaccctttc cgagtcggtg acacagtgtg    5280
ggtccgcaga caccaaacta aaaatctaga acccgctgg aaaggacctt ataccgtcct    5340
actgactacc cccaccgctc tcaaagtgga cggcattgca gcgtggatcc acgctgccca    5400
cgtataggct gccgacacca ggattgagcc accatcggag ccaccatggc agtcagtcag    5460
tctcgaggct tagcctgata gccgcagtaa cgccattttg caaggcatgg aaaaatacca    5520
aaccaagaat agagaagttc agatcaaggg cgggtacacg aaaacagcta acgttgggcc    5580
aaacaggata tctgcggtga gcagtttcgg ccccggcccg gggccaagaa cagatggtca    5640
ccgcggttcg gccccggccc ggggccaaga acagatggtc cccagatatg cccaaccct    5700
cagcagtttc ttaagaccca tcagatgttt ccaggctccc caaggacct gaaatgaccc    5760
tgtgccttat ttgaattaac caatcagcct gcttctcgct tctgttcgcg cgcttctgct    5820
tcccgagctc tataaaagag ctcacaaccc ctcactcggc gcgtcgcgcg cgggatccac    5880
cggtcgccac catggtgagc aagggcgagg agctgttcac cggggtggtg cccatcctgg    5940
tcgagctgga cggcgacgta aacggccaca agttcagcgt gtccggcgag ggcgagggcg    6000
```

```
atgccaccta cggcaagctg accctgaagt tcatctgcac caccggcaag ctgcccgtgc    6060
cctggcccac cctcgtgacc accctgacct acggcgtgca gtgcttcagc cgctaccccg    6120
accacatgaa gcagcacgac ttcttcaagt ccgccatgcc cgaaggctac gtccaggagc    6180
gcaccatctt cttcaaggac gacggcaact acaagacccg cgccgaggtg aagttcgagg    6240
gcgacaccct ggtgaaccgc atcgagctga agggcatcga cttcaaggag gacggcaaca    6300
tcctggggca caagctggag tacaactaca cagccacaa cgtctatatc atggccgaca    6360
agcagaagaa cggcatcaag gtgaacttca agatccgcca caacatcgag gacggcagcg    6420
tgcagctcgc cgaccactac cagcagaaca cccccatcgg cgacgccccc gtgctgctgc    6480
ccgacaacca ctacctgagc acccagtccg ccctgagcaa agaccccaac gagaagcgcg    6540
atcacatggt cctgctggag ttcgtgaccg ccgccgggat cactctcggc atggacgagc    6600
tgtacaagta aagctcgaga aggaaaaaag cggccgcaag tcgacctgca ggcatgcaca    6660
gatcccgcct agttcaattt gttaaagaca ggatctcagt agtccaggct ttagtcctga    6720
ctcaacaata ccaccagcta aaaccactag aatacgagcc acaataaata aaagatttta    6780 tttagttttcc agaaaaaggg gggttcggcc gaatgaaaga ccccaccaaa ttgcttacgg    6840
atcccccaat tcgcttatgg cacgttgcca atgcttatgg cacgttgcca atgcttatgg    6900
cacgttgcca atgcttatgg cacgttgcca atgcaagctt at                       6942
```

<210> SEQ ID NO 40
<211> LENGTH: 7072
<212> TYPE: DNA
<213> ORGANISM: Artificial Sequence
<220> FEATURE:
<223> OTHER INFORMATION: Description of Artificial Sequence: Synthetic
      P11hp polynucleotide

<400> SEQUENCE: 40

```
gaattcgatt agttcaattt gttaaagaca ggatctcagt agtccaggct ttagtcctga      60
ctcaacaata ccaccagcta aaaccactag aatacgagcc acaataaata aaagatttta     120 tttagttttcc agaaaaaggg gggaatgaaa gaccccacca aattgcttag cctgatagcc    180
gcagtaacgc cattttgcaa ggcatggaaa ataccaaac caagaataga gaagttcaga     240
tcaagggcgg gtacacgaaa acagctaacg ttgggccaaa caggatatct gcggtgagca     300
gtttcggccc cggcccgggg ccaagaacag atggtcaccg cggttcggcc ccggcccggg     360
gccaagaaca gatggtcccc agatatggcc caaccctcag cagtttctta agacccatca     420
gatgtttcca ggctccccca aggacctgaa atgaccctgt gccttatttg aattaaccaa     480
tcagcctgct tctcgcttct gttcgcgcgc ttctgcttcc cgagctctat aaaagagctc     540
acaacccctc actcggcgcg ccagtcctcc gatagactga gtcgcccggg tacccgtgta     600
tccaataaat cctcttgctg ttgcatccga ctcgtggtct cgctgttcct gggagggtc     660 tcctcagagt gattgactac ccgtctcggg gtctttcat ttggggctc gtccgggatc      720 tggagacccc tgcccaggga ccaccgaccc accaccggga ggtaagctgg ccagcaattg     780
ttctgtgtct gtccattgtc ctgtgtcttt gattgatttt atgcgcctgt gtctgtacta     840
gttggccgac tagattggta tctggcggat ccgtggtgga actgacgagt tcgagacacc     900
cggccgcaac cctgggagac gtcccaggga cttcggggc cattttgtg gcccggccag      960 agtccaacca tcccgatcgt tttgactct tggtgcacc ccctagag gaggggtatg       1020 tggttctggt aggagacaga gggctaaaac ggtttccgcc ccgtctgag tttttgcttt     1080
```

```
cggtttggaa ccgaagccgc gccgcgcgtc ttgtctgctg cagcatcgtt ctgtgttgtc   1140
tctgtttgac tgttttttctg tatttgtctg aaaacatggg ccaggctgtt accacccct   1200 taaggtagat gcatctacct taagtttgac tttagaccac tggaaggatg tcgaacggac   1260
agcccacaac ctgtcggtag aggttagaaa aaggcgctgg gttacattct gctctgcaga   1320
atggccaacc ttcaacgtcg gatggccacg agacggcact tttaacccag acattattac   1380
acaggttaag atcaaggtct tctcacctgg cccacatgga catccggatc aggtcccta    1440 catcgtgacc tgggaagcta tagcagtaga ccccctccc tgggtcagac ccttcgtgca    1500
ccctaaacct cccctctctc ttcccccttc agccccctct ctcccacctg aaccccact    1560 ctcgaccccg ccccagtcct ccctctatcc ggctctcact tctcctttaa acaccaaacc   1620
taggcctcaa gtccttcctg atagcggagg accactcatt gatctactca cggaggaccc   1680
tccgccttac cgggacccag ggccaccctc tcctgacggg aacggcgata gcggagaagt   1740
ggcccctaca gaaggagccc ctgacccttc cccaatggta tccgcctgc ggggaagaaa    1800 agaaccccc gtggcggatt ctactacctc tcaggcgttc ccccttcgcc tgggagggaa    1860
tggacagtat caatactggc cattttcctc ctctgacctc tataactgga aaaataacaa   1920
cccctctttc tccgaggacc cagctaaatt gacagctttg atcgagtccg ttctccttac   1980
tcatcagccc acttgggatg actgccaaca gctattaggg accctgctga cgggagaaga   2040
aaaacagcga gtgctcctag aggcccgaaa ggcggttcga ggggaggacg gacgcccaac   2100 tcaggggggat cctctagagt cgagcatatg aaatcttata tggggcaccc ccgcccttg    2160 taaacttccc tgatcctgac atggcaaagg ttactcataa cccctctctc caagcccatt   2220
tacaggcact ctacctggtc cagcacgaag tctggagacc gttggcggca gcttaccaag   2280
aacaactgga ccggccggta gtgcctcacc cttttccgagt cggtgacaca gtgtgggtcc   2340
gcagacacca aactaaaaat ctagaacccc gctggaaagg accttatacc gtcctactga   2400 ctaccccac cgctctcaaa gtggacggca ttgcagcgtg gatccacgct gcccacgtat    2460
aggctgccga caccaggatt gagccaccat cggagccacc atggcagtca gtcagtctcg   2520
agaagcttga tatcgaattc ccacggggtt gggggttgcgc cttttccaag gcagccctgg   2580
gtttgcgcag ggacgcggct gctctgggcg tggttccggg aaacgcagcg gcgccgaccc   2640
tgggtctcgc acattcttca cgtccgttcg cagcgtcacc cggatcttcg ccgctaccct   2700
tgtgggcccc ccggcgacgc ttcctgctcc gcccctaagt cgggaaggtt ccttgcggtt   2760
cgcggcgtgc cggacgtgac aaacggaagc cgcacgtctc actagtaccc tcgcagacgg   2820
acagcgccag ggagcaatgg cagcgcgccg accgcgatgg gctgtggcca atagcggctg   2880
ctcagcgggg cgcgccgaga gcagcggccg ggaaggggcg gtgcgggagg cggggtgtgg   2940
ggcggtagtg tgggccctgt tcctgcccgc gcggtgttcc gcattctgca agcctccgga   3000
gcgcacgtcg gcagtcggct ccctcgttga ccgaatcacc gacctctctc cccaggggga   3060
tccaccggtc gccaccatgg tgagcaaggg cgaggagctg ttcaccgggg tggtgcccat   3120
cctggtcgag ctggacggcg acgtaaacgg ccacaagttc agcgtgtccg gcagggcga    3180 gggcgatgcc acctacggca agctgaccct gaagttcatc tgcaccaccg gcaagctgcc   3240
cgtgccctgg cccacccctcg tgaccaccct gacctacggc gtgcagtgct tcagccgcta   3300
ccccgaccac atgaagcagc acgacttctt caagtccgcc atgcccgaag gctacgtcca   3360
ggagcgcacc atcttcttca aggacgacgg caactacaag acccgcgccg aggtgaagtt   3420
```

```
cgagggcgac acccTggtga accgcatcga gctgaagggc atcgacttca aggaggacgg    3480
caacatcctg gggcacaagc tggagtacaa ctacaacagc cacaacgtct atatcatggc    3540
cgacaagcag aagaacggca tcaaggtgaa cttcaagatc cgccacaaca tcgaggacgg    3600
cagcgtgcag ctcgccgacc actaccagca gaacaccccc atcggcgacg gccccgtgct    3660
gctgcccgac aaccactacc tgagcaccca gtccgccctg agcaaagacc ccaacgagaa    3720
gcgcgatcac atggtcctgc tggagttcgt gaccgccgcc gggatcactc tcggcatgga    3780
cgagctgtac aagtaaagct cgagaaggaa aaaagcggcc gcaagtcgac ctgcaggcat    3840
gcacagatcc cgcctagttc aatttgttaa agacaggatc tcagtagtcc aggctttagt    3900
cctgactcaa caataccacc agctaaaacc actagaatac gagccacaat aaataaaaga    3960
ttttatttag tttccagaaa aaggggggtt cggccgaatg aaagacccca ccaaattgct    4020
tacgatcccc ccagggatgt aattacgtcc ctcccccgct aggggggcagc acccaggcct    4080 gcactgccgc ctgccggcag gggtccagtc cccaggatg taattatgtc cctcccccgc    4140 taggggggcag cacccaggcc tgcactgccg cctgccggca ggggtccagt ccccaggat    4200 gtaattacgt ccctcccccg ctaggggggca gcacccaggc ctgcactgcc gcctgccggc    4260
aggggtccag tccccgggga gctccaatcg atgcgccagt cctccgatag actgagtcgc    4320
ccgggtaccc gtgtatccaa taaatcctct tgctgttgca tccgactcgt ggtctcgctg    4380
ttccttggga gggtctcctc agagtgattg actacccgtc tcgggggtct ttcattagat    4440
cttggcgtaa tcatggtcat agctgtttcc tgtgtgaaat tgttatccgc tcacaattcc    4500
acacaacata cgagccggaa gcataaagtg taaagcctgg ggtgcctaat gagtgagcta    4560
actcacatta attgcgttgc gctcactgcc cgctttccag tcgggaaacc tgtcgtgcca    4620
gctgcattaa tgaatcggcc aacgcgcggg gagaggcggt ttgcgtattg ggcgctcttc    4680
cgcttcctcg ctcactgact cgctgcgctc ggtcgttcgg ctgcggcgag cggtatcagc    4740
tcactcaaag gcggtaatac ggttatccac agaatcaggg gataacgcag gaaagaacat    4800
gtgagcaaaa ggccagcaaa aggccaggaa ccgtaaaaag gccgcgttgc tggcgttttt    4860
ccataggctc cgcccccctg acgagcatca caaaaatcga cgctcaagtc agaggtggcg    4920
aaacccgaca ggactataaa gataccaggc gtttccccct ggaagctccc tcgtgcgctc    4980
tcctgttccg accctgccgc ttaccggata cctgtccgcc tttctccctt cgggaagcgt    5040
ggcgctttct catagctcac gctgtaggta tctcagttcg gtgtaggtcg ttcgctccaa    5100
gctgggctgt gtgcacgaac cccccgttca gcccgaccgc tgcgccttat ccggtaacta    5160
tcgtcttgag tccaacccgg taagacacga cttatcgcca ctggcagcag ccactggtaa    5220
caggattagc agagcgaggt atgtaggcgg tgctacagag ttcttgaagt ggtggcctaa    5280
ctacggctac actagaagga cagtatttgg tatctgcgct ctgctgaagc cagttacctt    5340
cggaaaaaga gttggtagct cttgatccgg caaacaaacc accgctggta gcggtggttt    5400
ttttgtttgc aagcagcaga ttacgcgcag aaaaaaagga tctcaagaag atcctttgat    5460
cttttctacg gggtctgacg ctcagtggaa cgaaaactca cgttaaggga ttttggtcat    5520
gagattatca aaaaggatct tcacctagat ccttttaaat taaaaatgaa gttttaaatc    5580
aatctaaagt atatatgagt aaacttggtc tgacagttac caatgcttaa tcagtgaggc    5640
acctatctca gcgatctgtc tatttcgttc atccatagtt gcctgactcc ccgtcgtgta    5700
gataactacg atacgggagg gcttaccatc tggccccagt gctgcaatga taccgcgaga    5760
cccacgctca ccggctccag atttatcagc aataaaccag ccagccggaa gggccgagcg    5820
```

| | |
|---|---|
| cagaagtggt cctgcaactt tatccgcctc catccagtct attaattgtt gccgggaagc | 5880 |
| tagagtaagt agttcgccag ttaatagttt gcgcaacgtt gttgccattg ctacaggcat | 5940 |
| cgtggtgtca cgctcgtcgt ttggtatggc ttcattcagc tccggttccc aacgatcaag | 6000 |
| gcgagttaca tgatccccca tgttgtgcaa aaaagcggtt agctccttcg gtcctccgat | 6060 |
| cgttgtcaga agtaagttgg ccgcagtgtt atcactcatg gttatggcag cactgcataa | 6120 |
| ttctcttact gtcatgccat ccgtaagatg cttttctgtg actggtgagt actcaaccaa | 6180 |
| gtcattctga aatagtgta tgcggcgacc gagttgctct tgcccggcgt caatacggga | 6240 |
| taataccgcg ccacatagca gaactttaaa agtgctcatc attggaaaac gttcttcggg | 6300 |
| gcgaaaactc tcaaggatct taccgctgtt gagatccagt tcgatgtaac ccactcgtgc | 6360 |
| acccaactga tcttcagcat cttttacttt caccagcgtt tctgggtgag caaaaacagg | 6420 |
| aaggcaaaat gccgcaaaaa agggaataag ggcgacacgg aaatgttgaa tactcatact | 6480 |
| cttcctttt caatattatt gaagcattta tcagggttat tgtctcatga gcggatacat | 6540 |
| atttgaatgt atttagaaaa ataaacaaat aggggttccg cgcacatttc cccgaaaagt | 6600 |
| gccacctgac gtctaagaaa ccattattat catgacatta acctataaaa ataggcgtat | 6660 |
| cacgaggccc tttcgtctcg cgcgtttcgg tgatgacggt gaaaacctct gacacatgca | 6720 |
| gctcccggag acggtcacag cttgtctgta agcggatgcc gggagcagac aagcccgtca | 6780 |
| gggcgcgtca gcgggtgttg gcgggtgtcg ggctggctt aactatgcgg catcagagca | 6840 |
| gattgtactg agagtgcacc atatgcggtg tgaaataccg cacagatgcg taaggagaaa | 6900 |
| ataccgcatc aggcgccatt cgccattcag gctgcgcaac tgttgggaag ggcgatcggt | 6960 |
| gcgggcctct tcgctattac gccagctggc gaaaggggga tgtgctgcaa ggcgattaag | 7020 |
| ttgggtaacg ccagggtttt cccagtcacg acgttgtaaa acgacggcca gt | 7072 |

<210> SEQ ID NO 41
<211> LENGTH: 7232
<212> TYPE: DNA
<213> ORGANISM: Artificial Sequence
<220> FEATURE:
<223> OTHER INFORMATION: Description of Artificial Sequence: Synthetic
    P20hPGK polynucleotide

<400> SEQUENCE: 41

| | |
|---|---|
| gaattcgatt agttcaattt gttaaagaca ggatctcagt agtccaggct ttagtcctga | 60 |
| ctcaacaata ccaccagcta aaccactag aatacgagcc acaataaata aaagatttta | 120 |
| tttagtttcc agaaaaaggg gggaatgaaa gaccccacca aattgcttag cctgatagcc | 180 |
| gcagtaacgc cattttgcaa ggcatggaaa ataccaaac caagaataga gaagttcaga | 240 |
| tcaagggcgg gtacacgaaa acagctaacg ttgggccaaa caggatatct gcggtgagca | 300 |
| gtttcggccc cggcccgggg ccaagaacag atggtcaccg cggttcggcc ccggcccggg | 360 |
| gccaagaaca gatggtcccc agatatggcc caaccctcag cagtttctta agacccatca | 420 |
| gatgtttcca ggctccccca aggacctgaa atgaccctgt gccttatttg aattaaccaa | 480 |
| tcagcctgct tctcgcttct gttcgcgcgc ttctgcttcc cgagctctat aaaagagctc | 540 |
| acaacccctc actcggcgcg ccagtcctcc gatagactga gtcgcccggg tacccgtgta | 600 |
| tccaataaat cctcttgctg ttgcatccga ctcgtggtct cgctgttcct tgggagggtc | 660 |
| tcctcagagt gattgactac ccgtctcggg ggtctttcat ttggggggctc gtccgggatc | 720 |
| tggagacccc tgcccaggga ccaccgaccc accaccggga ggtaagctgg ccagcaattg | 780 |

```
ttctgtgtct gtccattgtc ctgtgtcttt gattgatttt atgcgcctgt gtctgtacta    840
gttggccgac tagattggta tctggcggat ccgtggtgga actgacgagt tcgagacacc    900
cggccgcaac cctgggagac gtcccaggga cttcggggc cattttttgtg gcccggccag    960
agtccaacca tcccgatcgt tttggactct ttggtgcacc ccccttagag gaggggtatg   1020
tggttctggt aggagacaga gggctaaaac ggtttccgcc ccgtctgag tttttgcttt    1080
cggtttggaa ccgaagccgc gccgcgcgtc ttgtctgctg cagcatcgtt ctgtgttgtc   1140
tctgtttgac tgttttttctg tatttgtctg aaaacatggg ccaggctgtt accacccct    1200
taaggtagat gcatctacct taagtttgac tttagaccac tggaaggatg tcgaacggac   1260
agcccacaac ctgtcggtag aggttagaaa aaggcgctgg gttacattct gctctgcaga   1320
atggccaacc ttcaacgtcg gatggccacg agacggcact tttaacccag acattattac   1380
acaggttaag atcaaggtct tctcacctgg cccacatgga catccggatc aggtccccta   1440
catcgtgacc tgggaagcta tagcagtaga ccccccctccc tgggtcagac ccttcgtgca   1500
ccctaaacct cccctctctc ttccccctttc agccccctct ctcccacctg aaccccccact  1560
ctcgaccccg ccccagtcct ccctctatcc ggctctcact tctcctttaa acaccaaacc   1620
taggcctcaa gtccttcctg atagcggagg accactcatt gatctactca cggaggaccc   1680
tccgccttac cgggacccag ggccaccctc tcctgacggg aacggcgata gcggagaagt   1740
ggcccctaca gaaggagccc ctgacccttc cccaatggta tcccgcctgc ggggaagaaa   1800
agaaccccccc gtggcggatt ctactacctc tcaggcgttc cccttcgcc tgggagggaa   1860
tggacagtat caatactggc cattttcctc ctctgacctc tataactgga aaataacaa    1920
cccctctttc tccgaggacc cagctaaatt gacagctttg atcgagtccg ttctccttac   1980
tcatcagccc acttgggatg actgccaaca gctattaggg accctgctga cgggagaaga   2040
aaaacagcga gtgctcctag aggcccgaaa ggcggttcga ggggaggacg gacgcccaac   2100
tcaggggat cctctagagt cgagcatatg aaatcttata tggggcaccc ccgccccttg    2160
taaacttccc tgatcctgac atggcaaagg ttactcataa cccctctctc caagcccatt   2220
tacaggcact ctacctggtc cagcacgaag tctggagacc gttggcggca gcttaccaag   2280
aacaactgga ccggcggta gtgcctcacc cttttccgagt cggtgacaca gtgtgggtcc   2340
gcagacacca aactaaaaat ctagaacccc gctggaaagg accttatacc gtcctactga   2400
ctacccccac cgctctcaaa gtggacggca ttgcagcgtg gatccacgct gcccacgtat   2460
aggctgccga caccaggatt gagccaccat cggagccacc atggcagtca gtcagtctcg   2520
agaagcttga tatcgaattc ccacggggtt ggggttgcgc cttttccaag gcagccctgg   2580
gtttgcgcag gacgcggct gctctgggcg tggttccggg aaacgcagcg gcgccgaccc    2640
tgggtctcgc acattcttca cgtccgttcg cagcgtcacc cggatcttcg ccgctaccct   2700
tgtgggcccc ccgcgacgc ttcctgctcc gcccctaagt cgggaaggtt ccttgcggtt    2760
cgcggcgtgc cggacgtgac aaacggaagc cgcacgtctc actagtaccc tcgcagacgg   2820
acagcgccag ggagcaatgg cagcgcgccg accgcgatgg gctgtggcca atagcggctg   2880
ctcagcgggg cgcgccgaga gcagcggccg ggaaggggcg gtgcgggagg cggggtgtgg   2940
ggcggtagtg tgggccctgt tcctgcccgc gcggtgttcc gcattctgca agcctccgga   3000
gcgcacgtcg gcagtcggct ccctcgttga ccgaatcacc gacctctctc cccaggggga   3060
tccaccggtc gccaccatgg tgagcaaggg cgaggagctg ttcaccgggg tggtgcccat   3120
```

```
cctggtcgag ctggacggcg acgtaaacgg ccacaagttc agcgtgtccg gcgagggcga   3180
gggcgatgcc acctacggca agctgaccct gaagttcatc tgcaccaccg gcaagctgcc   3240
cgtgccctgg cccacccctcg tgaccaccct gacctacggc gtgcagtgct cagccgcta   3300 ccccgaccac atgaagcagc acgacttctt caagtccgcc atgcccgaag ctacgtcca   3360 ggagcgcacc atcttcttca aggacgacgg caactacaag acccgcgccg aggtgaagtt   3420
cgagggcgac accctggtga accgcatcga gctgaagggc atcgacttca aggaggacgg   3480
caacatcctg gggcacaagc tggagtacaa ctacaacagc cacaacgtct atatcatggc   3540
cgacaagcag aagaacggca tcaaggtgaa cttcaagatc cgccacaaca tcgaggacgg   3600
cagcgtgcag ctcgccgacc actaccagca gaacacccc atcggcgacg ccccgtgct   3660 gctgcccgac aaccactacc tgagcaccca gtccgccctg agcaaagacc caacgagaa   3720 gcgcgatcac atggtcctgc tggagttcgt gaccgccgcc gggatcactc tcggcatgga   3780
cgagctgtac aagtaaagct cgagaaggaa aaaagcggcc gcaagtcgac ctgcaggcat   3840
gcacagatcc cgcctagttc aatttgttaa agacaggatc tcagtagtcc aggctttagt   3900
cctgactcaa caataccacc agctaaaacc actagaatac gagccacaat aaataaaaga   3960
ttttatttag tttccagaaa aagggggtt cggccgaatg aaagacccca ccaaattgct   4020
tacggatccc ccaattcgct tatggcacgt tgccaatgct tatggcacgt tgccaatgct   4080
tatggcacgt tgccaatgct tatggcacgt tgccaatgca agcttatcga tccccccgct   4140
tatggcacgt tgccaatgct tatggcacgt tgccaatgct tatggcacgt tgccaatgct   4200
tatggcacgt tgccaatgct tatggcacgt tgccaatgct tatggcacgt tgccaatgct   4260
tatggcacgt tgccaatgca agcttatcga tgcgccagtc ctccgataga ctgagtcgcc   4320
cgggtacccg tgtatccaat aaatcctctt gctgttgcat ccgactcgtg gtctcgctgt   4380
tccttgggag ggtctcctca gagtgattga ctaccgtct cgggggtctt tcattagatc   4440
tgtacaagta agctcgcttt cttgctgtcc aatttctatt aaaggttcct tgttccccta   4500
agtccaacta ctaaactggg ggatattatg aagggccttg agcatctgga ttctgcctaa   4560
taaaaaacat ttatttttca ttgcagctcg agaaggagat cttggcgtaa tcatggtcat   4620
agctgtttcc tgtgtgaaat tgttatccgc tcacaattcc acacaacata cgagccggaa   4680
gcataaagtg taaagcctgg ggtgcctaat gagtgagcta actcacatta attgcgttgc   4740
gctcactgcc cgctttccag tcgggaaacc tgtcgtgcca gctgcattaa tgaatcggcc   4800
aacgcgcggg gagaggcggt ttgcgtattg ggcgctcttc cgcttcctcg ctcactgact   4860
cgctgcgctc ggtcgttcgg ctgcggcgag cggtatcagc tcactcaaag gcggtaatac   4920
ggttatccac agaatcaggg gataacgcag gaaagaacat gtgagcaaaa ggccagcaaa   4980
aggccaggaa ccgtaaaaag gccgcgttgc tggcgttttt ccataggctc cgcccccctg   5040
acgagcatca caaaaatcga cgctcaagtc agaggtggcg aaacccgaca ggactataaa   5100
gataccaggc gtttccccct ggaagctccc tcgtgcgctc tcctgttccg accctgccgc   5160
ttaccggata cctgtccgcc tttctccctt cgggaagcgt ggcgctttct catagctcac   5220
gctgtaggta tctcagttcg gtgtaggtcg ttcgctccaa gctgggctgt gtgcacgaac   5280
cccccgttca gcccgaccgc tgcgccttat ccggtaacta tcgtcttgag tccaacccgg   5340
taagacacga cttatcgcca ctggcagcag ccactggtaa caggattagc agagcgaggt   5400
atgtaggcgg tgctacagag ttcttgaagt ggtggcctaa ctacggctac actagaagga   5460
cagtatttgg tatctgcgct ctgctgaagc cagttacctt cggaaaaaga gttggtagct   5520
```

```
cttgatccgg caaacaaacc accgctggta gcggtggttt ttttgtttgc aagcagcaga    5580
ttacgcgcag aaaaaaagga tctcaagaag atcctttgat cttttctacg ggtctgacg    5640 ctcagtggaa cgaaaactca cgttaaggga ttttggtcat gagattatca aaaaggatct    5700
tcacctagat ccttttaaat taaaaatgaa gttttaaatc aatctaaagt atatatgagt    5760
aaacttggtc tgacagttac caatgcttaa tcagtgaggc acctatctca gcgatctgtc    5820
tatttcgttc atccatagtt gcctgactcc ccgtcgtgta gataactacg atacgggagg    5880
gcttaccatc tggccccagt gctgcaatga taccgcgaga cccacgctca ccggctccag    5940
atttatcagc aataaaccag ccagccggaa gggccgagcg cagaagtggt cctgcaactt    6000
tatccgcctc catccagtct attaattgtt gccgggaagc tagagtaagt agttcgccag    6060
ttaatagttt gcgcaacgtt gttgccattg ctacaggcat cgtggtgtca cgctcgtcgt    6120
ttggtatggc ttcattcagc tccggttccc aacgatcaag gcgagttaca tgatccccca    6180
tgttgtgcaa aaaagcggtt agctccttcg gtcctccgat cgttgtcaga agtaagttgg    6240
ccgcagtgtt atcactcatg gttatggcag cactgcataa ttctcttact gtcatgccat    6300
ccgtaagatg cttttctgtg actggtgagt actcaaccaa gtcattctga atagtgta     6360 tgcggcgacc gagttgctct tgcccggcgt caatacggga taataccgcg ccacatagca    6420
gaactttaaa agtgctcatc attggaaaac gttcttcggg gcgaaaactc tcaaggatct    6480
taccgctgtt gagatccagt tcgatgtaac ccactcgtgc acccaactga tcttcagcat    6540
cttttacttt caccagcgtt tctgggtgag caaaaacagg aaggcaaaat gccgcaaaaa    6600
agggaataag ggcgacacgg aaatgttgaa tactcatact cttcctttt caatattatt    6660 gaagcattta tcagggttat tgtctcatga gcggatacat atttgaatgt atttagaaaa    6720
ataaacaaat aggggttccg cgcacatttc cccgaaaagt gccacctgac gtctaagaaa    6780
ccattattat catgacatta acctataaaa ataggcgtat cacgaggccc tttcgtctcg    6840
cgcgtttcgg tgatgacggt gaaaacctct gacacatgca gctcccggag acggtcacag    6900
cttgtctgta agcggatgcc gggagcagac aagcccgtca gggcgcgtca gcgggtgttg    6960
gcgggtgtcg ggctggctt aactatgcgg catcagagca gattgtactg agagtgcacc    7020
atatgcggtg tgaaataccg cacagatgcg taaggagaaa ataccgcatc aggcgccatt    7080
cgccattcag gctgcgcaac tgttgggaag ggcgatcggt gcgggcctct tcgctattac    7140
gccagctggc gaaaggggga tgtgctgcaa ggcgattaag ttgggtaacg ccagggtttt    7200
cccagtcacg acgttgtaaa acgacggcca gt                                 7232
```

<210> SEQ ID NO 42
<211> LENGTH: 6800
<212> TYPE: DNA
<213> ORGANISM: Artificial Sequence
<220> FEATURE:
<223> OTHER INFORMATION: Description of Artificial Sequence: Synthetic DCaro4.23 polynucleotide

<400> SEQUENCE: 42

```
gatcaagtct tcggatcccc caattcgctt atggcacgtt gccaatgctt atggcacgtt      60
gccaatgctt atggcacgtt gccaatgctt atggcacgtt gccaatgcaa gcttatcgat     120
gatctgcttt ttgcttgtac tgggtctctc tggttagacc agatctgagc ctgggagctc     180
tctggctaac tagggaaccc actgcttaag cctcaataaa gcttgccttg agtgcttcaa     240
gtagtgtgtg cccgtctgtt gtgtgactct ggtaactaga gatccctcag accctttag     300
```

```
tcagtgtgga aaatctctag cagtagtagt tcatgtcatc ttattattca gtatttataa    360
cttgcaaaga aatgaatatc agagagtgag aggaacttgt ttattgcagc ttataatggt    420
tacaaataaa gcaatagcat cacaaatttc acaaataaag cattttttc actgcattct     480 agttgtggtt tgtccaaact catcaatgta tcttatcatg tctggctcta gctatcccgc    540
ccctaactcc gcccagttcc gcccattctc cgccccatgg ctgactaatt ttttattt     600 atgcagaggc cgaggccgcc tcggcctctg agctattcca gaagtagtga ggaggctttt    660
ttggaggcct aggcttttgc gtcgagacgt acccaattcg ccctatagtg agtcgtatta    720
cgcgcgctca ctggccgtcg ttttacaacg tcgtgactgg gaaaaccctg gcgttaccca    780
acttaatcgc cttgcagcac atccccctt cgccagctgg cgtaatagcg aagaggcccg     840
caccgatcgc ccttcccaac agttgcgcag cctgaatggc gaatggcgcg acgcgcctg     900 tagcggcgca ttaagcgcgg cgggtgtggt ggttacgcgc agcgtgaccg ctacacttgc    960
cagcgcccta gcgcccgctc ctttcgcttt cttcccttcc tttctcgcca cgttcgccgg    1020
ctttccccgt caagctctaa atcgggggct ccctttaggg ttccgattta gtgctttacg    1080
gcacctcgac cccaaaaaac ttgattaggg tgatggttca cgtagtgggc catcgccctg    1140
atagacggtt tttcgccctt tgacgttgga gtccacgttc tttaatagtg gactcttgtt    1200
ccaaactgga acaacactca accctatctc ggtctattct tttgatttat aagggatttt    1260
gccgatttcg gcctattggt taaaaaatga gctgatttaa caaaaattta cgcgaatt     1320 taacaaaata ttaacgttta caattccca ggtggcactt ttcggggaaa tgtgcgcgga    1380
accctatttt gtttattttt ctaaatacat tcaaatatgt atccgctcat gagacaataa   1440
ccctgataaa tgcttcaata atattgaaaa aggaagagta tgagtattca acatttccgt   1500 gtcgcccta ttcccttttt tgcggcattt tgccttcctg tttttgctca cccagaaacg    1560
ctggtgaaag taaaagatgc tgaagatcag ttgggtgcac gagtgggtta tcgaactg     1620 gatctcaaca gcggtaagat ccttgagagt tttcgccccg aagaacgttt tccaatgatg   1680
agcactttta aagttctgct atgtggcgcg gtattatccc gtattgacgc cgggcaagag   1740
caactcggtc gccgcataca ctattctcag aatgacttgg ttgagtactc accagtcaca   1800
gaaaagcatc ttacggatgg catgacagta agagaattat gcagtgctgc cataaccatg   1860
agtgataaca ctgcggccaa cttacttctg acaacgatcg gaggaccgaa ggagctaacc   1920
gcttttttgc acaacatggg gatcatgta actcgccttg atcgttggga accggagctg    1980
aatgaagcca taccaaacga cgagcgtgac accacgatgc ctgtagcaat ggcaacaacg   2040
ttgcgcaaac tattaactgg cgaactactt actctagctt cccggcaaca attaatagac   2100
tggatggagg cggataaagt tgcaggacca cttctgcgct cggcccttcc ggctggctgg   2160
tttattgctg ataaatctgg agccggtgag cgtgggtctc gcggtatcat tgcagcactg   2220
gggccagatg gtaagccctc ccgtatcgta gttatctaca cgacggggag tcaggcaact   2280
atggatgaac gaaatagaca gatcgctgag ataggtgcct cactgattaa gcattggtaa   2340
ctgtcagacc aagtttactc atatatactt tagattgatt taaaacttca ttttaattt    2400 aaaaggatct aggtgaagat cctttttgat aatctcatga ccaaaatccc ttaacgtgag   2460
ttttcgttcc actgagcgtc agaccccgta gaaaagatca aggatcttc ttgagatcct    2520 ttttttctgc gcgtaatctg ctgcttgcaa acaaaaaaac caccgctacc agcggtggtt   2580
tgtttgccgg atcaagagct accaactctt tttccgaagg taactggctt cagcagagcg   2640
```

```
cagataccaa atactgtcct tctagtgtag ccgtagttag gccaccactt caagaactct   2700
gtagcaccgc ctacatacct cgctctgcta atcctgttac cagtggctgc tgccagtggc   2760
gataagtcgt gtcttaccgg gttggactca agacgatagt taccggataa ggcgcagcgg   2820
tcgggctgaa cggggggttc gtgcacacag cccagcttgg agcgaacgac ctacaccgaa   2880
ctgagatacc tacagcgtga gctatgagaa agcgccacgc ttcccgaagg gagaaaggcg   2940
gacaggtatc cggtaagcgg cagggtcgga acaggagagc gcacgaggga gcttccaggg   3000
ggaaacgcct ggtatcttta tagtcctgtc gggtttcgcc acctctgact tgagcgtcga   3060
tttttgtgat gctcgtcagg ggggcggagc ctatggaaaa acgccagcaa cgcggccttt   3120
ttacggttcc tggccttttg ctggcctttt gctcacatgt tctttcctgc gttatcccct   3180
gattctgtgg ataaccgtat taccgccttt gagtgagctg ataccgctcg ccgcagccga   3240
acgaccgagc gcagcgagtc agtgagcgag gaagcggaag agcgcccaat acgcaaaccg   3300
cctctccccg cgcgttggcc gattcattaa tgcagctggc acgacaggtt tcccgactgg   3360
aaagcgggca gtgagcgcaa cgcaattaat gtgagttagc tcactcatta ggcaccccag   3420
gctttacact ttatgcttcc ggctcgtatg ttgtgtggaa ttgtgagcgg ataacaattt   3480
cacacaggaa acagctatga ccatgattac gccaagcgcg caattaaccc tcactaaagg   3540
gaacaaaagc tggagctgca agcttaatgt agtcttatgc aatactcttg tagtcttgca   3600
acatggtaac gatgagttag caacatgcct tacaaggaga aaaaagcac cgtgcatgcc   3660
gattggtgga agtaaggtgg tacgatcgtg ccttattagg aaggcaacag acgggtctga   3720
catgattgg acgaaccact gaattgccgc attgcagaga tattgtattt aagtgcctag   3780
ctcgatacaa taaacgggtc tctctggtta gaccagatct gagcctggga gctctctggc   3840
taactaggga acccactgct taagcctcaa taaagcttgc cttgagtgct tcaagtagtg   3900
tgtgcccgtc tgttgtgtga ctctggtaac tagagatccc tcagaccctt ttagtcagtg   3960
tggaaaatct ctagcagtgg cgcccgaaca gggacctgaa agcgaaaggg aaaccagagc   4020
tctctcgacg caggactcgg cttgctgaag cgcgcacggc aagaggcgag gggcggcgac   4080
tggtgagtac gccaaaaatt ttgactagcg gaggctagaa ggagagagat gggtgcgaga   4140
gcgtcagtat taagcggggg agaattagat cgcgatggga aaaaattcgg ttaaggccag   4200
ggggaaagaa aaaatataaa ttaaaacata tagtatgggc aagcagggag ctagaacgat   4260
tcgcagttaa tcctggcctg ttagaaacat cagaaggctg tagacaaata ctgggacagc   4320
tacaaccatc ccttcagaca ggatcagaag aacttagatc attatataat acagtagcaa   4380
ccctctattg tgtgcatcaa aggatagaga taaaagacac caaggaagct ttagacaaga   4440
tagaggaaga gcaaaacaaa agtaagacca ccgcacagca agcggccgct gatcttcaga   4500
cctggaggag gagatatgag ggacaattgg agaagtgaat tatataaata taagtagta   4560
aaaattgaac cattaggagt agcacccacc aaggcaaaga gaagagtggt gcagagagaa   4620
aaaagagcag tgggaatagg agctttgttc cttgggttct tgggagcagc aggaagcact   4680
atgggcgcag cctcaatgac gctgacggta caggccagac aattattgtc tggtatagtg   4740
cagcagcaga acaatttgct gagggctatt gaggcgcaac agcatctgtt gcaactcaca   4800
gtctggggca tcaagcagct ccaggcaaga atcctggctg tggaaagata cctaaaggat   4860
caacagctcc tggggatttg gggttgctct ggaaaactca tttgcaccac tgctgtgcct   4920
tggaatgcta gttggagtaa taatctctg gaacagattg gaatcacacg acctggatgg   4980
agtgggacag agaaattaac aattacacaa gcttaataca ctccttaatt gaagaatcgc   5040
```

```
aaaaccagca agaaaagaat gaacaagaat tattggaatt agataaatgg gcaagtttgt    5100
ggaattggtt taacataaca aattggctgt ggtatataaa attattcata atgatagtag    5160
gaggcttggt aggtttaaga atagtttttg ctgtactttc tatagtgaat agagttaggc    5220
agggatattc accattatcg tttcagaccc acctcccaac cccgagggga cccgacaggc    5280
ccgaaggaat agaagaagaa ggtggagaga gagacagaga cagatccatt cgattagtga    5340
acggatctcg acggtatcgg ttaactttta aagaaaagg ggggattggg gggtacagtg    5400
caggggaaag aatagtagac ataatagcaa cagacataca aaaagaatta caaaaacaaa    5460
ttacaaaaat tcaaaatttt atcgatcacg agactagcct cgagaagctt gatatcgctt    5520
agcctgatag ccgcagtaac gccattttgc aaggcatgga aaaataccaa accaagaata    5580
gagaagttca gatcaagggc gggtacacga aaacagctaa cgttgggcca aacaggatat    5640
ctgcggtgag cagtttcggc cccggcccgg ggccaagaac agatggtcac cgcggttcgg    5700
ccccggcccg gggccaagaa cagatggtcc ccagatatgg cccaaccctc agcagtttct    5760
taagacccat cagatgtttc caggctcccc caaggacctg aaatgaccct gtgccttatt    5820
tgaattaacc aatcagcctg cttctcgctt ctgttcgcgc gcttctgctt cccgagctct    5880
ataaaagagc tcacaacccc tcactcggcg cgtcgcggaa ttccgcggga tccaccggtc    5940
gccaccatgg tgagcaaggg cgaggagctg ttcaccgggg tggtgcccat cctggtcgag    6000
ctggacggcg acgtaaacgg ccacaagttc agcgtgtccg gcgagggcga gggcgatgcc    6060
acctacggca agctgaccct gaagttcatc tgcaccaccg gcaagctgcc cgtgccctgg    6120
cccaccctcg tgaccaccct gacctacggc gtgcagtgct tcagccgcta ccccgaccac    6180
atgaagcagc acgacttctt caagtccgcc atgcccgaag gctacgtcca ggagcgcacc    6240
atcttcttca aggacgacgg caactacaag acccgcgccg aggtgaagtt cgagggcgac    6300
accctggtga accgcatcga gctgaagggc atcgacttca aggaggacgg caacatcctg    6360
gggcacaagc tggagtacaa ctacaacagc cacaacgtct atatcatggc cgacaagcag    6420
aagaacggca tcaaggtgaa cttcaagatc cgccacaaca tcgaggacgg cagcgtgcag    6480
ctcgccgacc actaccagca gaacaccccc atcggcgacg gccccgtgct gctgcccgac    6540
aaccactacc tgagcaccca gtccgccctg agcaaagacc ccaacgagaa gcgcgatcac    6600
atggtcctgc tggagttcgt gaccgccgcc gggatcactc tcggcatgga cgagctgtac    6660
aagtaaagcg gccgcgtcga cgtcggccat aggggtacgt acctttaaga ccaatgactt    6720
acaaggcagc tgtagatctt agccacttt taaaagaaaa gggggggactg gaagggctaa    6780 ttcactccca acgaagacaa                                                6800
```

GENE TRANSFER VECTORS COMPRISING GENETIC INSULATOR ELEMENTS AND METHODS TO IDENTIFY GENETIC INSULATOR ELEMENTS

This application is a National Stage of PCT/IB10/000950 filed Apr. 2, 2010 and claims the benefit of 61/254,351 filed Oct. 23, 2009 and 61/166,420 filed Apr. 3, 2009.

FIELD OF THE INVENTION

The present invention relates to gene transfer vectors and in particular integrating gene transfer vectors which comprise at least one Genetic Insulator Element (GIE) which limits the effects of a regulatory sequence upon another regulatory or coding sequence disposed upon the other side of the GIE. The present invention also relates to methods of identifying GIEs and to the use of an integrating gene transfer vector, in particular a retrovirus vector, in in vivo and ex vivo gene therapy methods as well as to cells and organisms transformed using vectors according to the present invention.

INTRODUCTION

The need for better gene transfer systems, in terms of specificity, efficacy and safety has been and still remains a major challenge in the development of gene therapy, so that the risk/benefit balance of treating a condition via a gene therapy method will be improved sufficiently to allow the routine use of gene therapy in patients.

Retroviral (RV) and other viral and non-viral vectors used in gene therapy often have a preference for particular chromosomal integration regions or targets. It is also well known that chromosomal insertion of a vector can activate or indeed inactivate genes nearby on the chromosome and that chromosomal regulatory sequences can affect the expression of vector encoded, genes, this phenomenon being known as regulatory cross talk. When endogenous genes are improperly expressed in this way, this can lead to these cells becoming cancerous. This oncogenic potential of vectors may stem from the promiscuous activation of cellular genes by endogenous viral regulatory elements and/or exogenous regulatory elements which for instance drive the expression of the exogeneous therapeutic gene product present in the vector. In otherwise successful gene therapy trials, these types of effects have resulted in otherwise unexplained cases of spontaneous leukemia and death in some of the patients.

These major secondary effects have been reported in gene therapy trials in patients with X-linked severe combined immunodeficiency (SCID-X1) with five reported cases of vector induced leukaemia found both in the Paris & London gene therapy trials. Similar effects have also been seen in several other gene therapy trials, for instance X-linked chronic granulomatous disease (X-CGD). These observed side effects of integrative vector mediated gene therapy, reveal current limitations of integrative vectors for gene transfer (Cavazzana-Calvo et al, 2000 and Hacein-Bey-Albina et al, 2003) formerly usedin clinical studies.

It has been shown that the integration of murine leukaemia virus (MLV) based vectors in the SCID-X1 patient was not random. Integration occurred mainly within or close to 5' regulatory regions of transcriptionnally active genes. Insertional mutagenesis can result in acute toxicity (i.e. loss of transduced cells due to mutations of essential genes) or delayed side effects such as cancer induction. The nature and pathogenicity of these delayed side effects are highly context-dependent and will depend in part upon differences in the type of vector, transgene cassette, target cell, transduction conditions (copy number per cell) and disease-specific in vivo conditions for the maintenance and expansion of gene-modified cells.

The addition of genetic insulator elements (GIE) in integrating vectors which are used for gene therapy is an increasingly important avenue of research, in order to circumvent genotoxicity arising from insertional mutagenesis. Whilst the concept of gene therapy using integrating vectors was formulated some time ago and the idea of insulating the vector and genome from each other so as to prevent regulatory cross talk has also been known for sometime, suitable vectors have not yet been generated and therefore efficient and safe gene transfer vectors which would allow routine clinical use in human patients are still not readily available.

Most experiments/clinical trials performed so far with insulated retroviral vectors incorporate either the 1200 bp long HS4 insulator from chicken beta globin or a 250 bp long core sequence from this insulator as single or double copy cloned into the virus LTR (Ye et al., (2003)). It has now been shown that the 1200 bp HS4 insulator is not genetically stable in viral constructs; and it has also been established that the core sequence when present in one or two copies does not shield adjacent genomic neighbouring sequences against unwanted activation by the enhancer/promoter combination driving transgene expression.

There is thus a need to identify alternative sequences which both have enhancer-blocking activity and which have a boundary effect, as well as being stable in the virus and having no major effects upon virus biology and replication.

The present invention therefore relates to a new class of directly or indirectly integrating gene transfer vectors, which comprise in the nucleotide sequence to be integrated into the genome a GIE which prevents or significantly lessens the effects of the integrated sequences upon genomic sequences and vice versa the effects of genomic sequences upon the integrated sequence.

SUMMARY OF THE INVENTION

According to a first aspect of the present invention there is provided a gene transfer vector which comprises at least one genetic insulator element (GIE), wherein said GIE comprises at least two copies of an element selected from the group consisting of:
a first CTCF binding site and a second CTCF binding site, wherein said first and said second CTCF binding sites are derived from the regulatory sequences of different genes;
a CTF binding site.

The inventors have developed a new class of integrating gene transfer vector comprising a new class of GIE which comprise multiple copies of either a CTCF or CTF binding site.

The inventors using different combinations of these elements have established several new species of GIE which they have shown to effectively insulate an exogenous gene encoded in an integrated gene transfer vector, following integration from genomic regulatory interference.

In particular the gene transfer vector (GTV) is an integrating gene transfer vector.

In the present Patent Application the term integrating gene transfer vector (IGTV), is intended to mean a molecule or collection of molecules which allow an exogenous sequence of DNA to be inserted into the genome of a recipient cell. In particular the IGTV may be based upon a virus such as a retrovirus or alternatively upon such materials as retroelements, transposons, liposomes and nanoparticles. In all cases the vectors comprise a nucleotide sequence which due to an innate or enzyme mediated mechanism is inserted into the genome of a host cell either randomly or alternatively at a specific locus (loci). All prior integrating gene transfer vectors share the genotoxic side effects known from examples of such vectors used in clinical trials.

Alternatively the gene targeting vector is a non-integrating gene transfer vector.

In the present Patent Application the term non-integrating gene transfer vector is intended to mean, a molecule or collection of molecules which allow an exogenous sequence of DNA to be expressed in the nucleus or cytoplasm of a transformed cell, but which are not integrated into the genome of the transformed cell. Suitable systems include episomal gene delivery systems, circular DNA molecules including minicircles, mini chromosomes and other suitable methods, including Integration Deficient LentiVectors (IDLV) platform. Although such non-integrating gene transfer vectors have the advantage that they are not expected to inherently have the genotoxic effects associated with IGTVs, a certain percentage of nuclei transformed with these non-integrating vectors are expected to integrate in any event due to random processes such as recombination and DNA repair. Non-integrating gene transfer vector comprising one or more GIE which would act to insulate the non-integrating gene transfer vector from the genome following such a random insertion and vice versa are also encompassed by the present invention therefore. At the present time it is estimated that anywhere up to 2% of non-integrating gene transfer vectors can end up genomically integrated. Therefore the shielding of the contents of these non-integrating gene transfer vectors is another important aspect of the present invention. Once such non-integrating gene transfer vectors, integrate into the genome they become IGTVs and therefore are explicitly comprised within the IGTVs according to this first aspect of the present invention.

In particular therefore the present invention relates to a non-integrating gene transfer vector comprising at least one genetic insulator element as defined above.

CCCTC-binding factor (CTCF) ("CCCTC" disclosed as SEQ ID NO: 31) is a well known regulatory protein whose function in various regulatory and developmental pathways continues to be elucidated (Ohlsson et al., (2001) and (Tae et al., (2007)) and whose consensus binding site is known (Tae et al., (2007)). The inventors have shown that by combining CTCF binding sites derived from the regulatory sequences of different genes, novel functional GIEs can unexpectedly be generated and importantly that when these GIEs are incorporated into an GTV that regulatory cross talk between vector encoded coding sequences and genomic enhancer/promoter elements is reduced.

In the present Patent Application the term derived from, is intended to mean a nucleotide sequence which is created from a parent nucleotide sequence and hence the derivative shares homology with the parent sequence, but may comprise one or more differences from the parent sequence. In particular the derivative nucleotide sequence may be a portion of the parent sequence or may comprise one or more nucleotide changes in comparison thereto.

According to a further aspect of the present invention the CTCF binding site in the GIE is characterised in that it contains a CTCF consensus binding site or has been experimentally shown to be bound by CTCF in vivo or in vitro. The CTCF binding site consensus (SEQ ID NO: 27; SEQ ID NO: 31) and methods to determine CTCF binding to a DNA target are provided in Tae et al., (2007) which is incorporated by reference.

Throughout this Patent Application references to particular sequences such as DNA binding sites and consensus versions of these, refer to both the provided forward sequence and to the complimentary reverse sequence.

According to a further aspect of the present invention the CTF binding site in the GIE is characterised in that it contains a CTF consensus binding site or contains a sequence which has been experimentally shown to bind CTF in vivo or in vitro. The CTF binding consensus and methods to determine CTF binding to a DNA target are provided in Tarapore et al., (1997) which is incorporated by reference.

CCAAT (SEQ ID NO: 30) box-binding transcription factor (CTF) or Nuclear factor I (NF-I) (also known as TGGCA-binding proteins) are a family of vertebrate nuclear proteins which recognize and bind, as dimers to specified DNA targets (Rupp et al., (1990)). The consensus binding sites of CTF (SEQ ID NO: 28, SEQ ID NO: 29, SEQ ID NO: 30) are known from Tarapore et al., (1997) and other sources which are hereby incorporated by reference.

In addition CTCF and CTF binding sites according to the present invention may share a certain level of homology or identity with the listed and other known consensus binding sites.

In particular by a homologous CTCF/CTF binding site it is intended to mean a sequence having at least 50% identity, preferably 60% identity and more preferably between 65 and 100% with one of the CTCF and CTF binding sites or consensus binding sites detailed in the present Patent Application or known in the art.

By identity it is intended to mean, a measurement of identity between two nucleic acid molecules. Identity can be determined by comparing a position in each sequence which may have earlier been aligned for purposes of comparison. When a position in the compared sequence is occupied by the same base, then the molecules are identical at that position. A degree of identity between nucleic acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default settings.

Each of the new GIEs the inventors have developed is smaller than the previously used 1200 bp insulator element and hence is expected to be more stable and to have less effect upon virus biology and infectivity. These new elements are also more functionally active than the previous insulators used as they comprise multiple copies of the essential core binding DNA sequences which provide the insulatory effect and less extraneous matter.

In particular the GIE is disposed in the GTV such that following genomic insertion of the GTV, the GIE is disposed between a genomic sequence and the coding sequences of the GTV.

In particular the first and/or second CTCF binding site or CTF binding site are derived from a CTCF binding site or CTF binding site from the regulatory sequence of a gene from an animal.

The inventors have combined CTCF binding sites from different species. The identification of alternative CTCF and CTF binding sites is possible given the sequence conservation of these sites (Xie X et al., (2007); Kim et al., (2007); Tae et al., (2007); Tarapore et al., (1997)) and such sequences are therefore encompassed by the present invention.

In particular the CTCF binding site is from the regulatory sequences of a gene selected from the group: betaglobin, immunoglobulin lambda locus, secretory protein LOC348174, similar to peripheral-type benzodiazepine receptor-associated protein 1, neuroblastoma breakpoint family, member 15, DKFZp434A0131 protein isoform 1, FKBP6-like, tripartite motif-containing 73, nuclear pore complex interacting protein, NODAL modulator 2, DKFZp434A0131 protein isoform 1, TBC1 domain family member 3C, FRMPD2-related 1, similar to cis-Golgi matrix protein GM130, nuclear pore complex interacting protein, TBC1 domain family member 3C, MUC1 mucin isoform 1 precursor, RD RNA-binding protein, T cell receptor beta-neurotrimin, protocadherin gamma subfamily A, large conductance calcium-activated potassium, cell receptor alpha locus, p53-induced protein, zinc finger protein 384.

In particular the CTCF binding site is selected from the group consisting of SEQ ID NO: 7, SEQ ID NO: 8, SEQ ID NO: 27; SEQ ID NO: 31.

The inventors have used two CTCF binding sites, CTCF1 which comes from regulatory sequences of chicken beta globin (SEQ ID NO: 7) and CTCF2 comes from the regulatory sequences of the human T cell receptor alpha/delta locus (SEQ ID NO: 8) and the CTCF binding sites therein have 64.3% and 78.6% identity with the CTCF consensus 1 (SEQ ID NO: 27) and 100% and 60% with CTCF consensus 2 (SEQ ID NO: 31) respectively.

HS4 is a DNase I-hypersensitive site isolated from the chicken beta-globin gene and described in Bell et al., 1997. Other examples of CTCF binding sites are given in Bell et al., 1997 and these are incorporated by reference into the present Patent Application.

In particular the GIE comprises the sequence SEQ ID NO: 6, which consists of the CTCF1 and CTCF2 sequences.

In particular the GIE comprises between three and six copies of the first and said second CTCF binding sites.

In particular the GIE comprises three copies of said first and said second CTCF binding sites.

In particular the GIE may comprise two or more identical CTF binding domains or alternatively the GIE may comprise two or more different CTF binding domains.

In particular the CTF binding site comprises the sequence SEQ ID NO: 26, SEQ ID NO: 28, SEQ ID NO: 29, SEQ ID NO: 30.

The CTF binding site used by the inventors (SEQ ID NO: 26) has 58% sequence identity with CTF Consensus 1 (SEQ ID NO: 28); 85% sequence identity with CTF consensus 2 (SEQ ID NO: 29) and 100% identity with CTF Consensus 3 (SEQ ID NO: 3).

The inventors have used a particular CTF binding site from the human oncogene Ski (Tarapore et al., (1997)) to validate the use of this binding site as a component of the GIE. In addition CTF binding sites from other genes may also be used and are encompassed by the present invention.

In particular the GIE comprises between two and eight copies of said CTF binding site.

In particular the GIE comprises four copies of the CTF binding site.

In particular the IGTV is a retrovirus vector.

Retrovirus vectors are based upon retroviruses, this group of viruses has a very characterisitic genomic structure comprising at either end of the linear DNA genome, (that is the genome produced by reverse transcription of the RNA genome), this comprises two LTR regions (also known as UTR) which each comprise a U3, R and U5 regions in that order. Contained between these LTR regions are the coding and regulatory sequences of the retrovirus and it is into this central portion of the retroviral genome that sequences encoding therapeutic gene products are inserted.

In particular the retrovirus vector is a gammaretrovirus or lentivirus vector.

Further examples of retroviruses include: avian leukosis-sarcoma, mammalian C-type, B-type viruses, D type viruses, HTLV-BLV group, spumavirus (Coffin, (1996)).

In particular the GIE replaces at least a part of a U3 region of said retrovirus vector. Similarly the replacement can be made in another portion of the virus.

In retroviruses, the deletion of one or more essential elements such as the virus enhancer generates a disabled vector known as a self-inactivating construct (SIN) with reduced virus titer and infectious potential. Such constructs following genomic insertion can not generate further infectious virions. SIN vectors have been shown to be less prone to tumour-induction (Montini et al, 2006 & 2007) but do retain some of the oncogenic potential of unmodified vectors.

Alternatively, the retrovirus vector may be a SIN vector prior to GIE insertion.

In particular the retroviral vector comprises an enhancer.

According to the present invention an enhancer is a DNA sequence or a fragment thereof which when placed in functional combination with a sequence encoding a gene causes an increase in the expression of the gene.

The inventors when constructing their retroviral vectors deleted the endogenous viral enhancer when replacing the U3 portion of the retrovirus vector. They found that this reduced the expression level of a gene expressed by the retrovirus. The inventors have therefore modified the retroviral vector further so as to include an enhancer to increase gene expression levels.

In particular the exogenous enhancer is positioned between the GIE and an exogenous transgene encoded by the retrovirus vector.

In particular the exogenous enhancer is selected from the group consisting of viral enhancers, eukaryotic enhancers, animal enhancers, mammalian enhancers.

Genetic elements which can enhance the expression of adjacent genes are well known and all such enhancer elements are within the scope of the present Patent Application. The enhancer can be endogenous to the viral vector or to the virus from which the vector was derived or alternatively can be exogenous if for instance it comes from a eukaryotic source.

In particular the enhancer comprises the sequence SEQ ID NO: 22. The inventors have used a 133 bp long fragment extending from base 7708 to 7841 of the helper FB29 Fr-MuLV virus as the enhancer in the experiments described herein.

In particular the retrovirus vector comprises a polyA tail.

The inventors have shown that the presence of a polyA tail can significantly increase virus titers.

A polyA tail protects the mRNA molecule from enzymatic degradation in the cytoplasm and aids in transcription termination, export of the mRNA from the nucleus, and translation. Numerous examples of polyA tails are known in the prior art and these are encompassed by the present invention.

In particular the polyA tail is located outside of the sequences derived from the retrovirus. Most particularly the polyA tail is located outside of the U3 of the retrovirus vector.

In particular the polyA tail comes from the human beta globin gene and comprises the sequence SEQ ID NO: 24.

In particular the retrovirus vector comprises a sequence selected from the group: SEQ ID NO: 12 to 19.

Alternatively the present invention also relates to a IGTV based upon a viral vector selected from the group, adenovirus, parvovirus (e.g. adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpes virus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example (Coffin, (1996)).

In particular such non-retrovirus vectors comprise at least one GIE according to the first aspect of the present invention.

Alternatively the invention relates to an IGTV based upon a non-viral vector system such as naked DNA administration, minicircle, electroporation, liposomes, ultrasound, transposase-based and/or homologous recombination mediated insertion methods.

According to a second aspect of the present invention there is provided a cell genetically altered or modified using a retroviral vector according to the second aspect of the present invention.

A cell according to the present invention may be made according to a method, comprising at least the step of:

(a) introducing into a cell, a viral vector, as defined above and thereby generate a genetically modified cell having at least one integrated provirus copy of the viral vector, and (b) isolating the genetically modified cell of step (a), by any appropriate mean.

The viral vector can be transfected into the cell or transduced.

The cell which is modified may be any cell of interest and stem cells in particular. For making transgenic/knock-out animals, the cells are pluripotent precursor cells such as embryo-derived stem (ES) cells, which are well-known in the art. For making recombinant cell lines, the cells may advantageously be human cells.

The present invention also relates to transgenic animals generated using viral vectors according to the present invention and to therapeutic and non therapeutic gene therapy methods using the viral vectors according to the present invention.

A further aspect of the present invention therefore is to identify short genetic elements that can be integrated into IGTV and in particular SIN (self-inactivating) vectors which prevent such unintended activation effects.

According to a third aspect of the present invention therefore, there is provided a method to identify GIEs suitable for use in a GTV involving the steps:

i) generating at least one first construct which comprises a transgene driven by a promoter; and at least one putative GIE, wherein said at least one putative GIE is disposed between said transgene and a genomic sequence following genomic integration of said at least one construct, ii) generating a second construct comprising said transgene driven by said promoter, iii) integrating at least one of said first and said second constructs into the genome of a eukaryotic cell, iv) comparing the expression level of said transgene from said integrated first construct to the expression level of said transgene from said integrated second construct, v) determining the presence of a GIE wherein said expression levels from step iv) are not identical.

In particular the first and second constructs may be IGTVs as described in the present Patent Application.

Alternatively the first and/or second constructs may be non-integrating gene.

BRIEF DESCRIPTION OF THE DRAWINGS

For a better understanding of the invention and to show how the same may be carried into effect, there will now be shown by way of example only, specific embodiments, methods and processes according to the present invention with reference to the accompanying drawings in which.

DETAILED DESCRIPTION

There will now be described by way of example a specific mode contemplated by the Inventors. In the following description numerous specific details are set forth in order to provide a thorough understanding. It will be apparent however, to one skilled in the art, that the present invention may be practiced without limitation to these specific details. In other instances, well known methods and structures have not been described so as not to unnecessarily obscure the description.

Example 1

Materials and Methods

1.1 Generation of Enhancer-Deleted retrovirus LTRs: Self Inactivating Deletions (SIN)

a. Gammaretroviruses

Figure 6A:
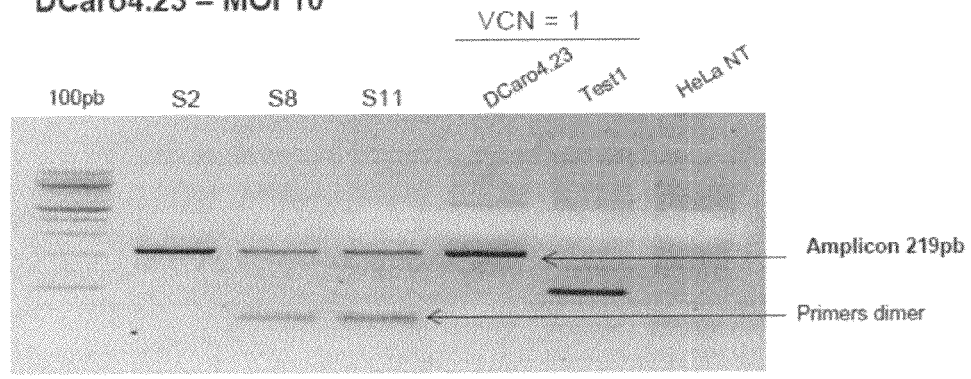
FIG. 6A shows the genetic stability of the insulator 2 sequence provided as four repeats over 12 consecutive weeks of HeLa cells culture; 6B show the genetic stability of 8×Ins2 and 6×Ins1 in HeLa transduced with DCaro8.22 and DCaro6.14.
Figure 6B:
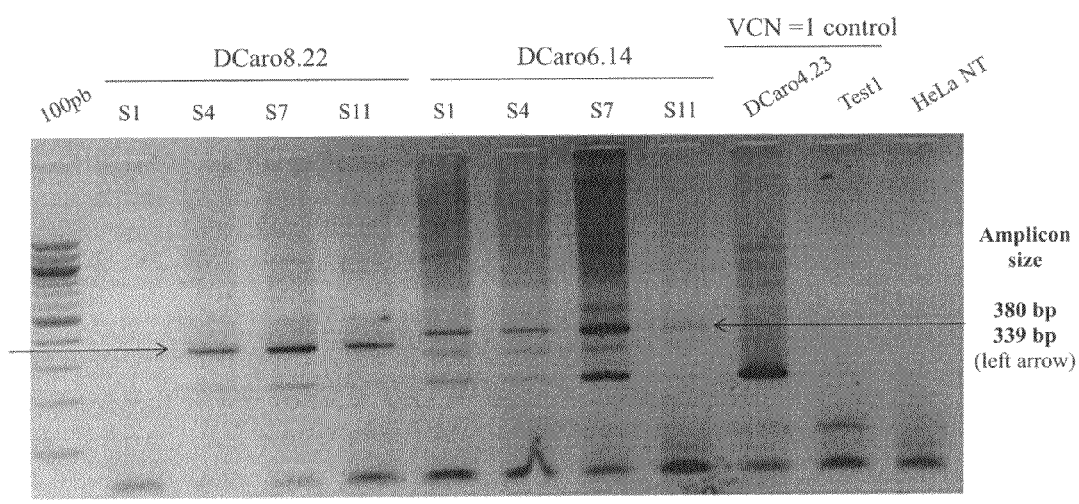
Figure 7B:
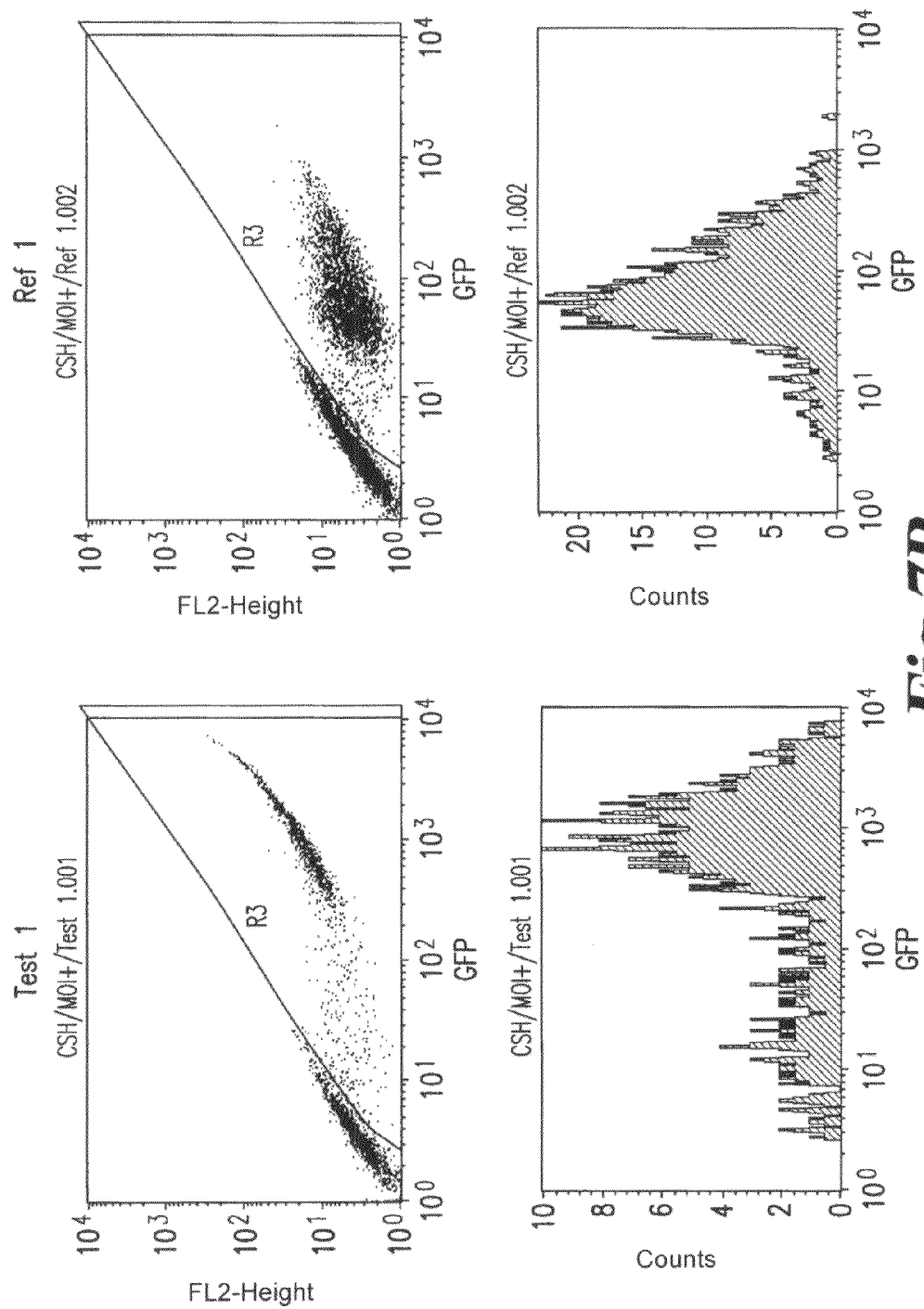
FIGS. 7 A-C show transduction of human CD34+ cells with various lentivirus vectors at 9 weeks
Figure 7C:
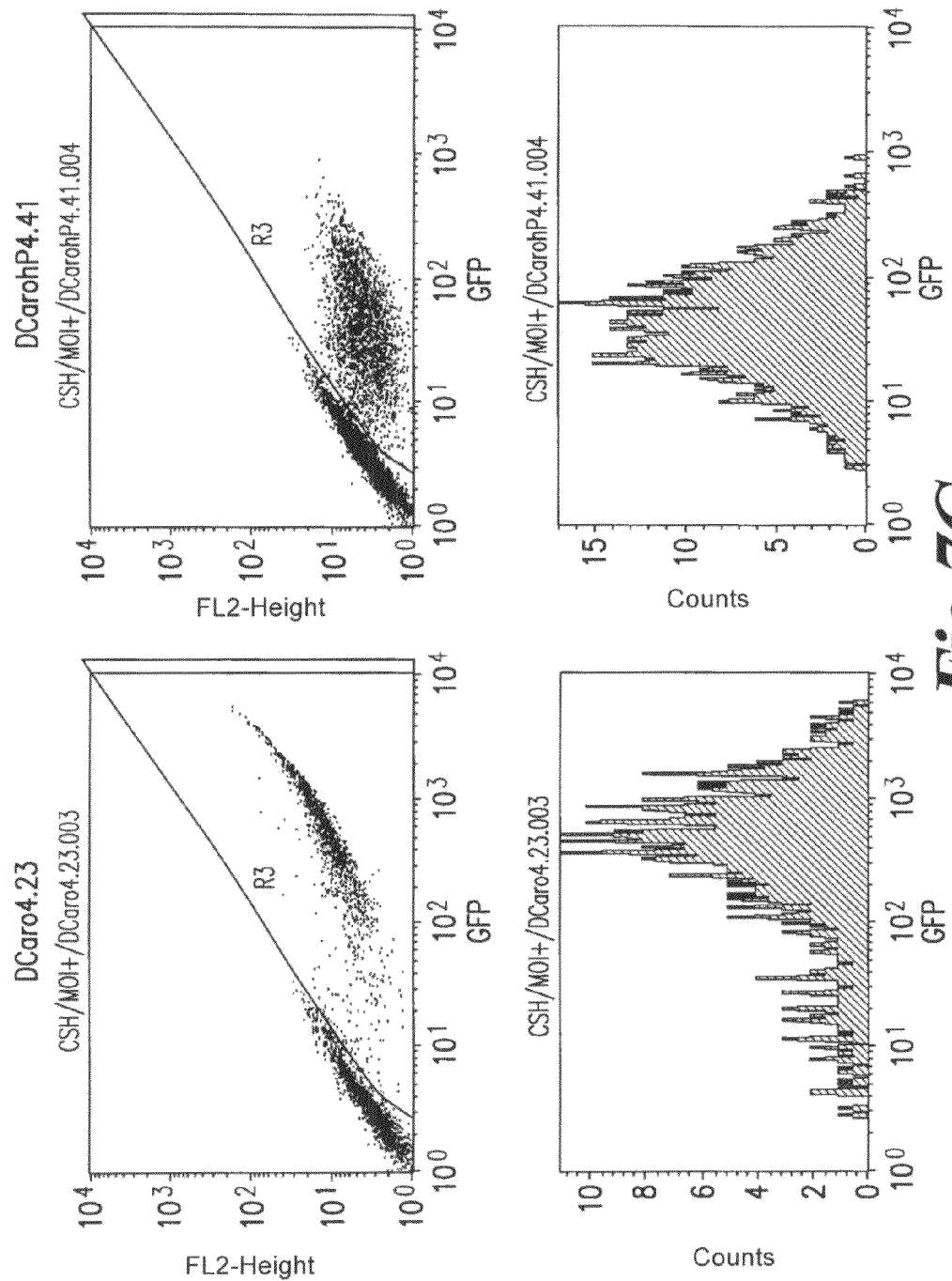

From the above native FrMuLV LTR (FIG. 6, SEQ ID NO: 1), a SIN-24 ΔU3LTR version was derived through the deletion of a 388 bp long sequence, from the U3 sequence, resulting in LTR FrMuLV Delta U 3 (FIG. 7, SEQ ID NO: 2).

In a further step, a BamH1-ClaI polylinker (SEQ ID NO: 3) was added in between base 24 and the start of the R portion of the vector, in order to be able to clone the insulator sequences in later experiments. This step was performed using PCR and the resulting modified LTR sequence was verified (SEQ ID NO: 4).

b. Lentiviruses pSIN-18 pSIN-18 3' LTR vectors (SEQ ID NO: 5) were used as established by Zufferey et al., (1998). A synthetic 118 bp cPPT sequence encompassing a 5' HpaII and a 3'ClaI sites was inserted in the original vector natural ClaI site (position 4010).

LENP29

LENP29 derives from pSIN-18 PGK from which the hPGK-eGFP-WPRE fragment (EcoRV-KpnI) has been removed and replaced by a polylinker (EcoRV-EspI-MluI-BamHI-SalI-KpnI). The U3 region of Friend 29 was obtained by EspI-BssHI partial digestion of FOCHA-FICD and cloned in the compatible sites of the vector polylinker (EspI-MluI). The EGFP1 cDNA was cloned downstream of this internal promoter element. The 18 remaining bases of the U3, in the pSIN-18 3'LTR vector include a BbsI site which was used for the cloning of each insulator element as a BbsI fragment, the non-symetrical ends generated by BbsI digestion allowed the correct orientation of the insulator fragment in the vector.

1.2 Sequences of the Insulators

Insulator1: CTCF 1 CTCF2 repeated 3 times called: "6×CTCF"

This insulator was synthetised as overlapping complementary single stranded oligonucleotides, which were sequentially hybridised to form the multimerised 6×CTCF (SEQ ID NO: 6), which comprises three repeats of the CTCF1 FII site (SEQ ID NO: 7) was derived from the HS4 chicken beta-globin insulator and CTCF2 (SEQ ID NO: 8) was derived from the human T cell receptor alpha/delta locus BEAD-A. 6×CTCF comprises a 5' BamHI site and a 3' ClaI site.

Insulator 2: Multimerised CTF

Multimerised CTF sites consist of various numbers of repeats of DNA sequences containing CAAT transcription factor (CTF) binding sites which were isolated from pNF$_7$CAT plasmid (Tarapore P et al NAR 25: 3895-903, 1997) and analysed by DNA sequencing. Flanking sequences contain appropriate restriction enzyme cleavage sites, 5' ClaI-HindIII and 3' BamHI. Three versions Multimerised CTF sequences were generated 2×CTF Insulator (SEQ ID NO: 9); 4×CTF Insulator (SEQ ID NO: 10) and 7×CTF Insulator (SEQ ID NO: 11). These sequences are provided for the negative strand and following cloning into the relevant vector read along the positive strand.

1.3 Cloning of the Insulators into the SIN LTRs

Gammaretrovirus

The selected insulator fragment and LTR FrMuLV Delta U 3 were each digested with BamHI and ClaI as per the supplier instructions. The digested insulator fragments and vector were then ligated and correctly ligated fragments were verified by sequencing selected clones. The sequence of the modified vectors are LTR FrMuLV Delta U 3 6×CTCF (SEQ ID NO: 12); LTR FrMuLV Delta U 3 2×CTF (SEQ ID NO: 13); LTR FrMuLV Delta U 3 4×CTF (SEQ ID NO: 14); LTR FrMuLV Delta U 3 7×CTF (SEQ ID NO: 15).

Lentivirus

Insulator fragments were cloned into the Lenp29 vector following digestion of the vector with BbsI and the insulator nucleotide molecules with BamHI and ClaI. The sequences of the modified vectors are Lenp29 6×CTCF (SEQ ID NO: 16); Lenp29 2×CTF (SEQ ID NO: 17); Lenp29 4×CTF (SEQ ID NO: 18); Lenp29 7×CTF (SEQ ID NO: 19). The digested insulator fragments and vector were then ligated and correctly ligated fragments were verified by sequencing selected clones.

The cloning strategy to generate DCaro4.23 (SEQ ID NO: 42) was as follows, Test1-cPPT/Lenp29 (FIG. 8, SEQ ID NO: 34) was digested as per manufacturers instructions with BbsI. Test1-cPPT was linearised by this digestion as the plasmid comprises a unique BbsI site. Digested plasmids were run upon an agarose gel and linearised fragments were recovered by gel purification.

Each insulator was amplified by PCR using Taq Phusion, in order to insert a BbsI site at both ends.

PCR was performed using the following primers for the amplification of the 2×CTF, 4×CTF and 7×CTF using the following primers:

```
* Sense oligo: (Ins_BbsI_472sens)
                                       (SEQ ID NO: 20)
         BbsI         ClaI

5'- AAGAAGACAAGATCATCGATAAGCTTGCATTGGC -3'

* Reverse oligo: (lns_Bbsl_4-7rev)
                                       (SEQ ID NO: 21)
              BbsI BamHI

5'- TTTGATCAAGTCTTCGGATCCCCCAATTCGC -3'
```

PCR was performed using the following primers for the amplification of the 6×CTCF element:

(SEQ ID NO: 24)

gctcgctttcttgctgtccaatttctattaaaggttcctttgttccctaagtccaactactaaactgggggatattatgaagggccttgagcatc tggattctgcctaataaaaaacatttattttcattgca.

```
* Oligo sens: (Ins_BbsI_6sens)
                                       (SEQ ID NO : 32)
5'- AAGAAGACAAGATC_GGATCCCCCAGGGATGTAAT -3'

* Oligo reverse: (Ins_BbsI_6rev)
                                       (SEQ ID NO: 33)
5'- TTTGATCAAGTCTTC_ATCGATTGGAGCTCCCCGG -3'
```

Figure 10:
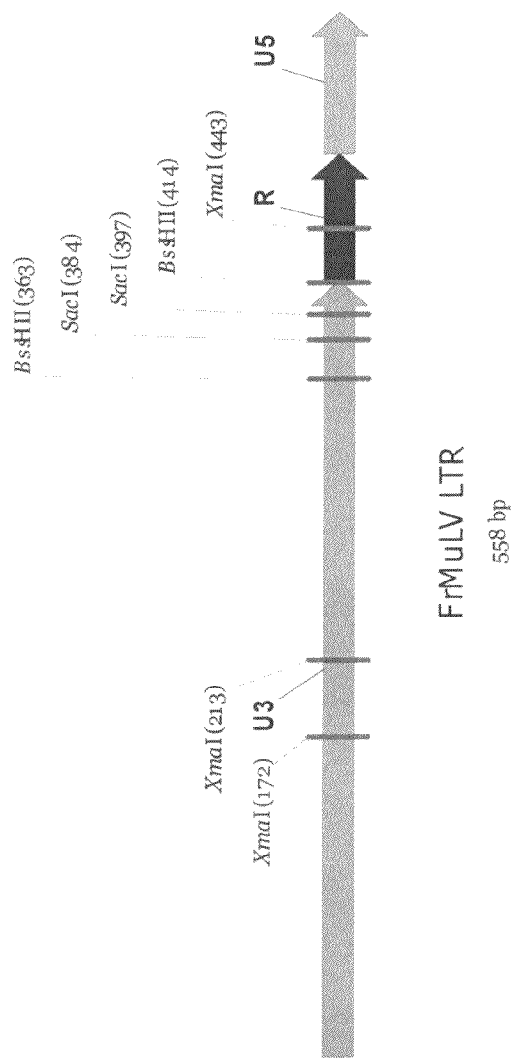
FIG. 10 shows a restriction map of FrMuLV LTR.

Amplified fragments were then digested with BbsI and purified digested fragments were ligated into the previously BbsI digested plasmid Test1-cPPT, recircularising the plasmid when successfully inserted and generating e.g. the DCaro4.23-eGFP or Test1-cPPT-U3-eGFP-4×CTF plasmid (FIG. 10).

```
Fr-MuLV U3
                                                                         (SEQ ID NO: 25)
Ctcgagaagcttgatatcgcnagcctgatagccgcagtaacgccattagcaaggcatggaaaaataccaa accaagaatagagaagttcagatcaagggcgggtacacgaaaacagctaacgttgggccaaacaggatatctgcggtgagcagtttc ggccccggcccggggccaagaacagatggtcaccgcggttcggccccggcccggggccaagaacagatggtccccagatatggc ccaaccctcagcagtttcttaagacccatcagatgtttccaggctcccccaaggacctgaaatgaccctgtgccttatttgaattaaccaat cagcctgcttctcgcttctgttcgcgcgcttctgcttcccgagctctataaaagagctcacaacccctcactcggcgcgtcgcggaattcc gcggatcc.
```

1.4 Fr-MuLV 3'UTR Fragment

The sequence of a 133 bp long fragment extending from base 7708 to 7841 of the helper FB29 Fr-MuLV virus (Cohen-Haguenauer et al., (1998)) is as follows:

TAGTTCAATTTGTTAAAGACAGGATCT-CAGTAGTCCAGGCTTTAG TCCTGACTCAACAATAC-CACCAGCTAAAACCACTAGAATACGAGC-CACAATAAAT AAAAGATTTTATTTAGTTTCC-AGAAAAAGGGGGG (SEQ ID NO: 22), this sequence includes an extra stretch of bps which comes from the cloning strategy and does not affect the performance of this element.

Figure 11:
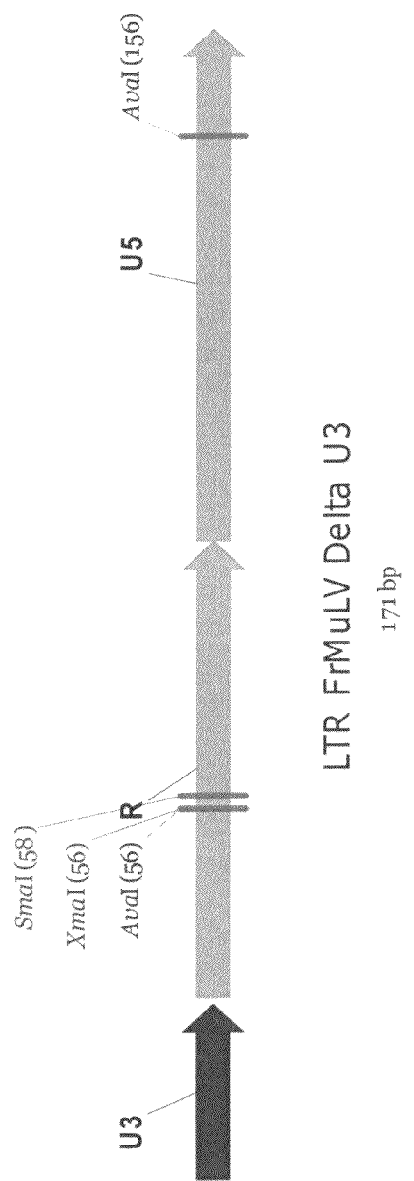
FIG. 11 shows a restriction map of LTR FrMuLV Delta U3.

This fragment was generated by PCR and cloned as an intermediate in a pGEMT shuttle (Promega) generating pGEMT-FrUTR. The Fr-MuLV 3' UTR was cloned by ligating a NotI-EagI fragment from the pGEMT-FrUTR (FIG. 11) to each recipient vector digested at their NotI site.

The sequence of the 3' end of the insulated gammaretrovirus vector named pFOCHa-(U3-eGFP)sens-Fr3'UTR-ΔU3-7-CTF (p23 see Table 1 below), is provided as SEQ ID NO: 23.

1.5 Synthesis of the Beta-Globin polyA Fragment

Figure 12:
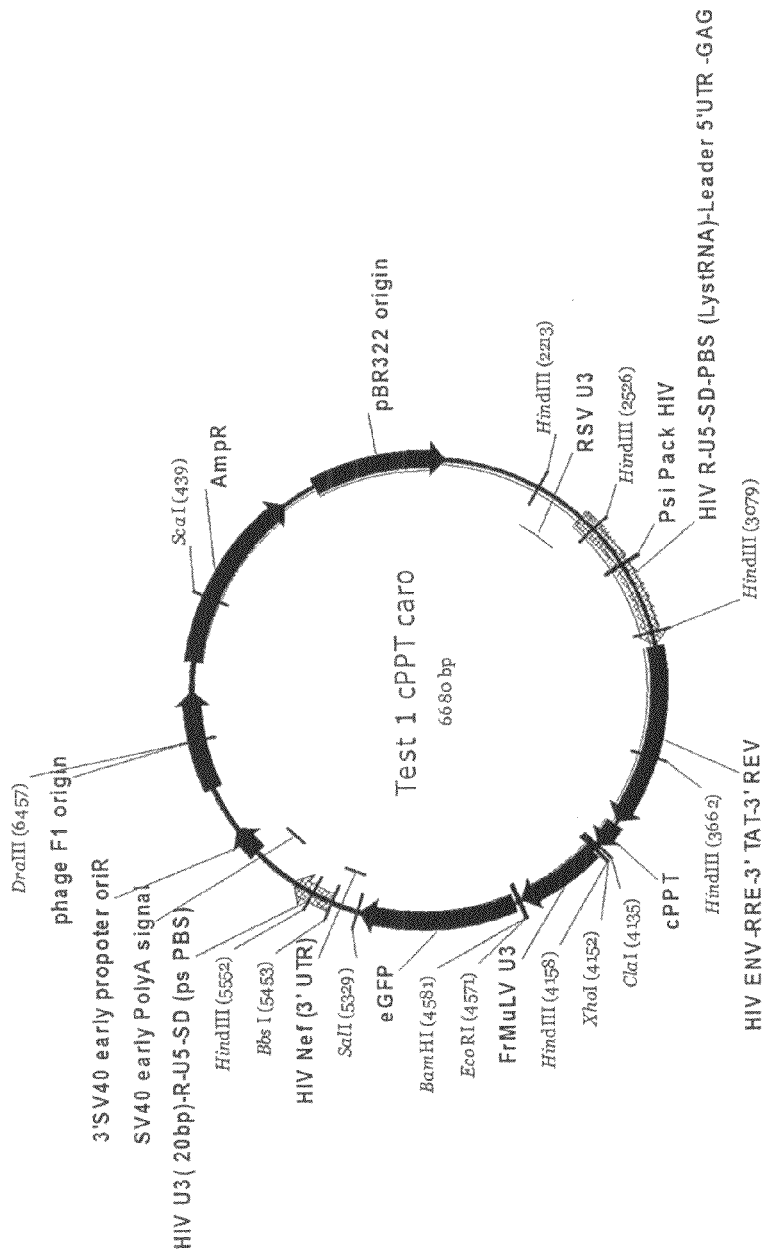
FIG. 12 shows a restriction map of Test 1 cPPT caro also named Lenp29.

A synthetic sequence has been designed and synthetised as follows:

This sequence was inserted into a pGEMT shuttle (Promega), generating the pGEMT-betaGlobpolyA shuttle plasmid, from which it can be retrieved as a 161 bp long BglII fragment (SEQ ID NO: 24) and further oriented using an internal XhoI site (FIG. 12).

Figure 13:
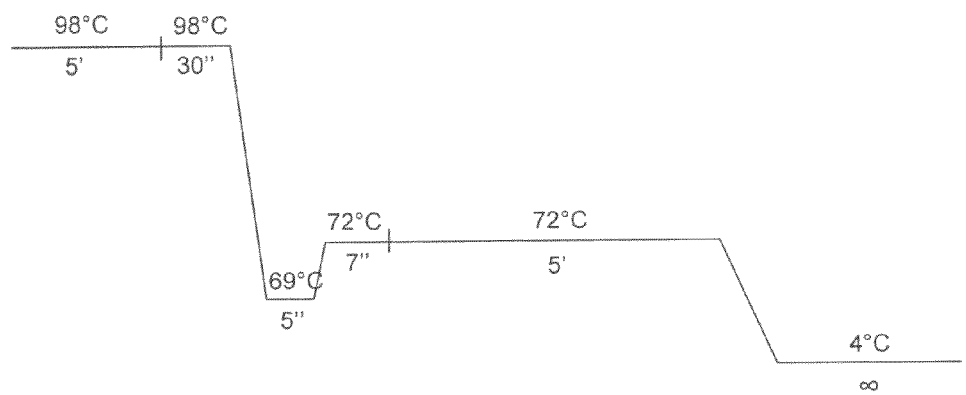
FIG. 13 shows a schematic representation of the PCR cycling conditions for the amplication of different GIEs.
Figure 14:
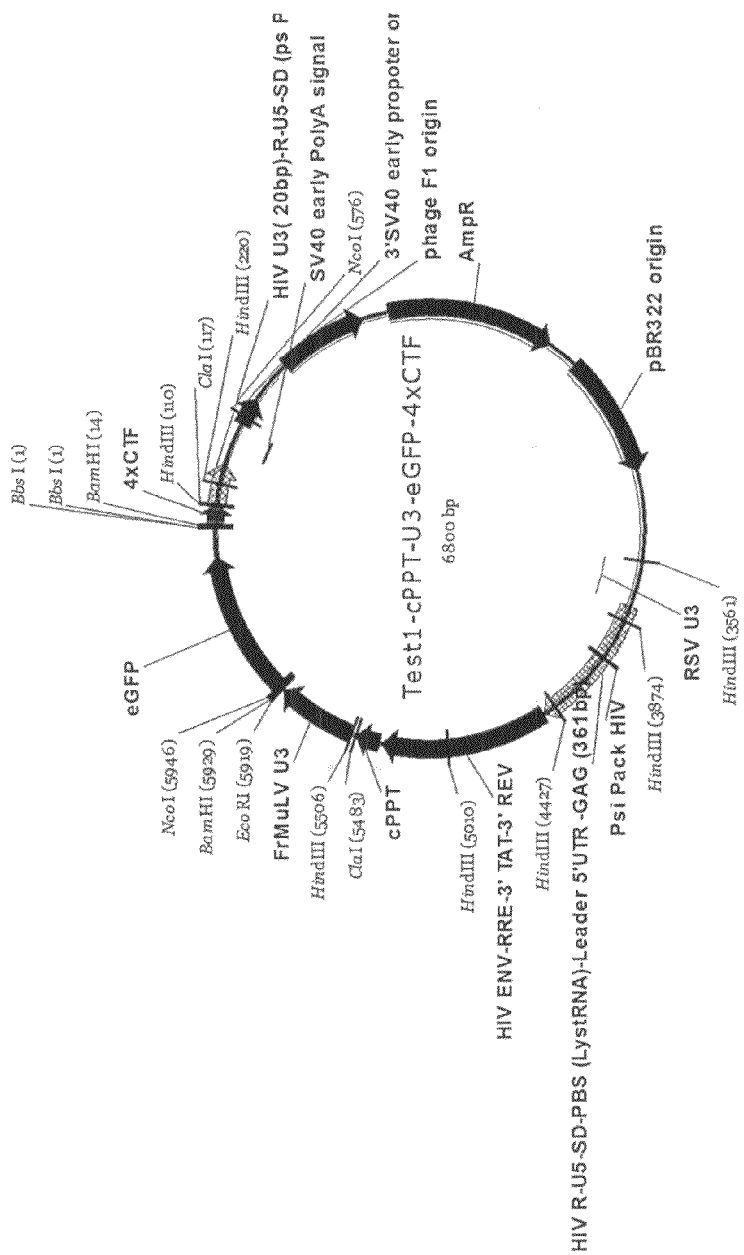
FIG. 14 shows a restriction map of Test 1 cPPT U3 eGFP 4×CTF also named DCaro4.23.

As an example of this cloning regime, the 161 bp BglI fragment from pGEMT-betapolyA was cloned into p11 (FO-CHa-U3-eGFPsens-3'UTR Fr-ΔU3 6×CTCF (FIG. 13)) so as to form p14 (FOCHa-U3-eGFPsens-3'UTR Fr-ΔU3 6×CTCF-betaGlobpolyA (FIG. 14)).

Following all cloning experiments the selected constructs were sequenced to determine the correct orientation and sequence of the constructs.

1.6 Internal Promoters

Each internal promoter used comprised sequences as follows:

This sequence comprises a XhoI and HindIII restriction site at the 5' end (underlined) and an EcoRI and BamHI restriction site at the 3' end (underlined).

hPGK

The initially used 'high expression level' internal promoter (Fr-MuLv U3) was replaced by a housekeeping 'low expression level' hPGK promoter, in each of the insulated constructs giving rise to accurate virus titres, in order to test for both virus production and transgene expression together with genotoxicity characteristics according to the internal promoter driving the expression of the insulated vectors. Each construct is named by adding hP to its parental U3 counterpart (see Table 1, first column).

The hPGK promoter was in combination with the eGFP coding sequence was excised from the pSIN-18 vectors as described above.

Figure 15:
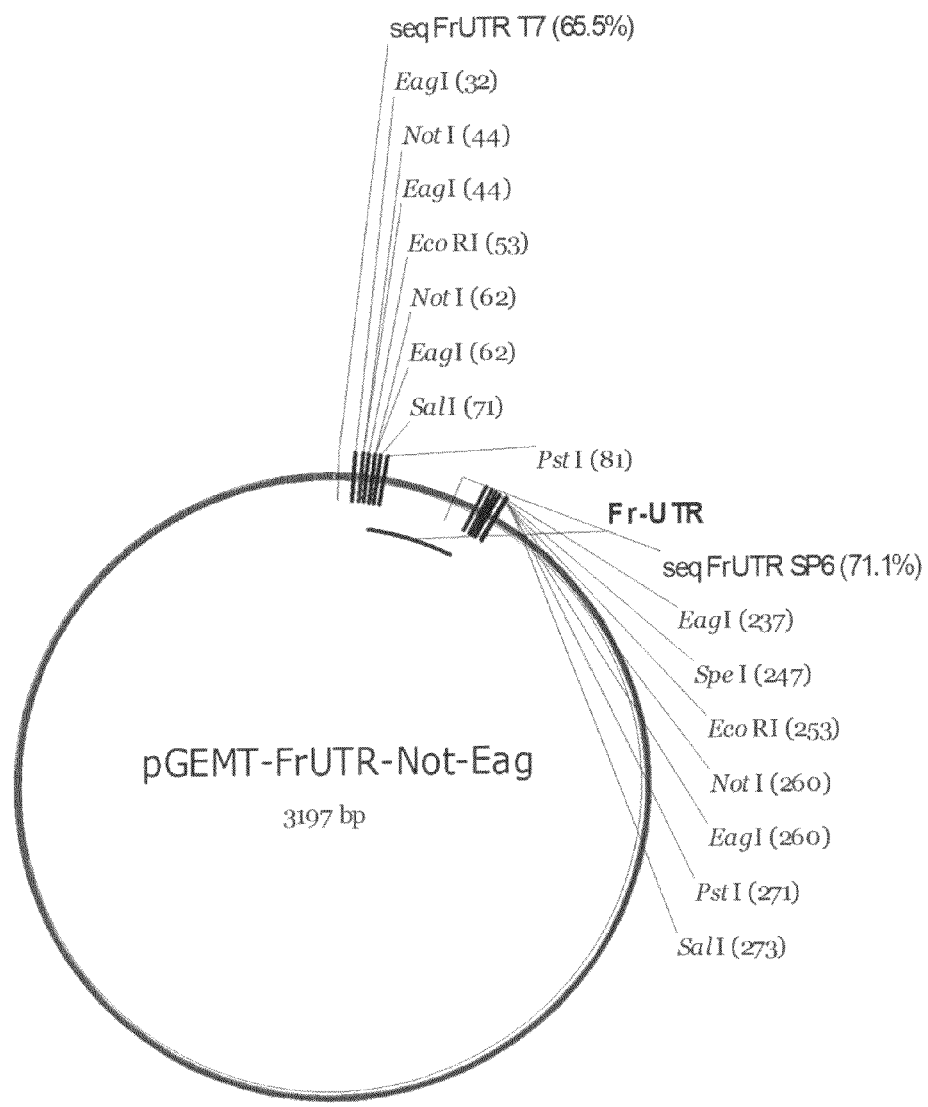
FIG. 15 shows a restriction map of pGEMT-FrUTR-Not-Eag.

The hPGK-eGFP sequence can be excised from its pGEMT-hPGK-eGFP (FIG. 15) shuttle by XhoI digestion and in turn replaces the U3-eGFP XhoI fragment in the recipient insulated vector construct.

An example of the replacement of the U3-eGFP fragment, FOCHa-(U3-eGFP) sens-3'UTR Fr-ΔU3 6×CTCF (FIG. 13) was digested with XhoI as per suppliers instructions, pGEMT-hPGK-eGFP was similarly digested with XhoI and fragments of the correct size were isolated and purified using agarose gel separation and isolation.

Figure 16:
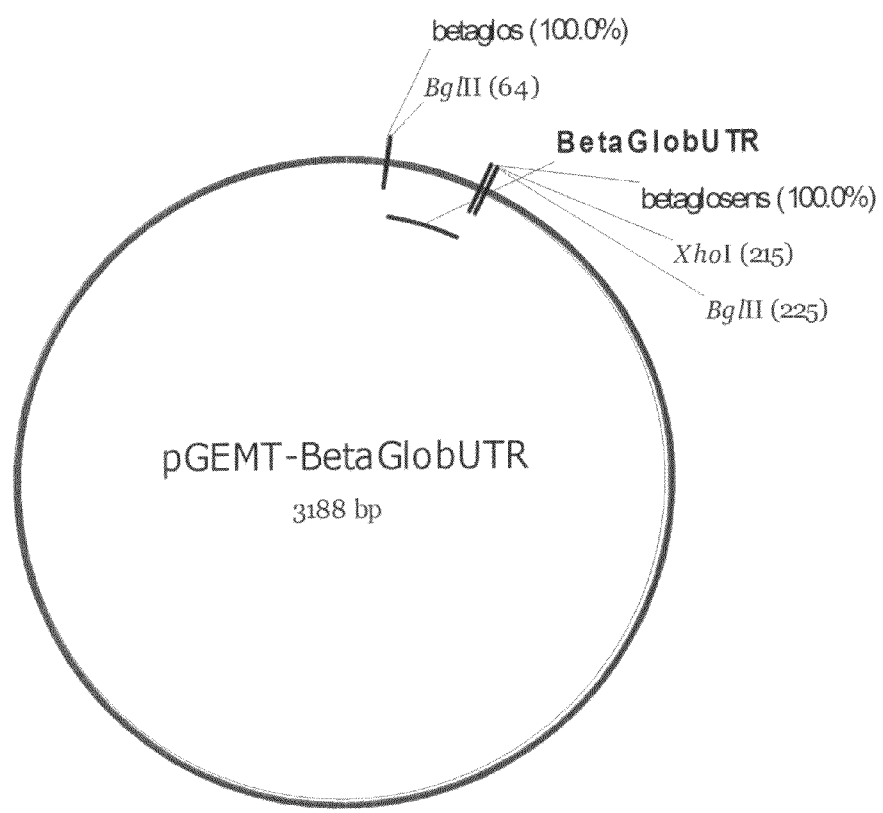
FIG. 16 shows a restriction map of pGEMT-Beta-GlobUTR.
Figure 17:
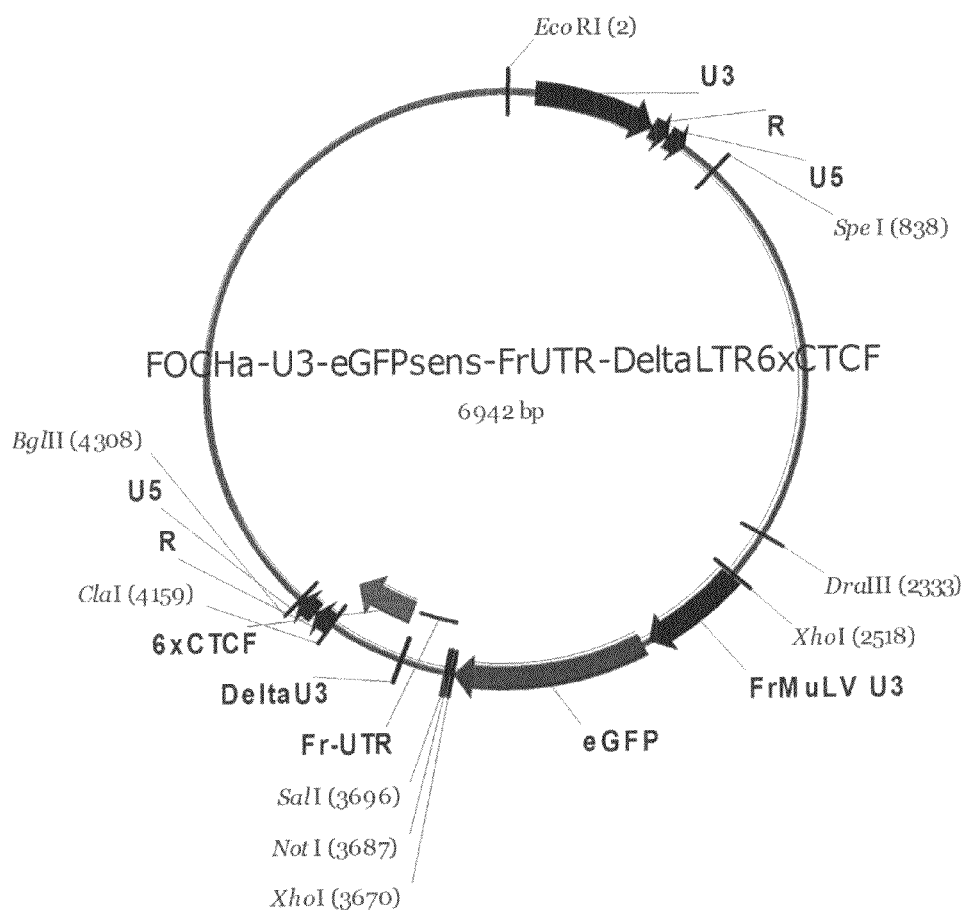
FIG. 17 shows a restriction map of FOCHa-U3-eGFPsens-FrUTR-DeltaLTR6×CTCF.
Figure 18:
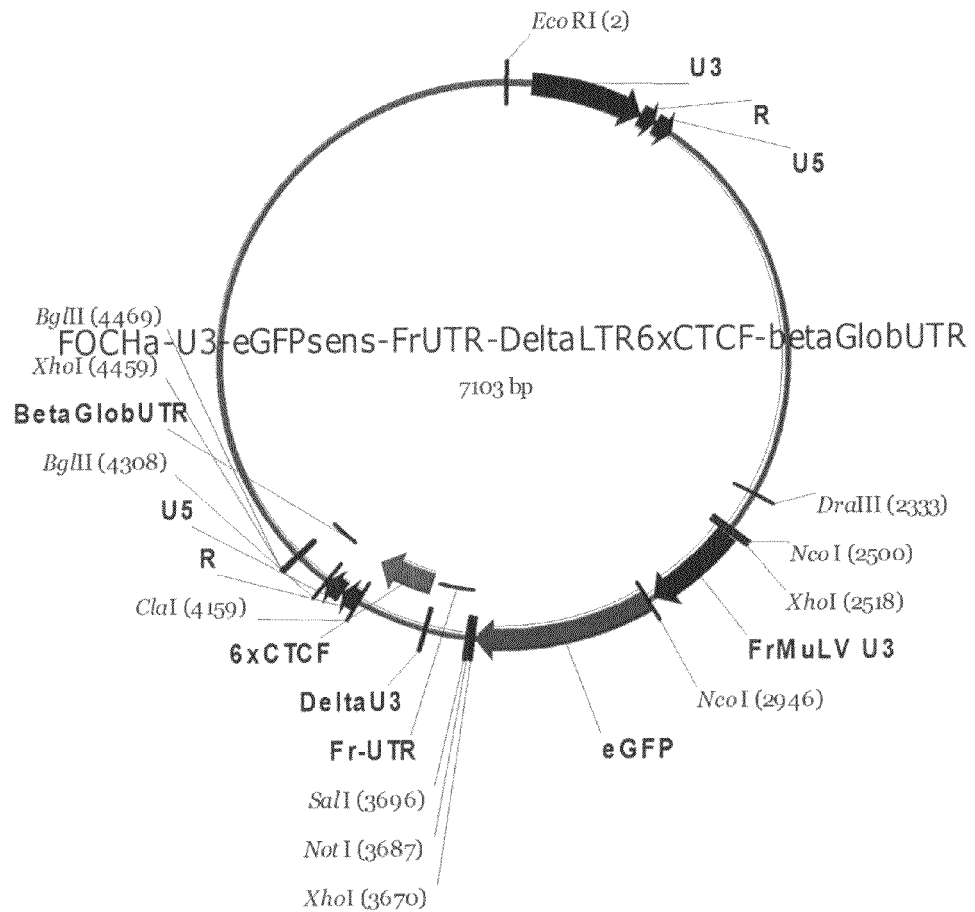
FIG. 18 shows a restriction map of FOCHa-U3-eGFPsens-FrUTR-DeltaLTR6×CTCF-betaGlobUTR.
Figure 19:
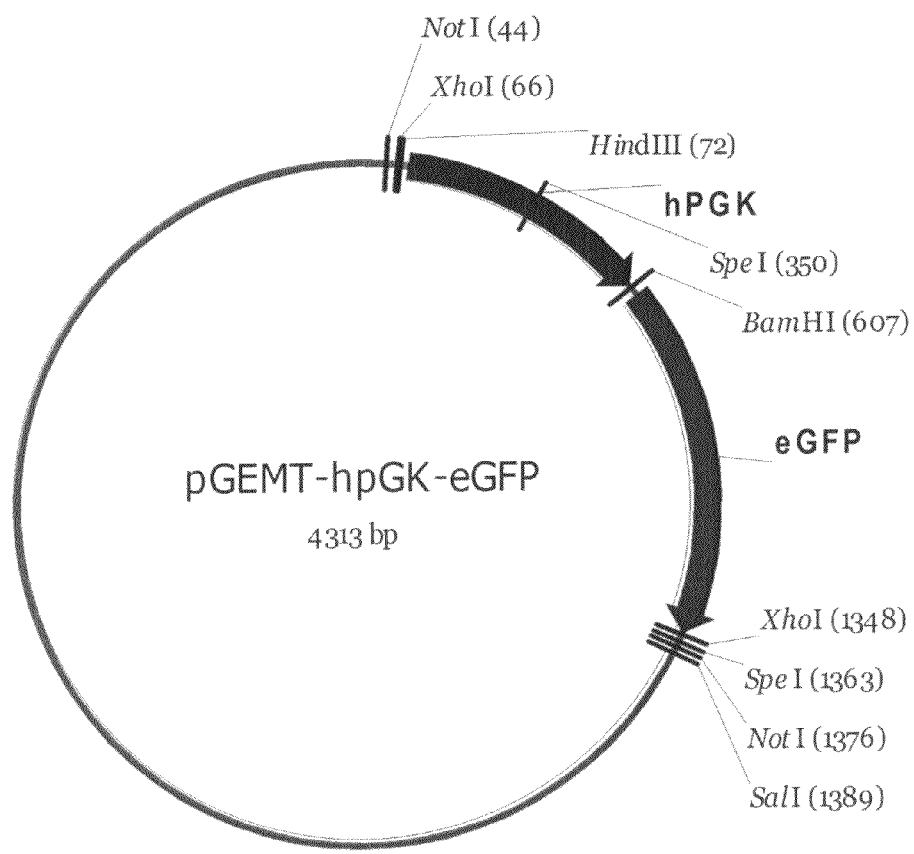
FIG. 19 shows a restriction map of pGEMT-hpGK-eGFP.
Figure 20:
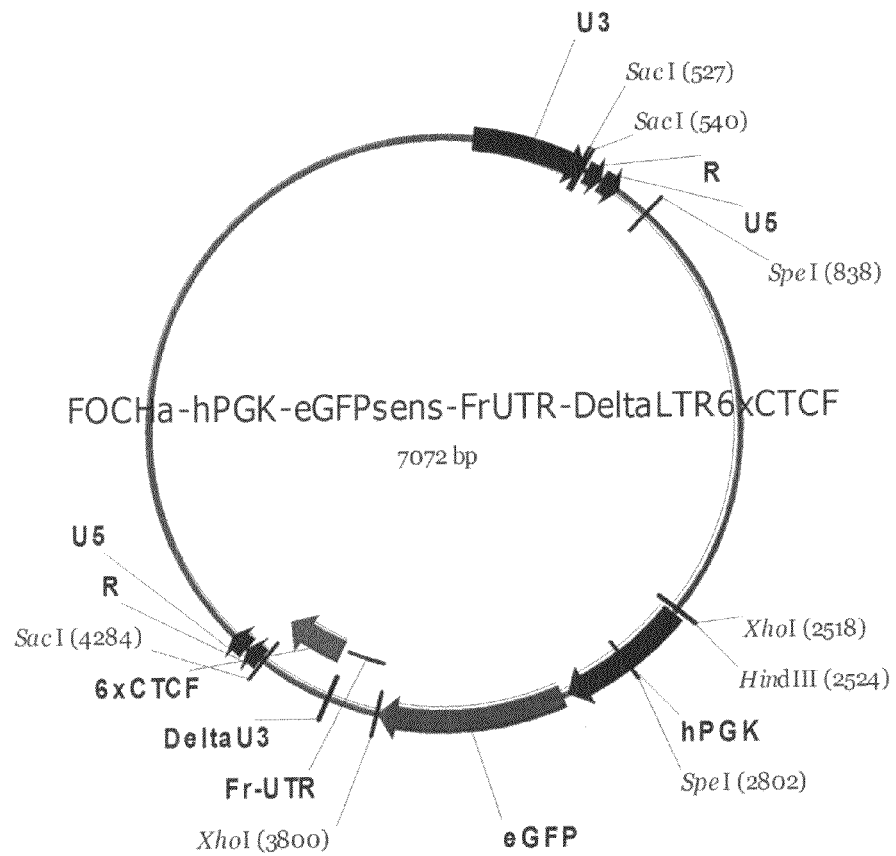
FIG. 20 shows a restriction map of FOCHa-hPGK-eGFPsens-FrUTR-DeltaLTR6×CTCF.

Purified FOCHa-(U3-eGFP) sens-3'UTR Fr-ΔU3 6×CTCF and pGEMT-hpGK-eGFP fragments were then ligated and recircularised plasmids were obtained and sequenced to ensure they contained the correct insert and were the final plasmid FOCHa-(hPGK-eGFP) sens-3'UTR Fr-ΔU3 6×CTCF (FIG. 16).

The replacement of the Fr-MuLV U3 enhancer-promoter by the hPGK promoter was performed in both gammaretrovirus constructs and lentivector constructs. For example data obtained with Dcaro4hP are presented on cord blood derived Human Stem Cells shown in FIGS. 7, 8 and 9.

1.7 Transfections, Virus Production and Transduction Procedures Retrovirus-Producer Clones and Primary Evaluation of Transduction Capacity The third generation of TE-FLY-GA GALV producer cell-lines (kindly forwarded by F-L Cosset) have been engineered with each gamma vectors via primary transfection using co-transfection with a G418 resistance plasmid using SuperFect (Qiagen). Neomycin-resistant clones were pooled and stable producer cells were grown before and after selection of cells expressing EGFP1 by cell-sorting. A helper-virus mobilisation assay was developed using two index-cell lines which allow the detection of GALV pseudotypes (detection of either GFP positive or G418-resistant cells following helper-mobilisation). No helper virus could be detected in any of the tests performed over years, on virus batches produced.

For the lentivectors, quadruple transfections on 293T cells and vector supernatant harvest (including concentration of virus particles using ultracentrifugation) were performed as previously described (Dull et al., (1998). Titers were on average in the $10^9$ to $10^{10}$ cfu/ml range, depending on the vector construct produced and based on both p24 and PCR assays and functional infectious titers from GFP positive cells measured by FACS, at dilution E-5, E-6, E-7 in order to prevent false positive data when further dilution ranges are used Cell Cultures Virus producing cells, 293-T, TE-671 cells and HeLa cells (used for titers/assays) were grown in DMEM with 10% FCS serum, 2 mM of L-Glutamine and 50 µg/ml of gentamycine.

Hematopoietic Cells Transduction.

Cells were thawed in SCGM with 1 mM NAC and 100 ng/ml TPO, and seeded ON in 12 wells plates. Anti-TGFβ (10 µg/ml) was added approx 16 hours before transduction. One cycle of infection was applied the next day at MOI 5-10 in SCGM medium containing: NAC (1 mM), TPO (25 ng/ml), LIF (25 U/ml), SCF/MGDF (25 ng/ml) and Flt-3 (25 ng/ml). After transduction, cells were placed in long-term culture (LTC).

Long Term Culture Conditions

Cells were seeded in liquid LTC culture in SCGM under low concentrations of growth factors: TPO (25 ng/ml), LIF (25 U/ml), SCF/MGDF (25 ng/ml), Flt-3 (25 ng/ml), for the first 6 weeks; from week 7 on, the culture medium included: SCGM medium with TPO (5 ng/ml), LIF (10 U/ml), SCF/MGDF (25 ng/ml), Flt-3 (5 ng/ml), IL3 (5 U/ml), G-CSF (10 U/ml) and Epo (0.5 U/ml). Half of the supernatant was replaced each week. Weekly analysis consisted on counts, FACS analysis of GFP expression, CFUs & PCR assays.

Measurement of eGFP Expression/FACS

Cells were washed and analysed by FACS analysis according to the manufacturers standard protocol and settings (BD FACSCalibur System, Becton, Dickinson and Company) without further labelling. Depending on the samples under test, either 5000 to 50 000 cells are analysed. Sorting of GFP positive cells was performed on a cell-sorter (Vantage, Becton, Dickinson and Company) using standard settings and protocols.

Example 2

Results

2.0 Introduction

The inventors sought to design synthetic GIEs consisting of multimers of specified core sequences. The first one GIE (Insulator 1) is a new combination of CTCF binding sites: 42 bp FII sequence (CTCF1) derived from the HS4 portion of the beta globin gene and a 39 bp BEAD-A sequence (CTCF2) derived from the human T cell receptor alpha/delta locus. Insulator 1 consists of three repeats of the CTCF1-CTCF2 sequence. The second insulator (Insulator 2) comprises multimerised CTF sites which consist of various numbers of repeats of DNA sequences containing CTF binding sites which were isolated from the pNF7CAT plasmid (Tarapore P et al NAR 25: 3895-903, 1997).

A series of insulated gamma- and lenti-, SIN-retrovirus constructs have been engineered using several combinations of the shortest active stretches for the insulators tested, respectively of 268 bp for Insulator 1 and various number of repeats for Insulator 2 of either 181 bp (8×CTF), 157 bp (7×CTF), 101 bp (4×CTF) or 56 bp (2×CTF) long, substituting the U3 LTR enhancer in full in the recipient constructs.

Figure 1A:
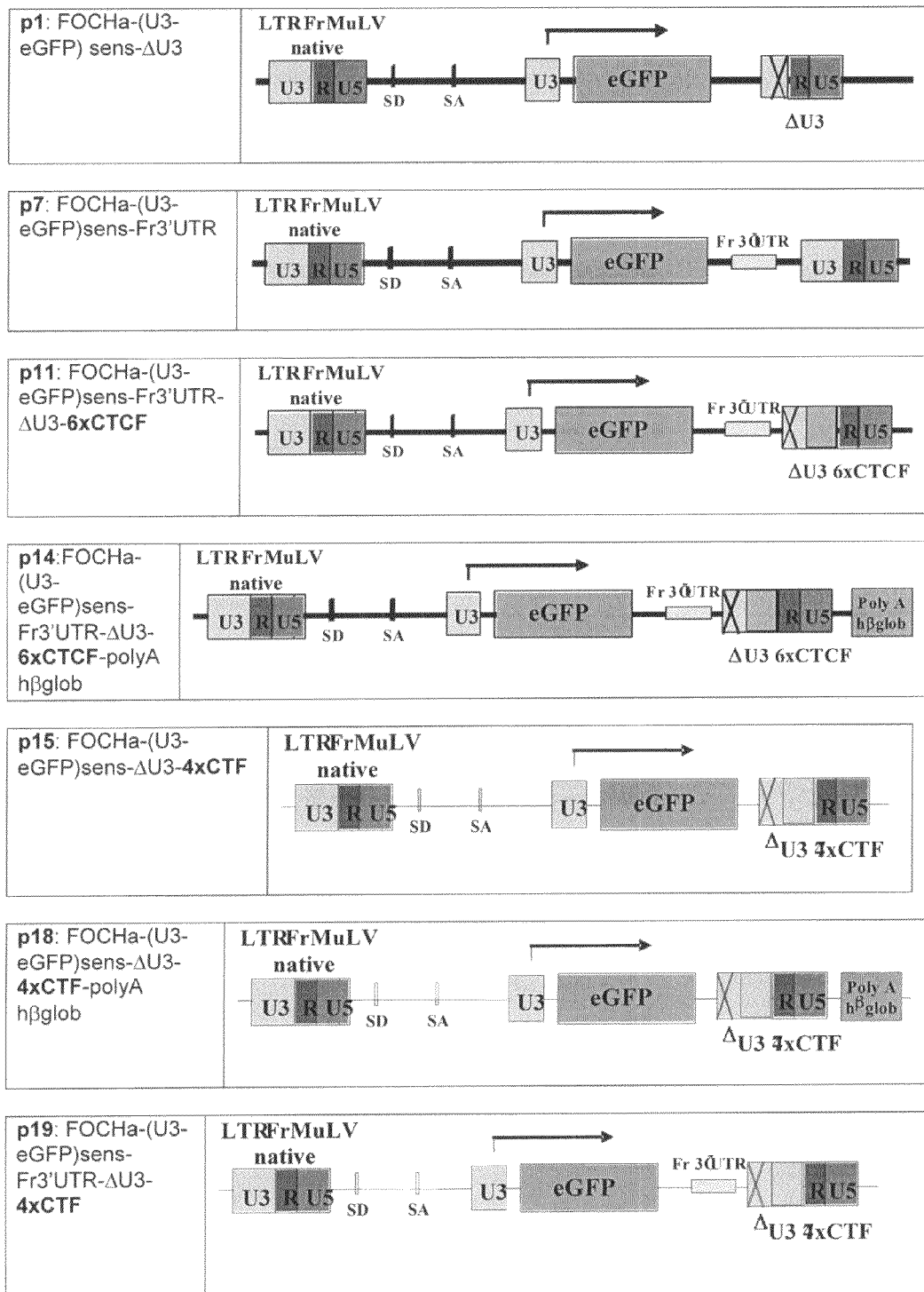
FIG. 1 shows a schematic representation of selected A. Gammaretrovirus vectors and B. Lentivirus vectors.
Figure 1B:
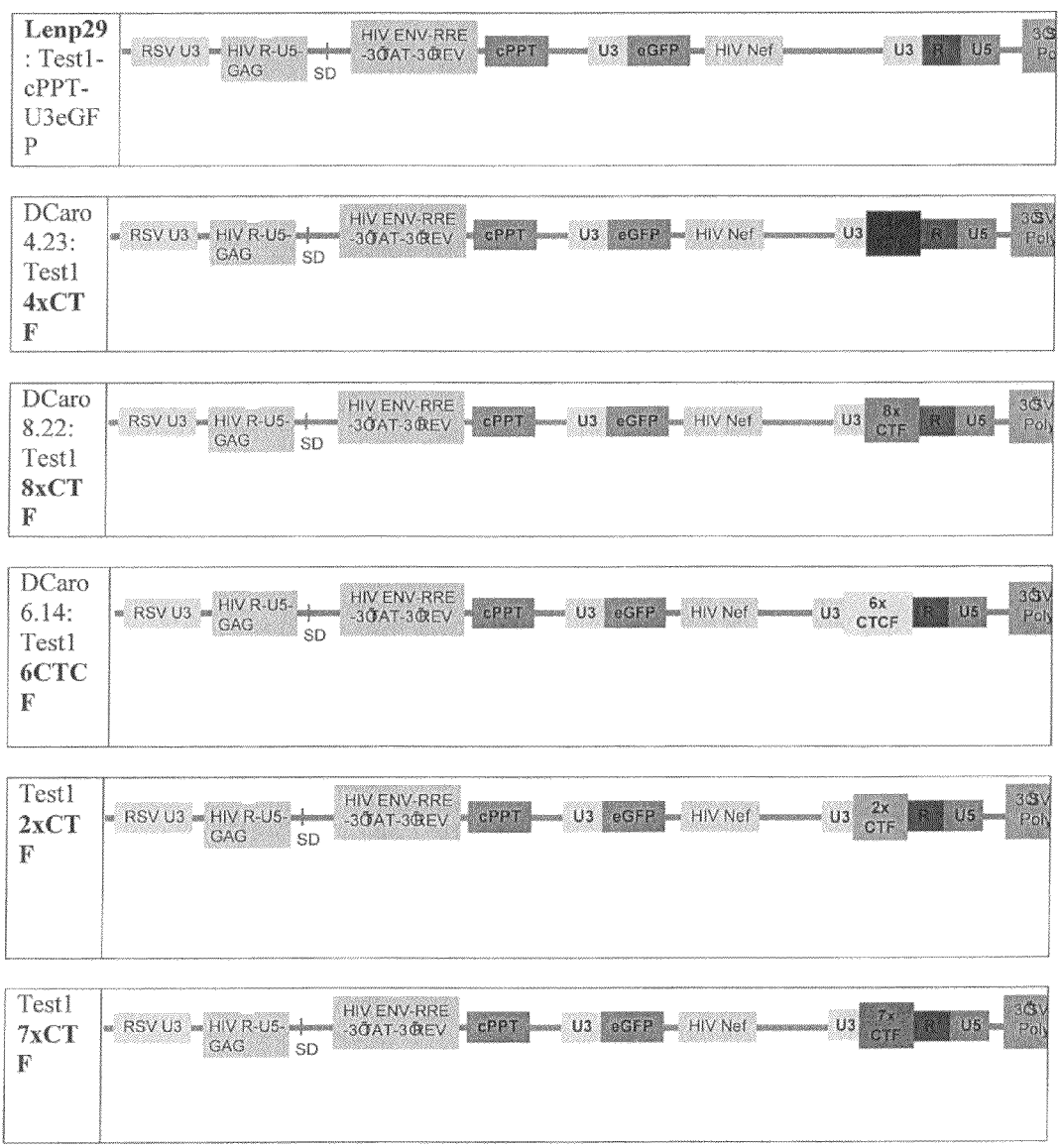

2.1 Key Factors which are Necessary for the Production of Insulated Self-Inactivating Gammaretroviral Vectors with High Titres All constructs designed were tested in comparison with two reference controls: the first, p7 (see Table 1 below) with native LTRs sequences and a strong internal promoter (positive control) and the second p1 a self-inactivating (SIN) vector with a full enhancer-deletion (negative control). A series of insulated vectors have been generated from the SIN-construct and tested, selected examples of these are shown schematically in FIG. 1 and all are listed in Table 1 below.

TABLE 1

List of gammaretrovectors constructed and tested

VECTORS with strong Fr-MuLV U3-promotor

| Name | Structure of the construct |
|---|---|
| P1 | FOCHa-(U3-eGFP)sens-ΔU3 (SEQ ID NO: 35) |
| p2 | FOCHa-(U3-eGFP-polyA hβglob)antisens-ΔU3 |
| P3 | FOCHa-(U3-eGFP-polyA hβglob)antisens-ΔU3-6xCTCF |
| p4 | FOCHa-(U3-eGFP)sens-ΔU3-6xCTCF |
| P5 | FOCHa-(U3-eGFP-polyA hβglob)sens Fr3'UTR |
| p6 | FOCHa-(U3-eGFP-polyA hβglob)antisens Fr3'UTR |
| P7 | FOCHa-(U3-eGFP)sens-Fr3'UTR (SEQ ID NO: 36) |
| P8 | FOCHa-(U3-eGFP)antisens-Fr3'UTR |
| P9 | FOCHa-(U3-eGFP)sens-ΔU3-6xCTCF-polyA hβglob |
| p10 | FOCHa-(U3-eGFP-polyA hβglob)antisens-ΔU3-6xCTCF-polyA hβglob |
| p11 | FOCHa-(U3-eGFP)sens-Fr3'UTR-ΔU3-6xCTCF (SEQ ID NO: 37) |
| p12 | FOCHa-(U3-eGFP-polyA h(3glob)antisens-Fr3'UTR-ΔU3-6xCTCF-polyA hβ-glob |
| p13 | FOCHa-(U3-eGFP-polyA h(3glob)antisens-Fr3'UTR-ΔU3-6xCTCF |
| p14 | FOCHa-(U3-eGFP)sens-Fr3'UTR-ΔU3-6xCTCF-polyAhβglob |
| p15 | FOCHa-(U3-eGFP)sens-ΔU3-4xCTF |
| p18 | FOCHa-(U3-eGFP)sens-ΔU3-4xCTF-polyA hβglob |
| p19 | FOCHa-(U3-eGFP)sens-Fr3'UTR-ΔU3-4xCTF (SEQ ID NO: 38) |
| p20 | FOCHa-(U3-eGFP)sens-Fr3'UTR-ΔU3-4xCTF-polyA hβglob (SEQ ID NO: 39) |
| p21 | FOCHa-(U3-eGFP)sens-Fr3'UTR-ΔU3-2xCTF |
| p22 | FOCHa-(U3-eGFP)sens-Fr3'UTR-ΔU3-2xCTF-polyA hβglob |
| p23 | pFOCHa-(U3-eGFP)sens-Fr3'UTR-ΔU3-7xCTF |
| p24 | FOCHa-(U3-eGFP)sens-Fr3'UTR-ΔU3-7xCTF-polyA hβglob |

VECTORS with housekeeping hPGK-promoter

| Name | Structure of the construct |
|---|---|
| p1hP | FOCHa-(hPGK-eGFP)-sens-ΔU3 |
| p11hP | FOCHa-(hPGK-eGFP)-sens-Fr 3'UTR-DU3-6xCTCF(SEQ ID NO : 40) |
| p14hP | FOCHa-(hPGK-eGFP)sens-Fr3'UTR-AΔU3-6xCTCF-polyA hβglob |
| p15hP | FOCHa-(hPGK-eGFP)sens-AΔU3-4xCTF |
| p18hP | FOCHa-(hPGK-eGFP)sens-AΔU3-4xCTF-polyA hβglob |
| p19hP | FOCHa-(hPGK-eGFP)sens-Fr3'UTR-ΔU3-4xCTF |
| p20hP | FOCHa-(hPGK-eGFP)sens-Fr3'UTR-ΔU3-4xCTF-polyA hβglob (SEQ ID NO: 41) |
| p21hP | FOCHa-(hPGK-eGFP)sens-Fr3'UTR-ΔU3-2xCTF- |
| p22hP | FOCHa-(hPGK-eGFP)sens-Fr3'UTR-ΔU3-2xCTF-polyA hβglob |
| p23hP | FOCHa-(hPGK-eGFP)sens-Fr3'UTR-ΔU3-7xCTF |
| p24hP | FOCHa-(hPGK-eGFP)sens-Fr3'UTR-ΔU3-7xCTF-polyA hβglob |

The simplest constructs were tested first, these only included a splice donor and a splice acceptor followed by an internal promoter driving reporter gene expression, placed either in a sense or an antisense orientation, with reference to the direction of viral transcription.

The internal promoter initially used is a strong enhancer/promoter combination derived from the Fr-MuLV LTR, named "U3" hereafter, which drives transgene expression from the SIN-Insulated vectors in transduced cells. A weaker promoter from the human PGK gene was also used in later experiments.

The inventors decided to use eGFP1 as a reporter gene, the expression level of which was serially measured in both virus-producing and transduced cells, which were sustained in culture for over one month. Virus titers were evaluated from two distinct sources of virus-producer cells, either pools of virus-producer cells or individual clones derived from single-sorted cells seeded in limiting dilutions from those exhibiting the brightest levels of EGFP1 expression.

None of the tested constructs proved useful, as they failed to produce virus at a sufficient titer and at least one to two orders of magnitude less than the control p7 and p1 vectors (Table 1). None of the antisense constructs was able to generate detectable EGFP1 expression in test-target cells.

2.2 Adding the 3'UTR Sequence from the Fr-MuLV FB29 virus strain

The inventors then searched for additional features which would be capable of increasing insulated vectors titers, two rationales were followed and two distinct types of genetic elements were added.
3'UTR Sequence from the Fr-MuLV FB29

Figure 2:
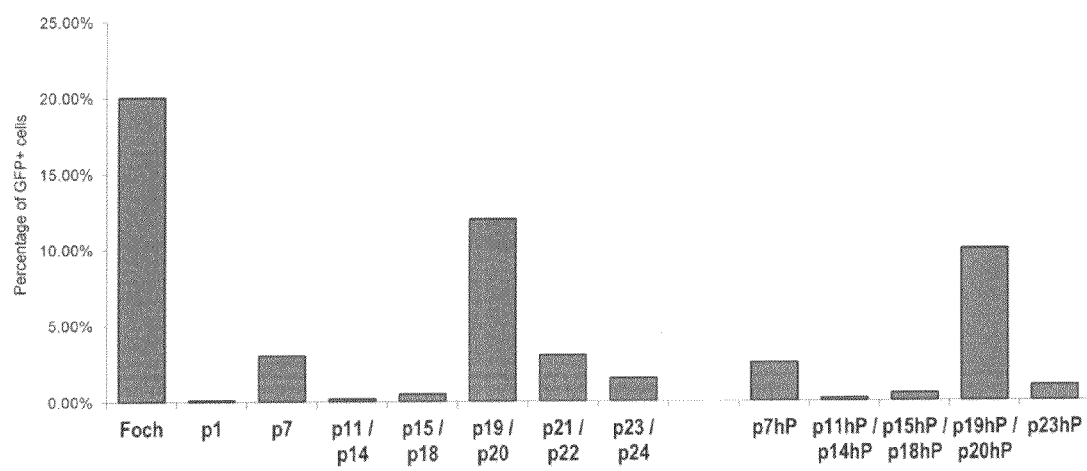
FIG. 2 shows the percentage of GFP producing TE-671 cells for various Gammaretrovirus constructs.

The first element is a 179 bp long 3'UTR sequence from the Fr-MuLV FB29 virus strain, which has been shown to play a critical role in the helper virus biology (Sitbon et al., 1986). Its addition in a downstream position located in between the transgene of interest and the 3' LTR, results in a significant increase in virus titers, by one or two orders of magnitude, according to the insulator used. The most dramatic effect is observed with the Insulator 2 (4×CTF) series of constructs p19/p20, with an increase of virus titers to levels above the p7 control (FIG. 2). This improvement was seen only with constructs in the sense orientation, as antisense constructs did not appear to produce more detectable transduction units. Therefore, no antisense construct was considered in further steps.
PolyA Signal from the Human-β Globin Gene.

A second element was added which does not affect the sequences integrating into the host cell genome, the equivalent of the integrated provirus. The inventors designed and custom-synthetised a polyA sequence derived from the human-β globin gene which was placed outside the virus cassette, downstream of the 3' LTR, in a position which operates in the virus producing cells only. The addition of this sequence downstream to the GIE is intended to facilitate the production of virus read through, with the assumption that the GIE could cause premature interruption of virus RNA synthesis. In fact, the addition of this sequence, was able to induce a dramatic improvement of virus titers with Insulator 2 containing constructs whereas the opposite effect was seen with Insulator 1, in the most dramatic way since virus production dropped to almost undetectable levels with p14 as compared to p11 (Table 2 and data not shown).

In a number of retroviral vectors, the woodchuck hepatitis post-transcriptional regulatory element (WPRE) has been used as a post-transcriptional stabiliser of virus-RNA. This sequence has been reported as potentially oncogenic (Kingsman et al, 2005). Therefore, it was not been placed in any of the retrovirus constructs (whether gammaretrovectors or lenti vectors) tested.

TABLE 2

Relative transduction efficiency of test TE-671 cells using raw virus supernatant (i.e.: without applying selection towards isolation of best virus producing cells).

| Vector | % GFP+ cells | Mean Fluorescence |
|---|---|---|
| U3 internal promoter driven expression | | |
| p1 | 0.87% | 90.45 |
| P7 | 0.75% | 24.77 |
| p11 | 0.40% | 20.99 |
| p14 | 0.06% | 16.82 |
| p19 | 5.05% | 60 |
| p20 | 18.81% | 53.62 |
| hPGK internal promoter driven expression | | |
| p7hP | 2.52% | 21.93 |
| p11hP | 0.24% | 27.48 |
| p14hP | 0.06% | 11.81 |
| p19hP | 8.49% | 20.47 |
| p20hP | 12.78% | 34.31 |

2.3 Comparing Insulator 1 and Insulator 2 and No Insulator in Retroviral Vectors Transgene Expression Level In general the lowest level of eGFP expression is recorded in constructs comprising, Insulator 1, as compared to reference LTR and SIN vectors and constructs comprising Insulator 2 with the same internal promoter, including the strong Fr-MuLV U3 sequence, suggesting a potential inhibitory or silencing effect of Insulator 1. With Insulator 2, a shift in the intensity of the GFP expression is recorded, with a dramatic increase of the mean GFP level and a more homogenous distribution of GFP intensity from one cell to the next, as observed on the FACS profiles. This holds true with both human target cell lines tested, i.e., TE-671 and HeLa with gammaretrovectors (Table 3) and both HeLa cells and human haematopoietic primary stem cells from cord blood followed-up during 12 consecutive weeks after transduction with various lentivector constructs (FIGS. 5 and 8 respectively; in FIG. 8 data shown with Insulator 2 only).

TABLE 3

HeLa test cells transduced with native, SIN & Insulated GammaRVV and lentivectors

| | Producers cells derived from vectors # | % of GFP+ HeLa | Mean Fluorescence |
|---|---|---|---|
| p1 | Sin | 88 | 139 |
| p7 | Native-LTR | 92 | 93 |
| p11 | Fr-U3EP Ins1 | 87 | 58 |
| p15* | Fr-U3EP Ins2 | 89 | 213 |
| p18* | Fr-U3EP Ins2 | 83 | 151 |
| p11hP | hPGK-Pro Ins1 | 94 | 22 |

*= p15 & p18 are identical in transduced cells; they only differ in virus producing cells (polyA downstream the vector 3'LTR)

When lentivectors were tested, the same pattern of expression profile was observed with the lowest eGFP expression levels recorded in DCaro6.14 (Insulator 1) as compared to DCaro4.23 (Insulator 2) or reference vectors. In this case, the mean eGFP fluorescence intensity is brighter with the insulator 2 carrying vector as compared to pSIN-18 as shown in FIGS. 4, 5, 6 and 7 and Table 6.

Transgene Expression Stability eGFP positive transduced HeLa cells were sorted 5 days after exposure to the vectors and sequentially passed ($1/10^{th}$) each week and followed over a three months period.

Figure 3A:
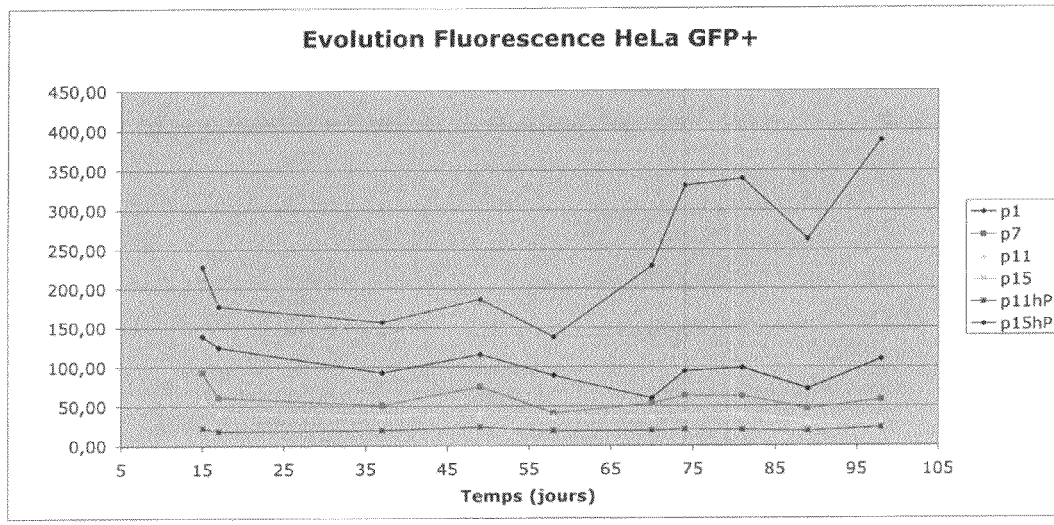
FIG. 3 shows the evolution A. of mean fluorescence in HeLa cells over time and B. percentage of HeLa cells fluorescing over 12 consecutive weeks in culture with gammaretroviral vectors.
Figure 3B:
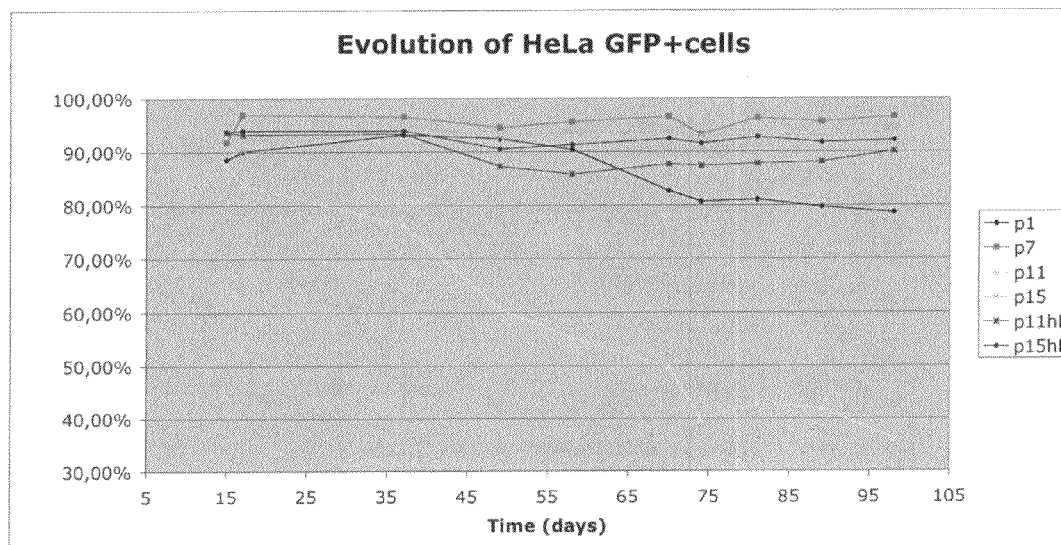
Figure 4A:
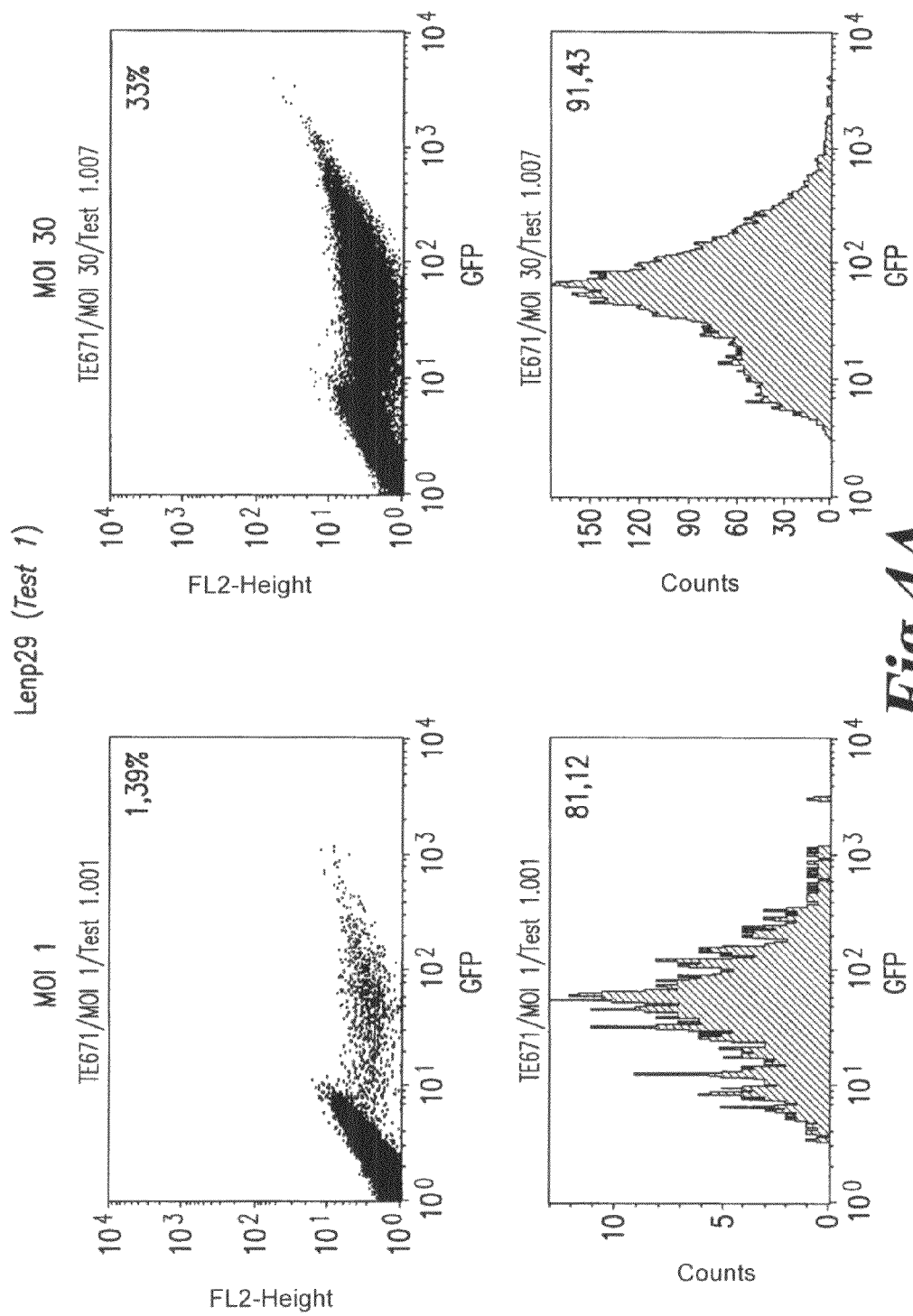
FIGS. 4A-D show transduction of human TE 671 cells with various lentivirus vectors.
Figure 4B:
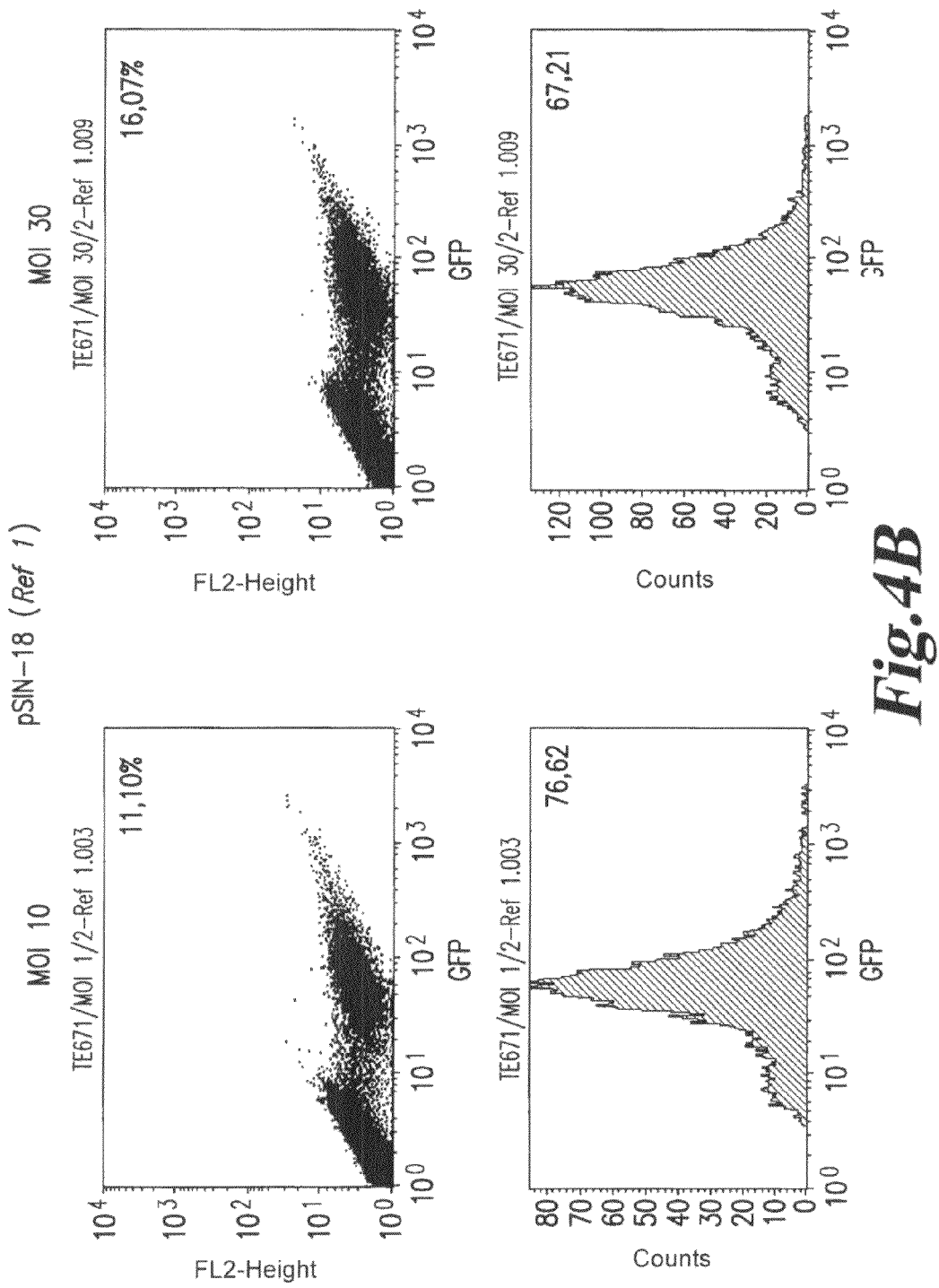
Figure 4C:
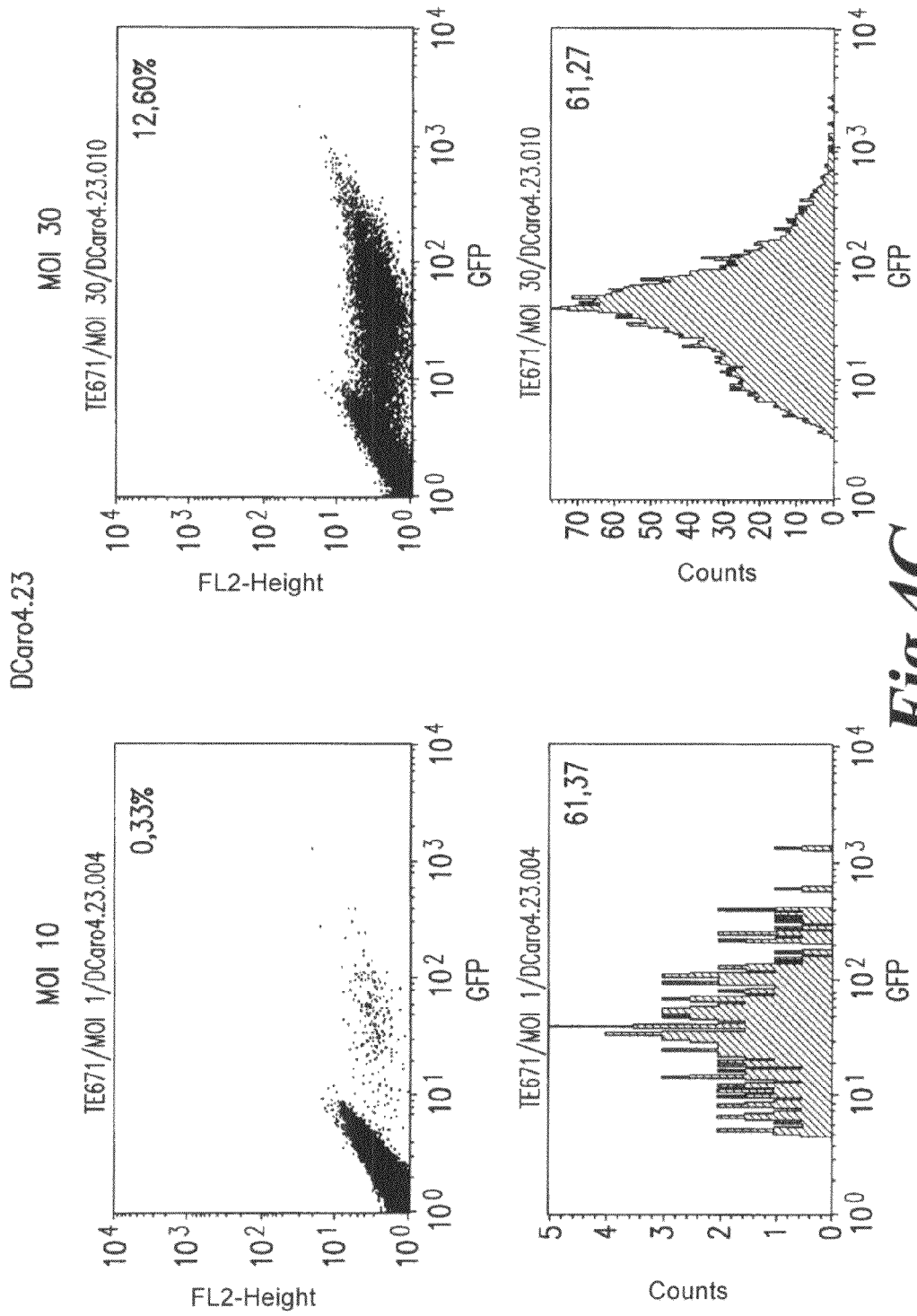
Figure 4D:
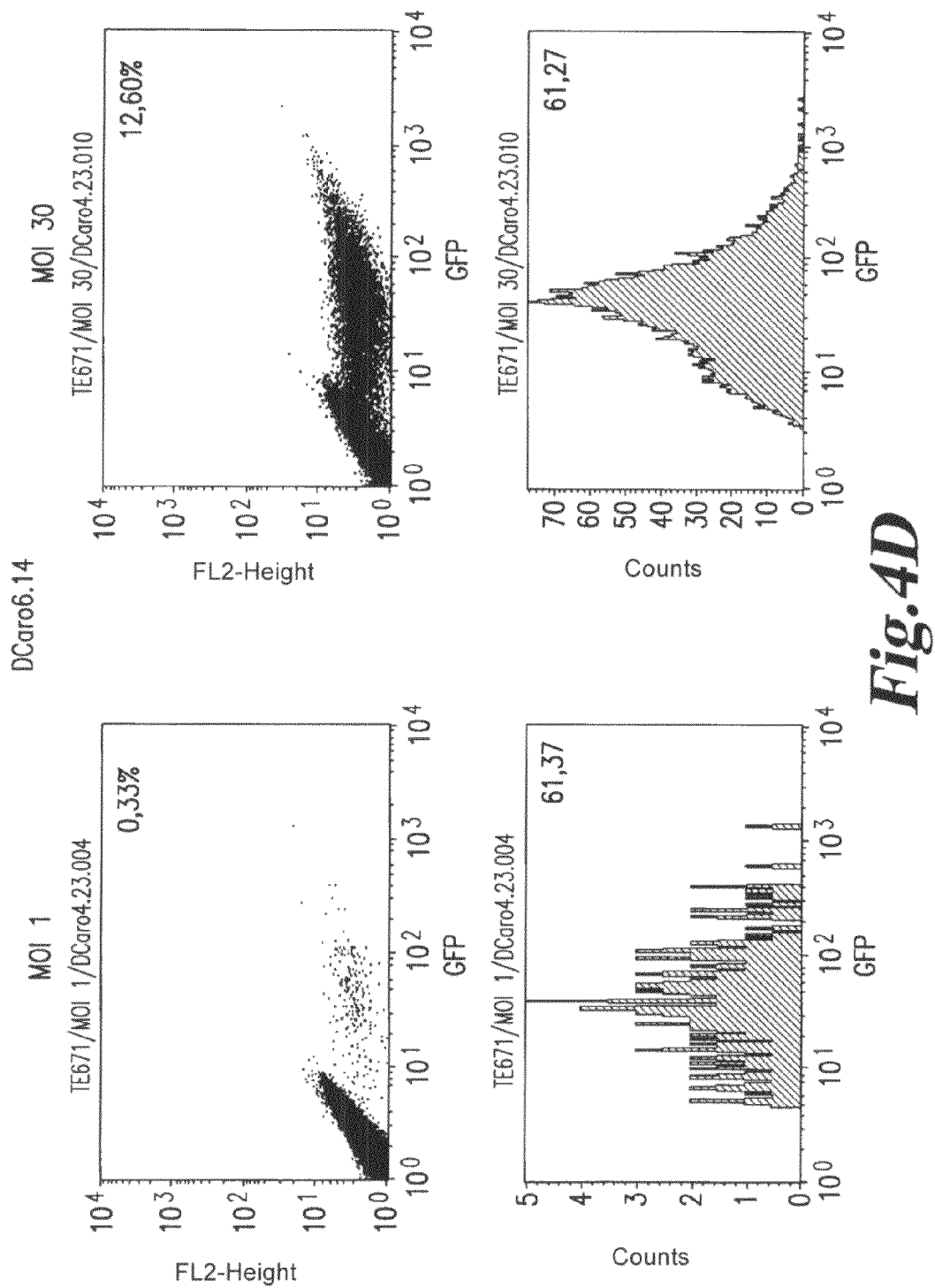
Figure 4E:
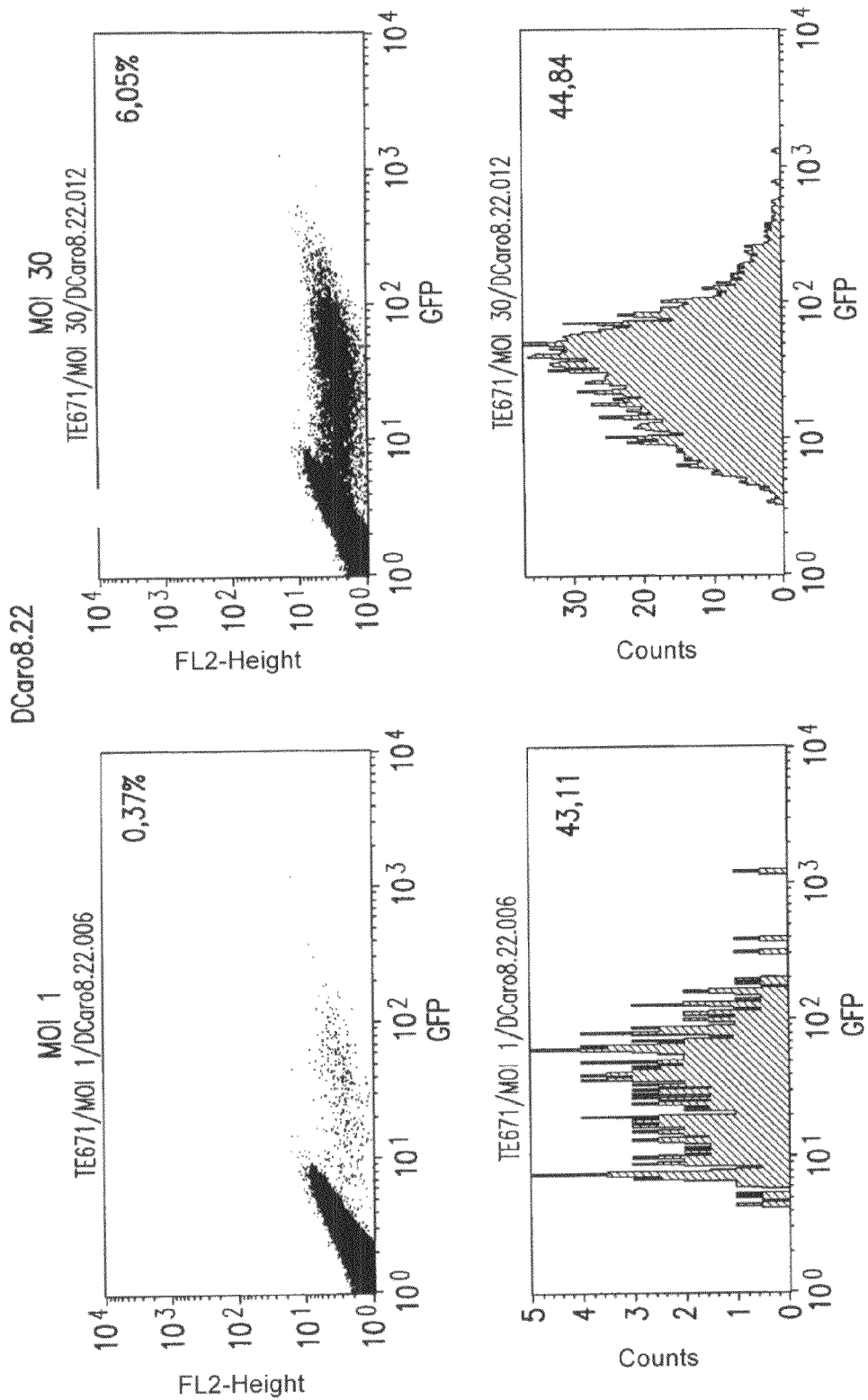

With gammaretrovectors, the mean eGFP fluorescence intensity remained stable over time with all vectors tested, which ever insulator was used (FIG. 3A) but the percentage of eGFP expressing cells gradually decreased when transduced with Insulator 1 carrying vectors as shown in FIG. 3B, suggesting either a gradual silencing effect over time or genetic instability of insulator 1 placed in that context.

Figure 5A:
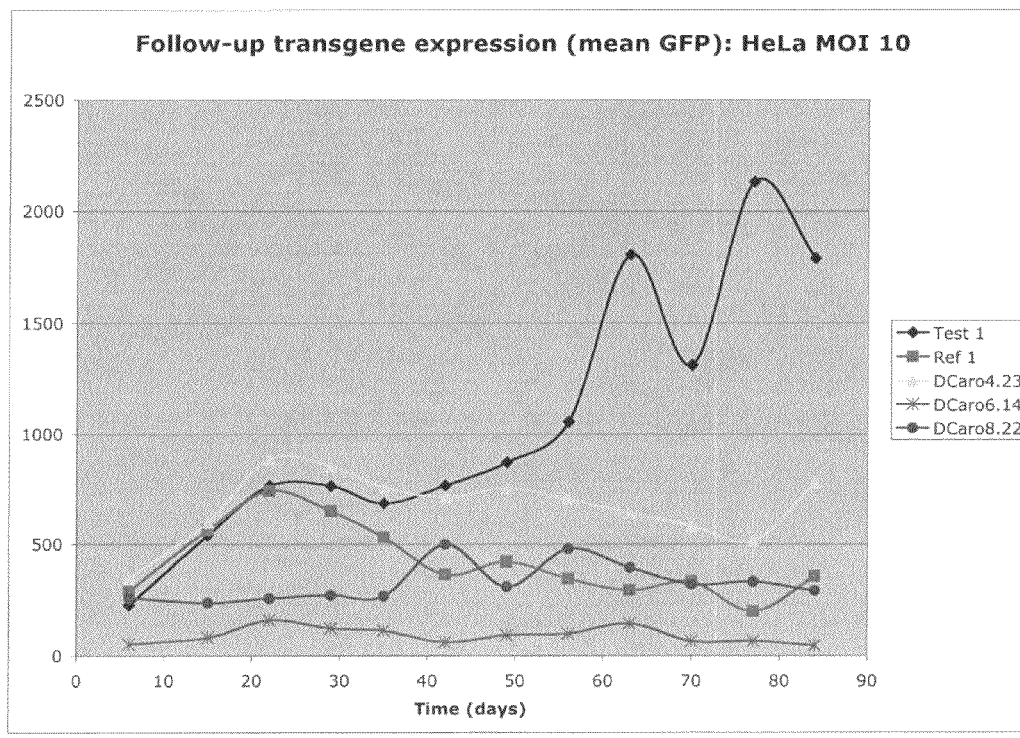
FIG. 5 shows the evolution A. of mean fluorescence in HeLa cells over time and B. percentage of fluorescing over 12 consecutive weeks in culture with lentiviral vectors.
Figure 5B:
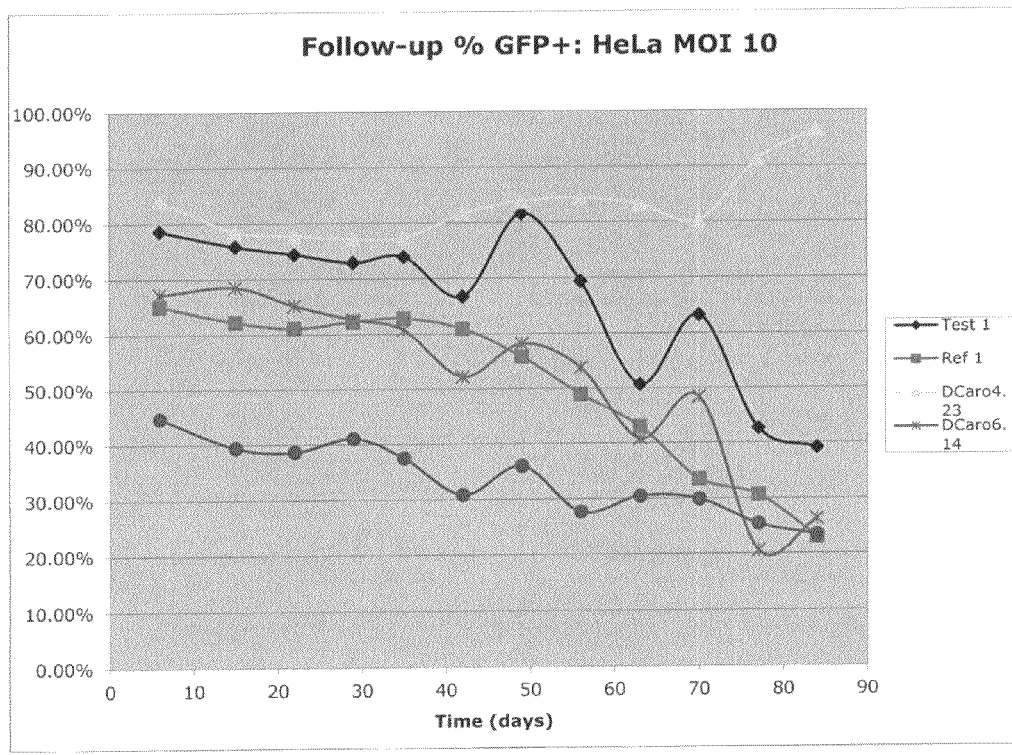

Again, FIG. 5B shows the dramatic decrease from 70 to 25% in the percentage of eGFP expressing cells with the lentivector including Insulator 1 (Dcaro6.14), over our 12 weeks follow-up in Hela cells. The same holds true in human haematopoietic primary stem cells from cord blood.

FIGS. 5A and 5B, clearly illustrate that the single vector which mediates stable and sustained expression of the transgene over time is Dcaro4.23, which includes four repeats of Insulator 2. With the two reference constructs, pSIN-18/Ref1 and Lenp29/Test1, the % of eGFP expressing cells dramatically decreased from 65% to 22% and 80% to 40% respectively while Dcaro4.23 remains in the 80% range. Similar observations can be made on the expression level which remains in the 600-700 mean eGFP fluorescence with Dcaro4.23, while it decreases with Ref1 and dramatically increases with Test1.

4× Insulator 2 Genetic Stability in Hela Transduced Cells

PCR was performed from primers in flanking regions of the insulators at both ends, leading to an 219 bp long amplicon in the presence of 4× Insulator 2 and to a 99 bp long amplicon with the non-insulated vector, e.g.: Test1/Lenp29. Where insulator 2 has been deleted or rearranged, it is expected that additional bands would have appeared in between 219 and 99 bp and in between week 2 to 11, which is not seen (FIG. 6A). Instability levels were also monitored for both DCaro8.22, which comprises 8 repeats of insulator2 and DCaro6.14, based on 6×CTCF (FIG. 6B).

2.4 Virus Titers

Similarly to transgene expression level, the addition of Insulator 2 resulted in much higher titres as compared to Insulator 1.

With gammaretrovirus constructs, the variation in titer between Insulator 2 and Insulator 1 viruses encompassed two orders of magnitude when comparing both identical Virus// different Insulator combinations directly. Interestingly, titers of both p19 and 20 were significantly higher than with the reference LTR-p7 control as shown in FIG. 2. With lentivirus constructs, titres of Insulator 1 and Insulator 2 carrying vectors also significantly differed, by an order of magnitude, as shown on Table 4 (p24 titres shown).

TABLE 4

| Lentivector | Insulator | Functional titre: 293 cells | p24 titre pfu/ml | mean Fluorescence |
|---|---|---|---|---|
| Lenp29/Test 1 | N/A | 9.75E+08 | 4.39E+09 | 951 |
| pSIN-18/Ref1 | N/A | 2.09E+09 | 1.24E+10 | 257 |
| DCaro4.23 | 4xIns2 | 1.17E+09 | 1.10E+10 | 667 |
| DCaro6.14 | 6xIns1 | 3.55E+08 | 6.34E+09 | 47 |

2.5 Comparing Various Numbers of Insulator 2 Repeats in Retroviral Vectors

In order to investigate whether the number of CTF repeats present in Insulator 2 constructs impacts or not on the performances of these various constructs, both gammaretrovirus and lentivirus vectors were designed with either 2×CTF, 4×CTF or 7/8 CTF repeats as GIEs cloned into the deleted SIN LTRs.

The most interesting data were monitored with vectors containing the 4×CTF GIE (p20, Table 5A and 4× C1.1 Table 6B), wherein for both types of vector, mean fluorescence exceeded all other tested vector types. This preference holds true in reference both transgene expression levels and virus titres generated (Table 4), wherein for example the titer of p20 is on the 10E5 pfu/ml range but this is without the normal step of selecting the best producers; this is bulk producer cell pool and could translate easily into over 10E6 with additional selection procedures.

Surprisingly, 7/8×CTF (p24 in Table 6A and 7×c12 in Table 6B) did not perform better than 2× (p22 in Table 5A and 2× c16 in Table 5B) and in the case of p24 mean fluorescence was less than 50% of p22.

The inventors have also found some unexpected effects with the 7×CTF element which may be due to instability of this element in the virus, (or other as yet unexplained reasons). These effects were also seen during the preparation of plasmids comprising this element, for transfection.

TABLE 5A

Comparing various repeats of Insulator 2 in Gammaretrovectors

| Plasmid Name | TF25 % GFP+ cells | Mean Fluorescence |
|---|---|---|
| p7 | 2.67% | 24.77 |
| p20 | 14.14% | 48.85 |
| p22 | 10.41% | 24.04 |
| p24 | 0.37% | 19.70 |

TABLE 5B

Comparing various repeats of Insulator 2 in Lentivectors

| Vector | Number of GFP+ cells | Mean Fluorescence |
|---|---|---|
| 4x cl.1 | 368 | 464.64 |
| 6x cl.8 | 143 | 136.84 |
| 2x cl.6 | 103 | 96.18 |
| 7x cl.2 | 166 | 81.42 |

Observations made with lentivectors corroborate these data to an even broader extent as shown on FIGS. 5A and 5B, where the multiplicity of infection (MOI) has been normalised so that the number of infectious virus particles is identical whichever vector is tested, irrespective of the initial difference observed in virus production titers. Therefore, using the same MOI, striking differences are monitored between the 4× Ins2 (Dcaro4.23) and the 8× Ins2 (Dcaro8.22) vectors: whether in the initial % of transduced cells with over 84% and 45% respectively; or during follow-up, after 12 weeks, Dcaro4.23 remains in the 80% range while Dcaro8.22 levels have dropped to 22%, half of the initial % of transduced cells. Mean fluorescence levels with the 8× Ins2 vector also are half of that observed with the 4× Ins2. Similar data have been observed in haematopoietic cells from cord blood (data not shown).

2.6 Use of Alternative Internal Promoters in Insulator 1 and Insulator 2 Gammaretroviral Vectors Two different internal promoters, driving the expression of the transgene from the SIN/Insulated vectors were tested. The first one is a strong enhancer/promoter derived from the Fr-MuLV FB29 strain virus LTR, referred to hereafter as "U3". Its characteristics have already been described (Sitbon et al, 1994; Cohen-Haguenauer et al, 1998 & 2006) and in particular its potential to express transgenes at high levels in both haematopoietic and CNS stem cells.

The second promoter used is the "hPGK" originating from a housekeeping gene, identified as a ubiquitous, low level sequence which is not susceptible to extensive variations expression level.

Figure 8A:
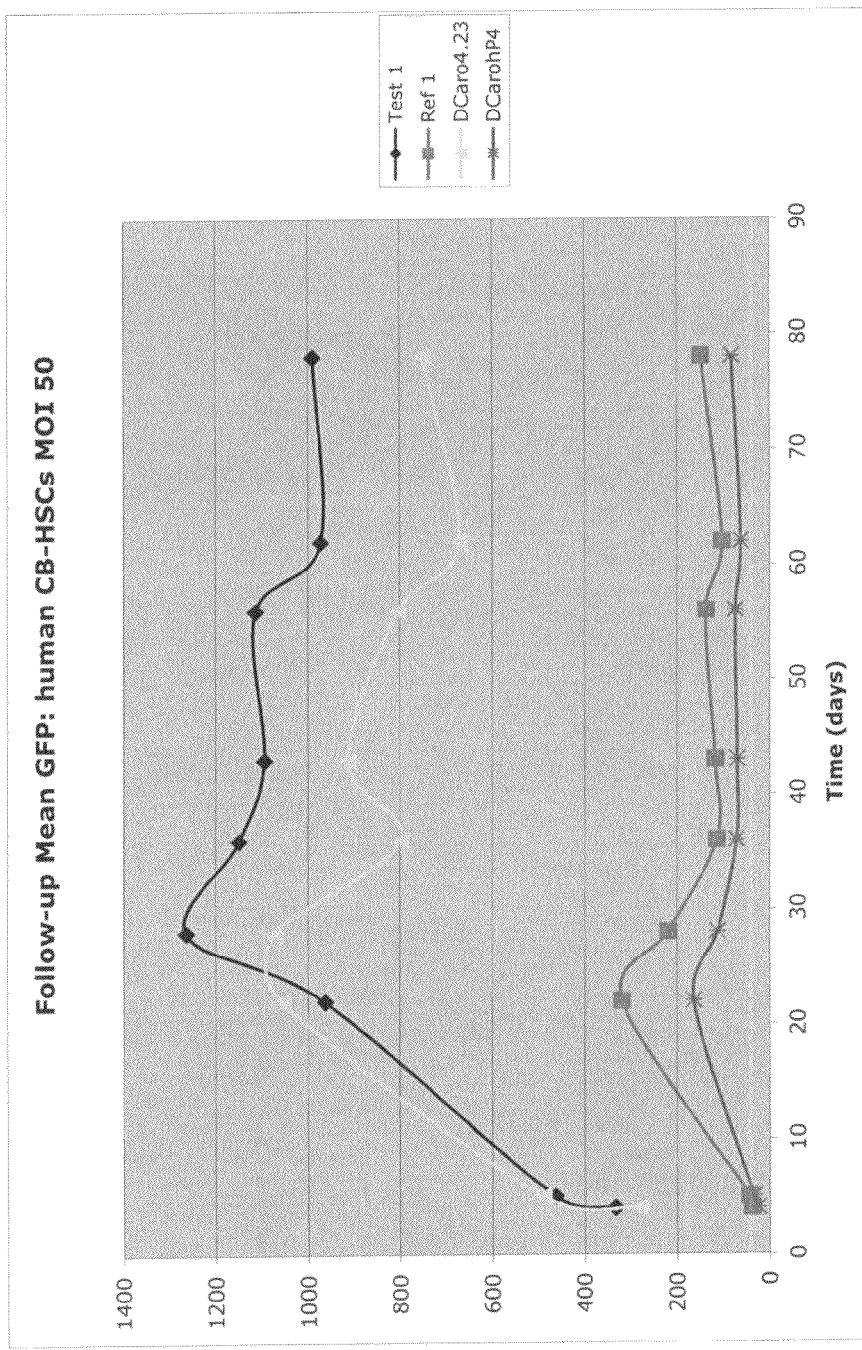
FIG. 8 shows the evolution A. of mean fluorescence in human CD34+ cells over 12 consecutive weeks in culture and B. percentage of human CD34+ cells fluorescing over time with various lentivirus vectors.
Figure 8B:
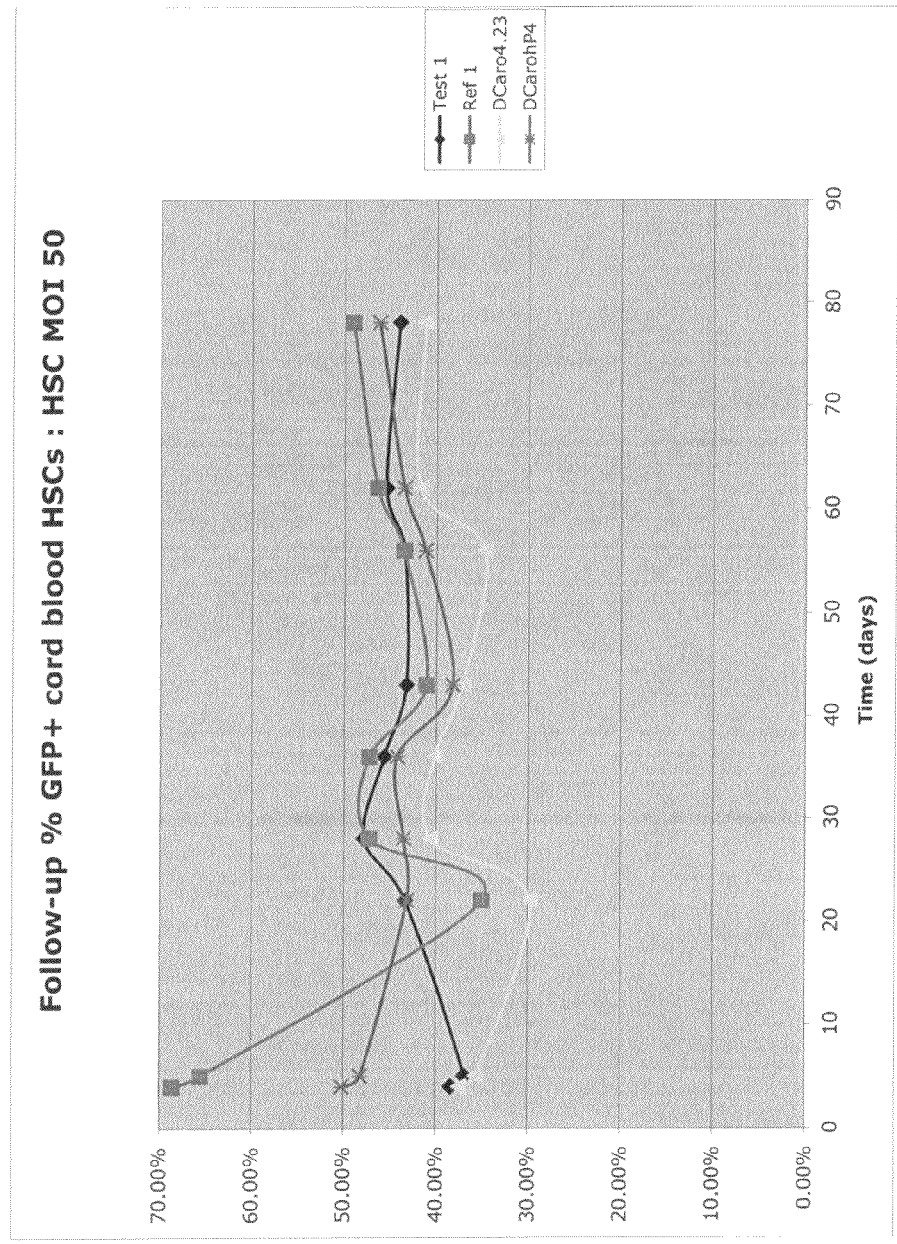

The two promoters have been selected according to prior observations and publications, which clearly show that the expression levels driven from the virus-derived promoter and the housekeeping promoter are distinct, although other factors such as the cell type may be a factor due to virus transcriptional tropism, while the housekeeping promoter will provide equal levels whatever the host cell.

long-term expression into human cord blood haematopoietic stem cells, as shown in FIG. 7 and FIGS. 8A and 8B, with a 12 weeks follow-up. It is noticeable that both the expression level and the percentage of transgene expressing cells remain stable over time with Dcaro4.23 and DCaro4hP.

Figure 9A:
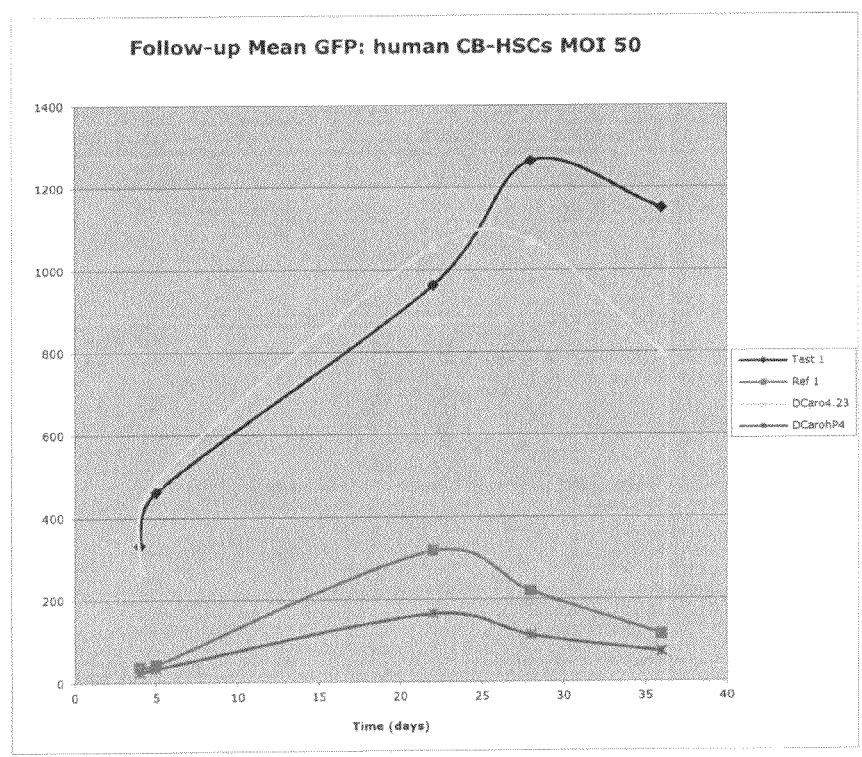
FIG. 9 shows the evolution A. of mean fluorescence in human CD34+ cells over 5 weeks and B. percentage of human CD34+ cells fluorescing over 5 weeks with various lentivirus vectors at MOI 5 and MOI 50.
Figure 9B:
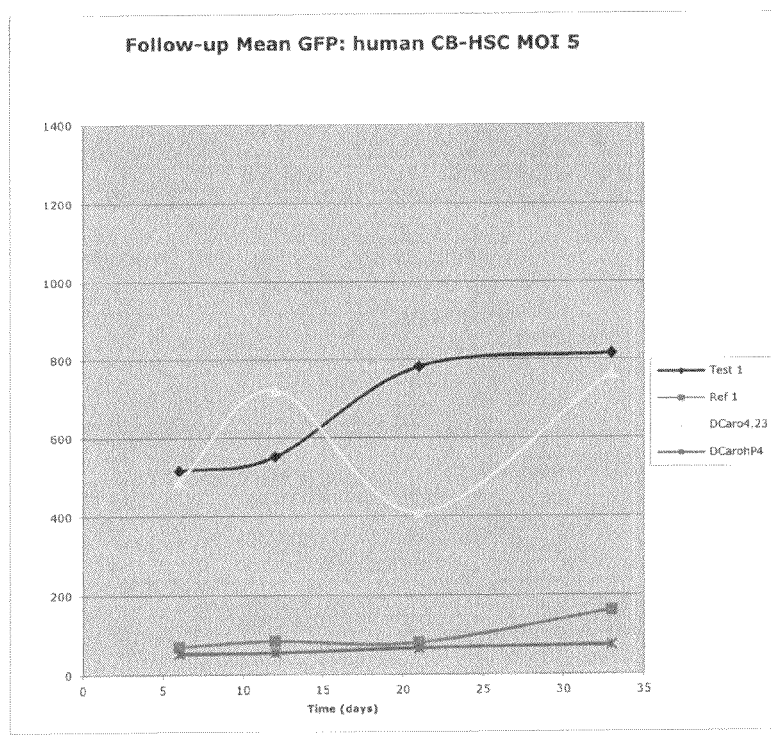

In addition it is noticeable that in the 4× Ins2 vectors, the mean expression level is conserved whatever the MOI under use, as shown in FIG. 9; while with Dcaro4.23 this level is sustained in the 700-800 range, over a prolonged period (FIG. 8A), with both Ref1 and Test1 there is a markedly distinct level of eGFP expression with a MOI of 50 is applied as compared to a MOI of 5. This striking observation reveals the remarkable power of the 4× Insulator 2 placed in the retroviral LTR context, since each trangene-expressing cassette integrant has become independent from its neighbouring genetic environment and a homogenous expression pattern is observed, which depends on the strength of the internal promoter placed between the two flanking insulator sequences.

Interestingly, the difference in the mean transgene expression level based on eGFP reporter is markedly increased in human primary haematopoietic stem cells as compared to other cell-lines, as shown on Table 6 and FIG. 8A, since as mentioned, a log-range expression level difference is observed with Dcaro4.23 (Fr-MuLV U3 as internal promoter) and DCaro4hP (with hPGK as internal promoter).

TABLE 6

| | LSIN-U3/Test1 | | 4xCTF-U3/DCaro4.23 | | pSIN-18/Ref1 | | 4xCTF-hP/DCaro4hP | |
|---|---|---|---|---|---|---|---|---|
| Weeks | Percentage of GFP+ cells | Mean Fluorescence | Percentage of GFP+ cells | Mean Fluorescence | Percentage of GFP+ cells | Mean Fluorescence | Percentage of GFP+ cells | Mean Fluorescence |
| 1 | 0.38% | 333.41% | 0.37% | 280.18% | 0.69% | 37.40% | 0.50% | 24.91% |
| 3 | 0.43% | 1462.89% | 0.30% | 1556.39% | 0.35% | 318.98% | 0.43% | 164.46% |
| 4 | 0.48% | 1864.00% | 0.41% | 1072.00% | 0.47% | 220.11% | 0.44% | 112.31% |
| 5 | 0.46% | 1150.00% | 0.40% | 798.94% | 0.47% | 114.21% | 0.44% | 72.12% |
| 6 | 0.43% | 1095.00% | 0.37% | 914.00% | 0.41% | 117.68% | 0.38% | 70.89% |
| 7 | 0.44% | 1114.00% | 0.35% | 804.86% | 0.44% | 137.55% | 0.41% | 74.63% |
| 8 | 0.45% | 972.55% | 0.42% | 672.55% | 0.46% | 103.23% | 0.44% | 62.95% |
| 10 | 0.44% | 990.18% | 0.41% | 851.38% | 0.49% | 148.49% | 0.46% | 82.63% |

While the intensity of expression was completely shielded and overall quite low and similar with Insulator 1 derived vectors whatever the strength of the internal promoter used, significant differences were monitored with vectors containing Insulator 2, as shown on FIGS. 3A, 5A, 7 and 8A. In heamatopoietic stem cells cultured over 12 weeks, the mean flurorescence differed by roughly a log range and remained stable as such over time. This observation demonstrates that Insulator 2 vectors mediate expression according to the strength of the internal promoter. The expression cassette is thus becoming strictly insulated and independent from neighbouring sequences and silencing.

In experiments using the control non-insulated vectors, as was expected lower expression levels were observed on average when the hPGK promoter was driving eGFP expression in comparison to when U3 was driving eGFP expression; an observation which was also seen with lentivectors as shown in Table 4, since pSIN-18 comprises a hPGK promoter (mean recorded eGFP fluorescence: 76) while Lenp29 comprises a U3 promoter (mean eGFP fluorescence: 144).

2.7 Transduction of CD34+ Cells from Human Cord Blood

Insulated Self-Inactivating lentiviral vector DCaro.23 has a high titer and mediates efficient transduction and sustained

2.8 Genotoxicity

The development of retroviral vector-induced lymphoproliferative disease in patients with X-linked severe combined immunodeficiency (SCID-X1) otherwise successfully treated by the gene therapy has highlighted the need for safer vectors with reduced regulatory cross-talk with adjacent host cell genomic DNA. Using simple human HeLa cell culture, the inventors have observed that even self-inactivating LTR based lentiviral vectors may skew clonal survival over time (unpublished data). Using a combination of genome-wide non-restrictive linear amplification-mediated PCR that circumvents the limiting use of restriction enzymes during integration site analysis, and next generation sequencing technologies (GSF1× and GSF1× Titanium; Roche Diagnostics), the inventors aimed to assess the vector biosafety level of any integrating vector type by comprehensive integration site profiling.

Comprehensive integration site analyses is performed at regular intervals after transduction of cells (e.g. 1 week, 4 weeks, 8 & 12 weeks), thereby assessing the total number of retrieved integration sites, quantitative contribution of individual clones at a given time point and over time, formation of integration site clusters ('hotspots' or CIS, common integration sites) and characterization of vector targeted cellular genes (overrespresented gene class categories).

Genotoxicity studies have now indicated the effectiveness of the 4×CTF insulated gammaretrovectors in reducing the probability of selecting with time dominant clones, following integration into the host target cell genome. The assessment of putative residual genotoxicity is made by comparing the evolution of integration patterns in human target cells grown and sequentially sampled over a one to three months period with both reference (non-insulated) and test insulated vectors, using high-throughput pyro-sequencing.

Figure 22A:
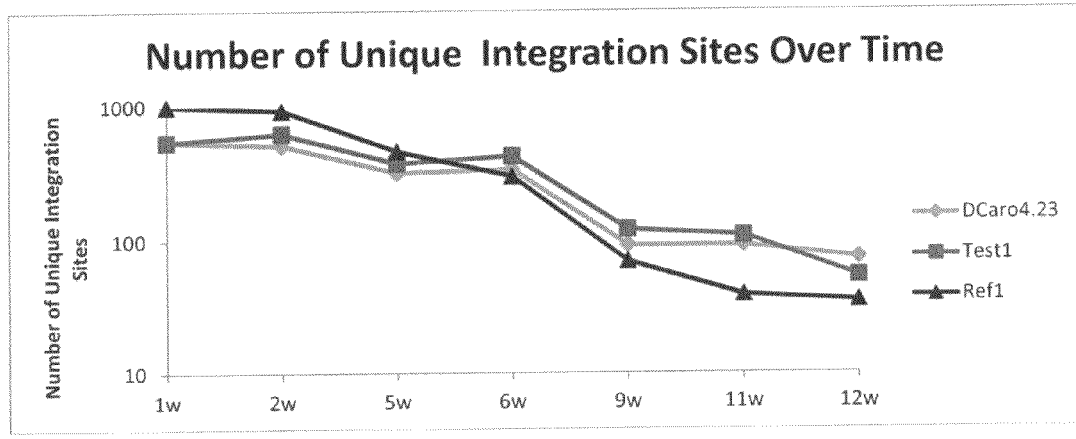
FIG. 22A shows number of unique integration sites over the time course of the genotoxicity experiment for the pSIN18 (Ref1), Test1-cPPT/Lenp29 (Test1) and DCaro4 vectors.
Figure 22B:
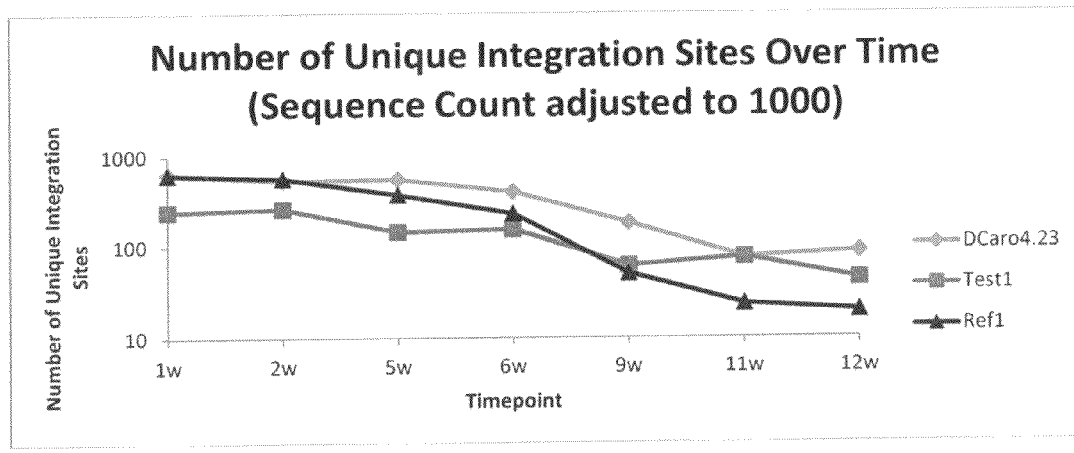
FIG. 22 B shows number of unique integration sites over the time course of the genotoxicity experiment for the pSIN18 (Ref1), Test1-cPPT/Lenp29 (Test 1) and DCaro4.23 vectors adjusted so that the total number of sequence sampled was 1000.

Data from the genotoxicity study are shown in Table 7 below and FIGS. 22A and 22B:

TABLE 7

| Week | DCaro4.23 | | | Test1-cPPT/Lenp29 | | | pSIN18 | | |
|------|-----------|-----|---------------------------|------|------|---------------------------|------|------|---------------------------|
|      | IS | SC | IS (SC adjusted to 1000) | IS | SC | IS (SC adjusted to 1000) | IS | SC | IS (SC adjusted to 1000) |
| 1  | 544 | 860  | 633 | 546 | 2253 | 242 | 997 | 1592 | 626 |
| 2  | 512 | 955  | 536 | 626 | 2406 | 260 | 925 | 1633 | 566 |
| 5  | 320 | 580  | 552 | 377 | 2620 | 144 | 463 | 1251 | 370 |
| 6  | 339 | 853  | 397 | 427 | 2800 | 153 | 301 | 1321 | 228 |
| 9  | 92  | 514  | 179 | 121 | 2001 | 60  | 70  | 1414 | 50  |
| 11 | 92  | 1241 | 74  | 109 | 1457 | 75  | 39  | 1701 | 23  |
| 12 | 74  | 859  | 86  | 54  | 1249 | 43  | 35  | 1805 | 19  |
| Total unique (ex. mappable) | 1736 (1570) | | | 1927 (1734) | | | 2624 (2344) | | |

Over the course of this study all three tested vectors showed a reduction in the total number of integration sites. When comparing the overall number of integration sites (per 1000 sequences) remaining for each vector after 12 weeks, the non-insulated constructs showed between a 2 to 4 fold reduction in insertion sites (pSIN18 reduced to 19 integration sites and Test1-cPPT/Lenp29 reduced to 43 integration), in comparison to the insulated vector DCaro4.23 which was reduced to 86 integration. Using this measurement of genotoxicity therefore the insulated vector DCaro4.23 which comprises the 4×CTF GIE showed a significantly lower level of genotoxicity than the commonly used pSIN 18 vector or the more closely related Test1-cPPT/Lenp29 vector.

Figure 23:
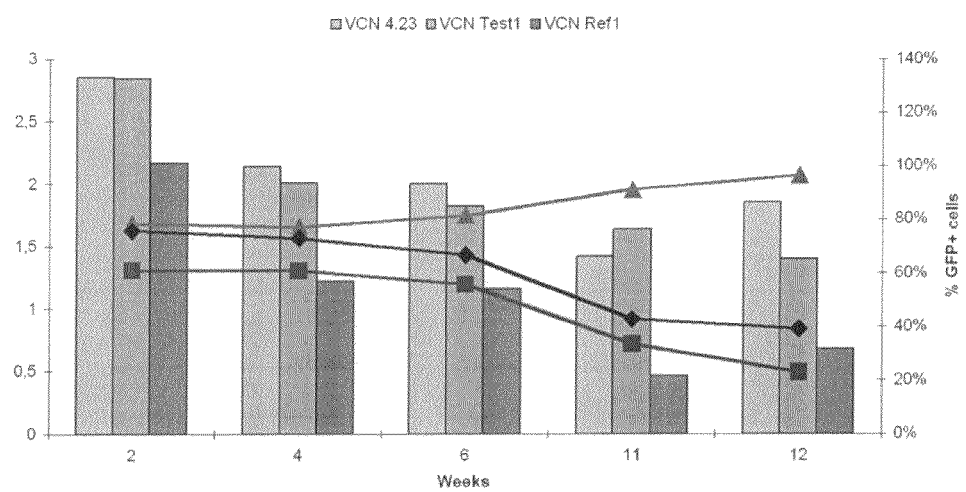
FIG. 23 shows a chart of the relationship between the vector copy number (VCN) and % GFP expressing cells over 12 weeks for HELA cells transduced with pSIN18 (Ref1), Test1-cPPT/Lenp29 (Test1) and DCaro4.23 vectors.

With reference to FIG. 23 it can be seen that with the DCaro4.23 vector, both VCN (Vector copy number) and % of transduced cells remain stable over the twelve week period of the experiment whereas with Test1-cPPT/Lenp29 vector (Test1), VCN decreases from 2.5 to 1.5 but % of GFP+ cells fell from 70 to 40% and pSIN18, VCN decreases from 2 to 0.7 while % GFP+ fell from 60 to 20%.

This experiment establishes that with the 4×CTF insulated lentivector, starting from an identical number of integration events leads to stable transduction and expression levels over time, while no such stability is observed with control non-insulated vectors either at the genetic or phenotypic level.

Figure 24:
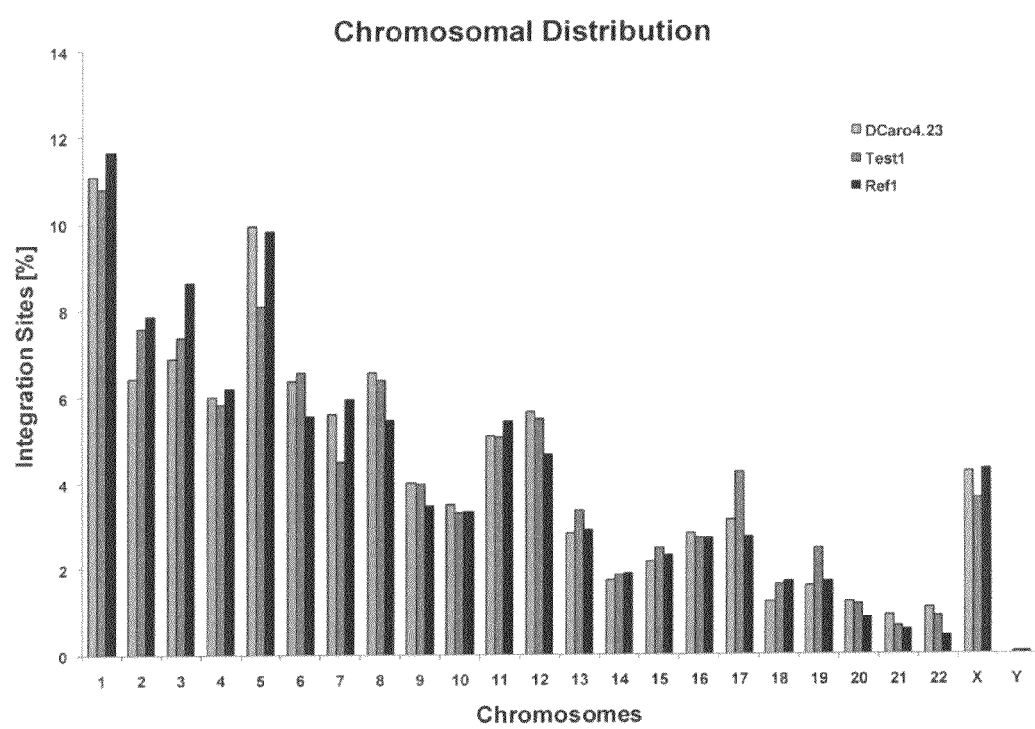
FIG. 24 shows the chromosomal distribution of integration sites in HELA cells transduced with pSIN18 (Ref1), Test 1-cPPT/Lenp29 (Test 1) and DCaro4.23 vectors.
Figure 25:
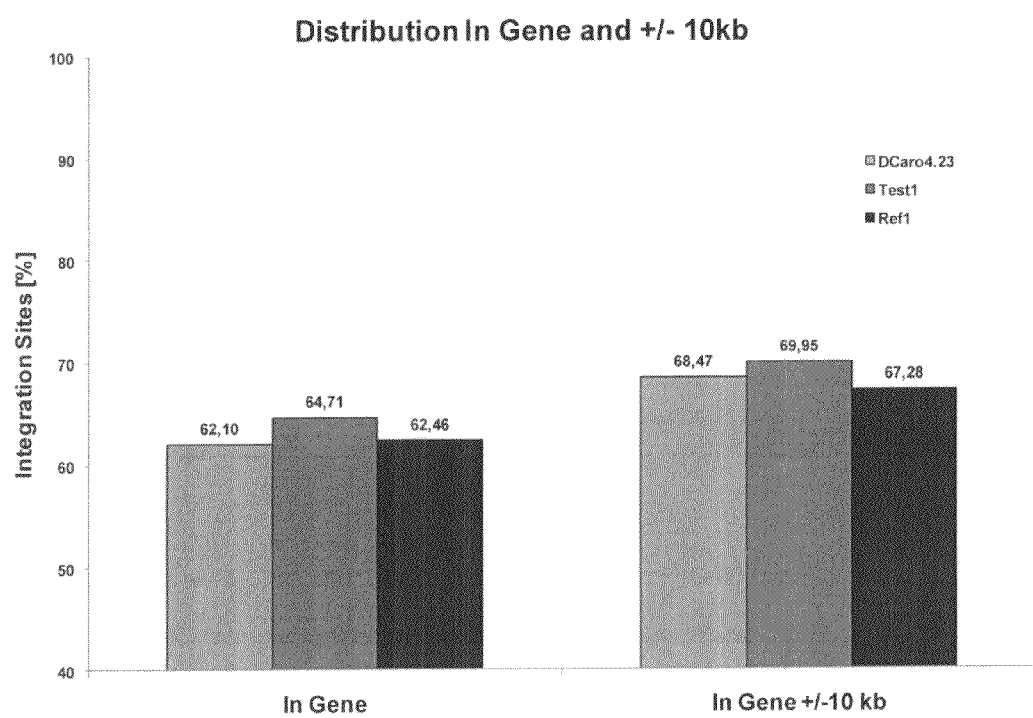
FIG. 25 shows the distribution of integration sites in or close to genes, in HELA cells transduced with pSIN18 (Ref1), Test 1-cPPT/Lenp29 (Test 1) and DCaro4.23 vectors.
Figure 26:
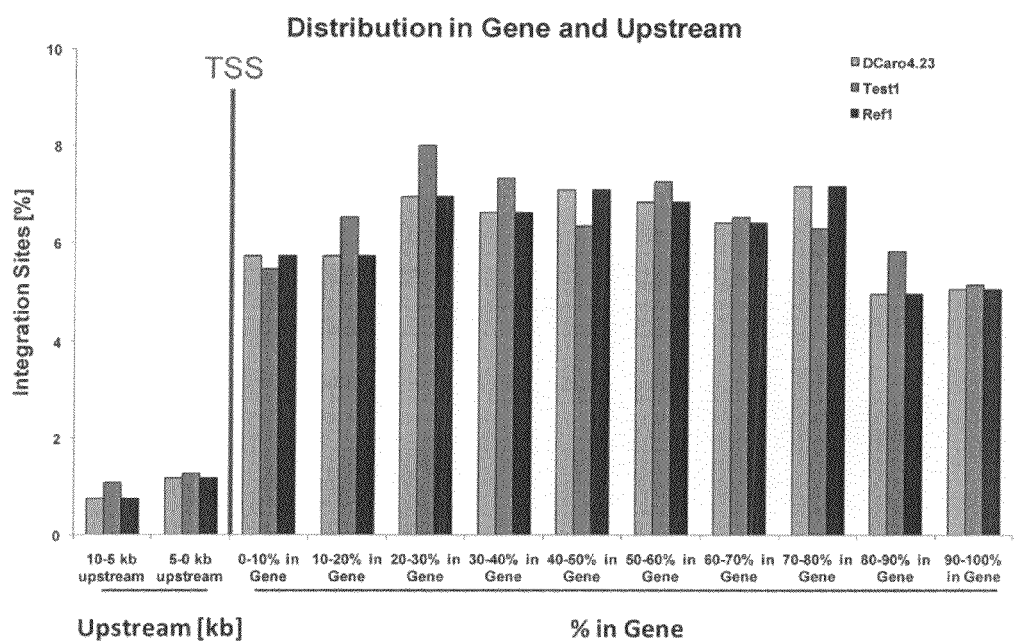
FIG. 26 shows the distribution of integration sites in genes or gene regulatory sequences, in HELA cells transduced with pSIN18 (Ref1), Test1-cPPT/Lenp29 (Test1) and DCaro4.23 vectors.

With reference to FIGS. 24, 25 and 26 it can also be seen that the insulated vector Dcaro4.23 behaves in a very similar manner to pSIN18 vector (Ref1) or Test1-cPPT/Lenp29 vector (Test1) in terms of its chromosomal distribution pattern (FIG. 24) or the distribution of integration sites in or around genes (FIGS. 25 and 26). Indicating that the presence of the insulating element does not affect the inter- or intra-chromosomal integration of the vector.

Table 8 shows an analysis of the distribution of integration sites for each of the tested vectors in one or more of the common integration sites identified for each of the vectors. No obvious differences were seen between the vectors in terms of the number of integrations in the common integration sites.

TABLE 8

| Vector | DCaro4.23 | LenP29 | pSIN18 |
|--------|-----------|--------|--------|
| # IS (total) | 1570 | 1734 | 2344 |
| # CIS | 82 | 100 | 183 |
| CIS order 2nd | 74 | 83 | 152 |
| 3rd | 5 | 12 | 18 |
| 4th | — | 3 | 2 |
| 5th | 2 | 2 | 4 |
| 6th | 1 | — | 2 |
| 7th | — | — | 1 |
| IS in CIS | 179 (11%) | 224 (13%) | 405 (17%) |

The data presented above indicates that although the vector comprising the insulator element shows similar patterns of integration distribution throughout the genome, whilst showing lower levels of clonal expansion associated with genotoxicity.

2.9 Transduction of Human hES Cell-Line hES Sa01

The inventors have also shown that the gene transfer vector according to the present invention can be transduced into human embryonic stem cells (hES).

The hES cell-line was transformed as follows:

Tissue was either partially dissected into clumps or completely dissociated into a population of free cells.

Approximately 800,000 cells were transduced using gene transfer vectors according to the present invention comprising (i) at least one insulator or (ii) no insulator, at a MOI of 50.

Transduction occurred under orbital agitation of no more than 8 revolutions per minute at 37° C. for 6 hours, in the presence of protamine sulfate at a concentration of 5 µg/ml in a final volume of 1 mL.

Cells are then separated into two equal groups, with the first group being plated directly and the second group being subject to trypsin digestion so as to disassociate the cells prior to plating. Both groups were then cultured using complete medium.

Cells were then subjected to fluorescence microscopy every ¾ days.

Figure 21:
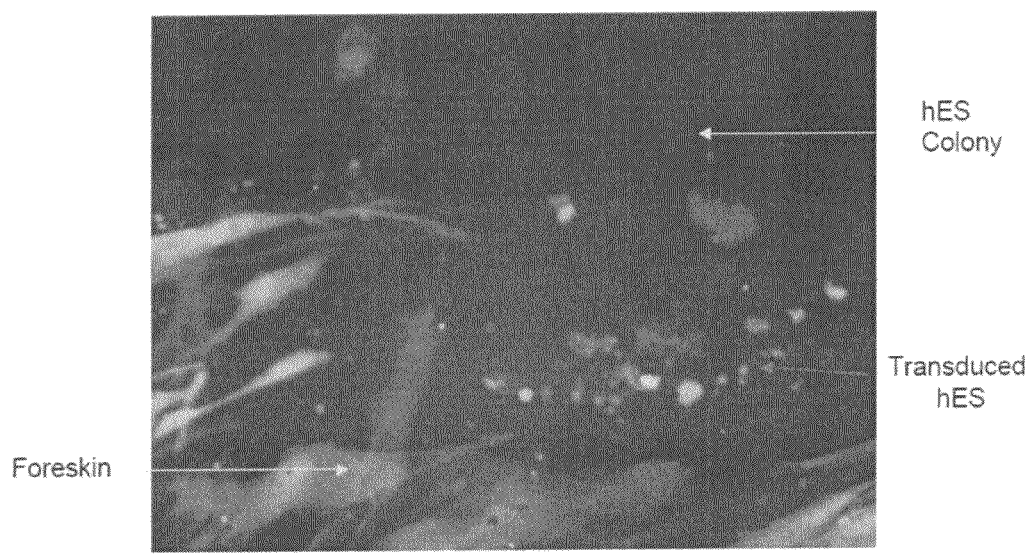
FIG. 21 shows an image of hES SA01 transduced with the DCaro4.23 insulated lentiviral vector on day 6 after transduction. Clear fluorescent transgene expression is seen in those human embryonic stem cells transduced with the vector.

At day 6 after transduction, fluorescent cells were observed indicating effective transduction and expression of the transgene starting using the lentiviral construct DCaro4.23 and the internal promoter Fr-MuLV-U3 (FIG. 21).

The inventors have also successfully tranduced into iPS (Induced pluripotent stem) cells vectors comprising GIEs according to the present Patent Application and established effective transduction and expression of transgenes using these constructs and in particular the lentiviral vector DCaro4.23.

Example 3

Conclusions

SIN-insulated retrovectors have been constructed with two candidate GIEs and compared to native and SIN-LTRs. With each constructs two internal promoters have been tested: either the strong Fr-MuLV-U3 or the housekeeping hPGK. The inventors have identified a specific combination of insulator 2 repeats which shows functional activity, high titres and boundary effect in both gammaretrovectors (p20) and lentivectors (DCaro4).

In target cells a dramatic shift of expression is observed with an homogenous expression profile, the level of which is linked to the promoter strength. These data remain stable in both HeLa cells and cord blood HSCs for over three months, irrespective of the multiplicity of infection (MOI). In comparison, control vectors show heterogeneous expression profiles with levels which depend on the MOI and prove unstable over time. The inventors have undertaken genotoxicity assessments in comparing integration patterns in human target cells sampled over three months using high-throughput pyro-sequencing. Preliminary data indicate a flat pattern without CIS meaning the vectors according to the present invention have another advantage with respect to prior art vectors pertaining to enhancer-blocking activity harbouring potential for reduced genotoxicity.

The inventors sought to design synthetic GIEs consisting of multimers of critical core sequences. The first insulator they designed consists of a new combination of CTCF binding sites: 42 bp FII sequence (CTCF1) derived from HS4 and 39 bp BEAD-A sequence (CTCF2) derived from the human T cell receptor alpha/delta locus and is known as Insulator 1. Insulator 1 consists of three repeats of the CTCF1-CTCF2 sequence.

The second insulator consists of multimerised CTF sites with various numbers of repeats. CTF otherwise known as a transcription factor, has recently been shown to act as a chromatin domain boundary that shields human telomeric genes from silencing.

When either of the two insulators were cloned into the LTR of simple gamma retroviral SIN constructs, virus production dramatically dropped, as compared to reference vectors with either full or SIN-LTRs. The inventors were able to identify key determinants which allow the production of insulated SIN gamma retroviral vectors with good titers.

Among these, a key sequence is the 3' untranslated region (3'UTR) derived from the Fr-MuLV FB29 strain which features have already been reported in full-LTRs recombinant retroviral vectors (Cohen-Haguenauer et al, 1998). The addition of this sequence caused a dramatic increase in the virus titers obtained with the insulated vectors; those containing Insulator 1 had titers increased by one order of magnitude while with Insulator 2, titers ranged across several log.

With the other element, a human-beta globin derived, synthetic polyA sequence was placed downstream of the vector 3'LTR, in order to facilitate the synthesis of full-length RNA transcripts to be packaged into virions, a paradoxical effect was observed, titers of Insulator1 containing constructs dramatically dropped while for constructs containing Insulator 2, titers increased by 3 to 5 fold.

These first observations showed significant differences between Insulators 1 and 2 and were verified by further experiments which were independently reproduced several times and led to identical data.

With insulator 1: (i) recombinant viruses are produced at much lower titers than controls, although rescued by the addition of Fr-MuLV 3'UTR and (ii) overall expression levels are also much lower as compared to full LTR vectors. The opposite is observed with Insulator 2, since both titers and expression levels are higher than with control vectors. It is noteworthy that with lentivectors, these same observations hold true, except that in primary human haematopoietic stem cells in which Lenp29 vector has a unique potential in terms of infectivity, with a higher percentage of transduced cells as compared to pSIN-18 and DCaro4.23, confirming prior observations.

In addition, an important observation has been made following long term monitoring of transduced and sorted eGFP positive HeLa cells which has been sustained over a 120 days period, alsoaiming at genotoxicity studies. Although the level of eGFP expression remained stable over time in each sample studied, a drop in the percentage of eGFP positive cells was gradually observed in p11 transduced cells, starting from day 30 and progressively dropping over time, from 90 to 30%.

Based on these observations, Insulator 2 has characteristics which appear to make it the most useful insulator element identified and because of this the inventors performed further experiments to determine the optimum number of repeats. Gammaretroviral vectors were constructed where either 2 copies, 4 copies or 7 copies of Insulator 2 in the SIN-virus LTR. Comparative experiments with these vectors indicate that the best levels of eGFP fluorescence are observed with 4×CTF, in comparison to either 2×CTF or 7×CTF vectors. In addition, both virus titres and expression levels of the reporter gene in target cells tend to be lower with 7×CTF vectors in comparison to 2×CTF vectors.

Similar data were obtained with a set of lentivectors with either 4× Ins2 (DCaro4.23) or 8× Ins2 (DCaro8.22), wherein titers differ by at least one log range in favour of DCaro4.23. In addition, when the multiplicity of infection (MOI), that is the ratio of infectious virus to cells is normalised, the infectious potential capacity to express the transgene following transduction and integration of insulated vectors, is much higher with DCaro4.23.

Finally, in primary haematopoietic CD34+ cells from cord blood, DCaro4.23 performed with characteristics fulfilling our initial requirements. The inventors search for a putative gene therapy vector with decreased genotoxicity levels but no drop in integration efficacy has therefore resulted in the lentivirus construct DCaro4.23. Further aspects of the behaviour of Dcaro4.23 in particular when the FR-MuLV 3'UTR is included remain to be investigated and could potentially increase the utility of this vector further, such further constructs would also require validation particularly in terms of its genotoxicity. In addition the gammaretrovirus vectors p19 and p20 also represent putative gene therapy constructs.

REFERENCES

Marina Cavazzana-Calvo, Salima Hacein-Bey, Genevieve de Saint Basile, Fabian Gross, Eric Yvon, Patrick Nusbaum, Françcoise Selz, Christophe Hue, Stéphanie Certain, Jean-Laurent Casanova, Philippe Bousso, Françoise Le Deist, Alain Fischer. Gene Therapy of Human Severe Combined Immunodeficiency (SCID)-X1 Disease *Science* 28 April 2000: Vol. 288. no. 5466, pp. 669-672.

Coffin, J. M., Retroviridae: The viruses and their replication, In Fundamental Virology, Third Edition, B. N. Fields, et al., Eds., Lippincott-Raven Publishers, Philadelphia, 1996.

Cohen-Haguenauer O; Restrepo L M; Masset M; Bayer J; Dal Cortivo L; Marolleau J P; Benbunan M; Boiron M; Marty M Efficient transduction of hemopoietic CD34+ progenitors of human origin using an original retroviral vector derived from Fr-MuLV-FB29: in vitro assessment Human gene therapy 1998; 9(2):207-16.

Dull, T., Zufferey, R., Kelly, M., Mandel, R. J., Nguyen, M., Trono, D. & Naldini, L. (1998) *J. Virol.* 72, 8463-8471.

Hacein-Bey-Abina S, Von Kalle C, Schmidt M, et al. LMO2-associated clonal T cell proliferation in two patients after gene therapy for SCID-X1. Science. 2003; 302: 415-419.

Kim T H, Abdullaev Z K, Smith A D, Ching K A, Loukinov D I, Green R D, Zhang M Q, Lobanenkov V V, Ren B (2007). "Analysis of the vertebrate insulator protein CTCF-binding sites in the human genome". *Cell* 128 (6): 1231-45.

Kingsman S M, Mitrophanous K, Olsen J C. Potential oncogene activity of the woodchuck hepatitis post-transcriptional regulatory element (WPRE). Gene Ther. 2005 January; 12(1):3-4.

Ohlsson R, Renkawitz R, Lobanenkov V (2001). "CTCF is a uniquely versatile transcription regulator linked to epigenetics and disease". *Trends Genet.* 17 (9): 520-7.

Rupp R A, Kruse U, Multhaup G, Göbel U, Beyreuther K, and Sippel A E (1990). Chicken NFI/TGGCA proteins are encoded by at least three independent genes: NFI-A, NFI-B and NFI-C with homologues in mammalian genomes. Nucleic Acids Res. 1990 May 11; 18(9): 2607-2616.

Marc Sitbon, Brigitte Sola, Leonard Evans, Jane Nishio, Stanley F. Hayes, Kate Nathanson, Claude F. Garon, Bruce Chesebro. Hemolytic anemia and erythroleukemia, two distinct pathogenic effects of Friend MuLV: Mapping of the effects to different regions of the viral genome. Cell—26 Dec. 1986 (Vol. 47, Issue 6, pp. 851-859)

Tae Hoon Kim, Ziedulla K. Abdullaev, Andrew D. Smith, Keith A. Ching, Dmitri I. Loukinov, Roland D. Green, Michael Q. Zhang, Victor V. Lobanenkov and Bing Ren. Analysis of the Vertebrate Insulator Protein CTCF-Binding Sites in the Human Genome Volume 128, Issue 6, 23 Mar. 2007, Pages 1231-1245.

Xun Ye, Min Liang, Xia Meng, XiaoWei Ren, HongZhuan Chen, Zong-Yi Li, ShaoHeng Ni, Andre Lieber and Fang Hu. Insulation from viral transcriptional regulatory elements enables improvement to hepatoma-specific gene expression from adenovirus vectors Biochemical and Biophysical Research Communications Volume 307, Issue 4, 8 Aug. 2003, Pages 759-764.

Xie X, Mikkelsen T S, Gnirke A, Lindblad-Toh K, Kellis M, Lander E S (2007). "Systematic discovery of regulatory motifs in conserved regions of the human genome, including thousands of CTCF insulator sites". Proc. Natl. Acad. Sci. U.S.A. 104 (17): 7145-50.

Zufferey, R., Dull, T., Mandel, R. J., Bukovsky, A., Quiroz, D., Naldini, L. & Trono, D. (1998) *J. Virol.* 72, 9873-9880.

The invention claimed is:

1. An integrating gene transfer viral vector (IGTV) which comprises at least one genetic insulator element (GIE), wherein said at least one GIE comprises at least two copies of an element selected from the group consisting of (A) a CTF binding site; and (B) a sequence consisting of a first CTCF binding site and a second CTCF binding site: wherein the CTF binding site is selected from the group consisting of SEQ ID NO:26, SEQ ID NO:28, SEQ ID NO:29, and SEQ ID NO:30; and wherein said first and said second CTCF binding sites are from regulatory sequences of different genes and wherein said first and second CTCF binding sites comprise a different sequence selected from the group consisting of SEQ ID:7, SEQ ID NO:8, SEQ ID NO:27, and SEQ ID NO:31, wherein the at least one GIE is positioned in the vector such that following genomic insertion of the IGTV, the at least one GIE is positioned between a genomic sequence and the coding sequence of the IGTV.

2. The IGTV according to claim 1, wherein the at least one GIE comprises at least two copies of said sequence consisting of said first and second CTCF binding site and comprises a sequence selected from the group consisting of SEQ ID NO: 7, SEQ ID NO: 8, SEQ ID NO: 27 and SEQ ID NO: 31.

3. The IGTV according to claim 1, wherein said at least one GIE comprises the sequence SEQ ID NO: 6.

4. The IGTV according to claim 1, wherein the at least one GIE comprises said CTF binding site selected from the group consisting of SEQ ID NO: 26, SEQ ID NO: 28, SEQ ID NO: 29, SEQ ID NO: 30.

5. The IGTV according to claim 4, wherein said GIE comprises between two and eight copies of said CTF binding site.

6. The IGTV according to claim 1, wherein said IGTV is a retrovirus vector.

7. The IGTV vector according to claim 6, wherein IGTV is self-inactivating following insertion into a genome.

8. The IGTV according to claim 1, which further comprises an exogenous enhancer.

9. The IGTV according to claim 8, wherein said exogenous enhancer is positioned between said GIE and an exogenous transgene encoded by said IGTV.

10. The IGTV according to claim 9, wherein said enhancer is selected from the group consisting of viral enhancers, eukaryotic enhancers, animal enhancers, mammalian enhancers.

11. The IGTV according to claim 8, wherein said enhancer comprises the sequence SEQ ID NO: 22.

12. The IGTV according to claim 1, which further comprises a polyA tail.

13. A cell, comprising the IGTV according to claim 1.

* * * * *